US 7,339,051 B2

(12) United States Patent
Crooke et al.

(10) Patent No.: US 7,339,051 B2
(45) Date of Patent: Mar. 4, 2008

(54) COMPOSITIONS AND METHODS FOR THE TREATMENT OF SEVERE ACUTE RESPIRATORY SYNDROME (SARS)

(75) Inventors: Stanley T. Crooke, Carlsbad, CA (US); David J. Ecker, Encinitas, CA (US); Rangarajan Sampath, San Diego, CA (US); Susan M. Freier, San Diego, CA (US); Christian Massire, Carlsbad, CA (US); Steven A. Hofstadler, Vista, CA (US); Kristin Sannes Lowery, Vista, CA (US); Eric E. Swayze, Carlsbad, CA (US); Brenda F. Baker, Carlsbad, CA (US); C. Frank Bennett, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 402 days.

(21) Appl. No.: 10/831,901

(22) Filed: Apr. 26, 2004

(65) Prior Publication Data

US 2005/0100885 A1    May 12, 2005

Related U.S. Application Data

(60) Provisional application No. 60/565,370, filed on Apr. 26, 2004, provisional application No. 60/483,579, filed on Jun. 27, 2003, provisional application No. 60/477,637, filed on Jun. 10, 2003, provisional application No. 60/468,562, filed on May 6, 2003, provisional application No. 60/468,627, filed on May 6, 2003, provisional application No. 60/467,770, filed on Apr. 30, 2003, provisional application No. 60/466,426, filed on Apr. 28, 2003.

(51) Int. Cl.
C07H 21/02    (2006.01)
C07H 21/04    (2006.01)

(52) U.S. Cl. .................. 536/24.5; 536/23.1; 536/24.3; 536/24.33

(58) Field of Classification Search ............... 536/23.1, 536/24.3, 24.33, 24.5
See application file for complete search history.

(56) References Cited

U.S. PATENT DOCUMENTS 5,707,866 A    1/1998    Brakier-Gingras (Continued)

FOREIGN PATENT DOCUMENTS

CN    1458281    11/2003

(Continued)

OTHER PUBLICATIONS

Kurreck et al. Design of antisense oligonucleotides stabilized by locked nucleic acids. Nucleic Acids Research, 2002 vol. 30, pp. 1911-1918.*

(Continued)

Primary Examiner—Sean McGarry
Assistant Examiner—Terra Cotta Gibbs
(74) Attorney, Agent, or Firm—Knobbe, Martens, Olson and Bear, LLP.

(57) ABSTRACT

The present invention provides design and synthesis of oligomeric compounds and compositions that can be administered to reduce the activity of SARS virus in vivo or in vitro, to prevent or treat SARS virus-associated disease, to detect AARS virus, and to diagnose SARS virus-associated diseases.

18 Claims, 1 Drawing Sheet

```
pairing mask  *******------(((((((((------[[[[[--))))))))))-----------------------]]]]-----
              A            B          C      D                                    E
TGEV          UUUAAACGAGUGCGGGGUGUAGUGC---RGCUGGACUAGAAGCCUGC---AAUGGUACUGAUCCAGACCAUGUUAGUAGAGGUUUGA
HCoV 229E     UUUAAACGAGUCCGGGGUCUAGUGC---GGCUGGACUAGAGCCUGU---AAUGGUACAGACAUAGAUUACUGUGUCCGUGCGUUUGA
PEDV          UUUAAACGAGUACGGGGUCUAGUGC---RGCUGGACUAGAGCCUGU---AAUGGUACUGAUACACAACAUGUGUAUCGUGCGUUUGA
IBV           UUUAAACGGGUACGGGGUAGCAGUGA---GGCUGGCUGAURGCCCUUGCUAGUGGAUGUGAUCCUGAUGUUGUAAAGCGAGCGUUUGA
SARS          UUUAAACGGGUUUGGGCUGUAGUGC---RGCCGUCUACACGGGCGGCACAGGCACUAGUACUGAUGUCGUCUACAGAGCGUUUGA
MHV           UUUAAACGGGUUCGGGGUCAAGUGUAAAGGCCGUCUGGUACCGUGUCCAGUGGCUUGGACACUGAUGUUCAAUUAGGGCGUUUGA
BcoV          UUUAAACGGGUUCGGGGUACCAGUGUAGAGGCCGCGUCUGGUAGCCUGUGCCAGUGGUUUAUCUACUGAUGUACAAUUAAGGGCGUUUGA
```

Nucleotide residues conserved in coronaviruses are shown in bold type

| Shaded Region | Feature          | Pairing Mask Symbol |
|---------------|------------------|---------------------|
| A             | slippery sequence | *                   |
| B             | stem 1           | (                   |
| C             | stem 2           | [                   |
| D             | stem 1           | )                   |
| E             | stem 2           | ]                   |

U.S. PATENT DOCUMENTS

| | | |
|---|---|---|
| 5,801,154 A | 9/1998 | Baracchini et al. |
| 5,877,309 A * | 3/1999 | McKay et al. ............. 536/24.5 |
| 6,180,353 B1 * | 1/2001 | Dean et al. .................... 435/6 |

FOREIGN PATENT DOCUMENTS

| | | |
|---|---|---|
| WO | WO 95/27054 | 10/1995 |
| WO | WO 2004/092383 A2 | 10/2004 |

OTHER PUBLICATIONS

"WHO Multicenter Collaborative Networks For Severe Acute Respiratory Syndrome (SARS)," *Wkly. Epidemiol. Rec.*, 2003, 78<121-122.

Farabaugh, "Programmed translational frameshifting," *Microbiol. Rev.* (1996) 60:103-134.

Gesteland and Atkins, "Recoding: dynaming reprogramming of translation," *Ann. Rev. Biochem.* (1996) 65:741-768.

Giedroc, et al., "Structure, stability and function of RNA pseudoknots invoved in stimulating ribosomal frameshifting," *J. Mol. Biol.* (2000) 298:167-185.

Egli, et al., "Metal Ions and flexibility in a viral RNA pseudoknot at atomic resolution," *Proc. Natl. Acad. Sci. USA* (2002) 99:4302-4307.

Plant, et al., "The 9-A solution: how mRNA pseudoknots promote efficient programmed-1 ribosomal frameshifting," *RNA* (2003) 9:168-164.

Vickers and Ecker, "Enhancement of ribosomal frameshifting by oligonucleotides targeted to the HIV gag-pol region," *Nucleic. Acids Res.* (1992) 20:3945-3953.

Agrawal, S. et al., "Antisense therapeutics: is it as simple as complementary base recognition?" *Mol. Med. Today* (2000) 6:72-81.

Breierley, I. et al., "Expression of a Coronavirus Ribosomal Frameshift Signal in *Escherichia coli*: Influence of tRNA Anticodon Modification on Frameshifting," *J. Mol. Biol.* (1997) 270:360-373.

Qin, L. et al., "Identification of probably genomic packaging signal sequence from SARS-CoV genome bioinformatics analysis," *Acta Pharmacol. Sin* (2003) 24(6):489-496.

Shi, Y. et al., "Antisense downregulation of SARS-CoV gene expression in Vero E6 cells," *J. Gene Med.* (2005) 7:97-107.

Snijder, E. J. et al., "Unique and Conserved Features of Genome and Proteome of SARS-coronavirus, an Early Split-off From the Coronavirus Group 2 Lineage," *J. Mol. Bio.* (2003) 331:991-1004.

PCT International Search Report for PCT/US04/13050 dated Apr. 13, 2005.

Supplementary European Search Report from PCT/US2004/013050 dated Jan. 22, 2007.

Abdou, et al, "Beta-cyclodextrin derivatives as carries to enhance the antiviral activity of an antisense oligonucleotide directed toward a coronavirus intergenic consensus sequence", Archives of Virology, vol. 142, NR 8, pp. 1585-1602; XP002397673, (1997).

Drosten, et al, "Identification of a Novel Coronavirus in patients with severe acute respiratory syndrome" New England Journal of Medicine, Massachusetts Medical Society, vol. 348 No. 20, Apr. 10, 2003.

Philipkoski, Kristen "Stopping SARS: A search for drugs" Wired News, Apr. 28, 2003. http://wired.com/news/medtech/1.58635-0.html.

Ksiazek, et al., "A Novel Coronavirus associated with Severe acute respiratory syndrome" New England Journal of Medicine, Massachusetts Medical Society, Boston, MA vol. 348, No. 20, Apr. 10, 2003.

Marra, et al., "The Genome Sequence of the SARS-associated coronavirsu" Science, American Association for the Advancement of Science US vol. 300 No. 5624. pp. 1399-1404, May 30, 2003.

Rota, et al, "Characterization of a novel coronavirus associated with severe acute respiratory syndrome" Science American Association for the Advancement of Science, vol. 300, No. 5624, May 30, 2003. pp. 1394-1399.

Supplemental partial European Search Report for EP 04809344.7 mailed on Oct. 24, 2006.

* cited by examiner

FIGURE 1

```
pairing mask  *******-----((((((((((------[[[[((--))))))))))----------]]]]------
                      A              B            C          D                              E
TGEV      UUUAAACGAGUGCGGGGUCUAGUGC----AGCUCGACUAGAACCCUGC----AAUGGUACUGAUCCAGACCAUGUUAGUUAGAGCUUUGA
HCoV 229E UUUAAACGAGUCCGGGCCUCUAGUGC----CGGCUCGACUAGUCAGCCUGU----AAUGGUACAGAGACAUAGAUUACUGUUACUGCUUUGA
PEDV      UUUAAACGAGUACGGGCCUCUAGUGU----AGCUCGACUAGAACGGCCUGU----AAUGGUACACAACAUGGUAGUUACUGUAGCCUUUGA
IBV       UUUAAACGGGUACGGGUACUAGUGA----GCCUCGACCGUAUACAGGGCUUGCUAGUGCGGAUCCUAGAGCACCUGAUCUAGUUAAAGCUUUGA
SARS      UUUAAACGGGUUUGCGGUGUAAGUGC----AGCCCGUCUUACACCGUGCGGGACAGGCACCAGGUACUGAUGUCGUCAAUAGGGCUUUGA
MHV       UUUAAACGGGUACGGGUUUGUAGUGU----AGCUCUAUCUAUGGAGGUGCCUCGGUGUCCAGGUGCACUAGUGUUCAAUUAGGGUUUGA
BcoV      UUUAAACGGGUACGGGUUCGUAGUGU----AGCUGGUAAAAUGCGGUAGUAUGCCAGUGUCGUCAGGUUAUCAAUACUAGGUUUUGA
```

Nucleotide residues conserved in coronaviruses are shown in bold type

| Shaded Region | Feature | Pairing Mask Symbol |
|---|---|---|
| A | slippery sequence | * |
| B | stem 1 | ( |
| C | stem 2 | [ |
| D | stem 1 | ) |
| E | stem 2 | ] |

COMPOSITIONS AND METHODS FOR THE TREATMENT OF SEVERE ACUTE RESPIRATORY SYNDROME (SARS)

CROSS-REFERENCE TO RELATED APPLICATIONS

This application claims priority to: 1) U.S. provisional application Ser. No. 60/466,426 filed Apr. 28, 2003; 2) U.S. provisional application Ser. No. 60/468,562 filed May 6, 2003; 3) U.S. provisional application Ser. No. 60/467,770 filed Apr. 30, 2003; 4) U.S. provisional application Ser. No. 60/468,627 filed May 6, 2003; 5) U.S. provisional application Ser. No. 60/477,637 filed Jun. 10, 2003; 6) U.S. provisional application Ser. No. 60/483,579 filed Jun. 27, 2003; and 7) U.S. provisional application Ser. No. 60/565,370, filed Apr. 26, 2004, each of which is incorporated herein by reference in its entirety.

REFERENCE TO SEQUENCE LISTING SUBMITTED ON COMPACT DISK

An amended Sequence Listing is located on a separate replacement CD-R entitled "Copy 1 Replacement Sep. 02, 2004" in a file entitled "ISIS0083-100rev.SEQ.txt", created Sep. 2, 2004, containing 8.33 Mb, and is incorporated herein by reference in its entirety. The total number of compact disks, including duplicates (i.e., "Copy 2 Replacement Sep. 02, 2004"), submitted herewith is two, and there is one file on each of the submitted compact disks.

FIELD OF THE INVENTION

This invention relates to the design and synthesis of oligomeric compounds and compositions that can be administered to reduce the activity of SARS virus in vivo or in vitro, to prevent or treat SARS virus-associated disease, to detect SARS virus, and to diagnose SARS virus-associated diseases.

BACKGROUND OF THE INVENTION

The Coronaviridae is the family of viruses that infect humans and animals, and includes a species of virus that causes a common cold-like respiratory illness known as Human Coronavirus 229E (HCo-V-229E). Also included in this family are an avian infectious bronchitis virus (IBV), murine hepatitis virus (MHV), porcine transmissible gastroenteritis virus PRCoV, porcine respiratory coronavirus and bovine coronavirus, among others (Lai and Holmes, Chapter 35 in the virus book).

Coronaviruses are large, enveloped, plus-stranded RNA viruses. They cause the common cold in all age groups accounting for approximately 15% of all colds. Coronaviruses have been implicated in the etiology of gastrointestinal disease in infants. They also cause economically important diseases in animals (e.g. avian infectious bronchitis and porcine transmissible gastroenteritis). Coronaviruses get their name because in electron micrographs the envelope glycoproteins appear to form a halo or corona around the periphery of the virion. The coronaviruses are also interesting because they are the only plus-strand RNA viruses with a helical nucleocapsid.

Coronaviruses have the largest genomes of all RNA viruses and replicate by a unique mechanism which results in a high frequency of recombination. Virions mature by budding at intracellular membranes, and infection with some coronaviruses induces cell fusion (Fields Virology, D. M. Knipe, P. M. Howley Eds. 2001, Lippincott Williams & Wilkins, Publishers, Philadelphia, 1163-1179).

Human coronaviruses grow poorly in culture and cannot be analyzed in detail. Most studies are carried out with mouse hepatitis virus, a coronavirus that grows well in culture and is related to human strain OC43. Infection begins when the virus recognizes a cell surface receptor found to be aminopeptidase N for strain 229E and sialic acid for OC43. The virus enters the cell by endocytosis and membrane fusion.

As with most RNA viruses, coronavirus replication takes place entirely in the cytoplasm. Once the viral RNA enters the cytoplasm it is translated to produce the viral RNA-dependent RNA polymerase which then makes a full-length complementary (minus strand) copy of the virion RNA. The minus strand serves a template for transcription of the seven capped and polyadenylated mRNAs. These are arranged as a nested set in which all have the same 3' end but each is smaller by one gene than the next larger one. All have the same 5' end, a 72 nucleotide leader sequence, encoded only at the 5' end of the genome RNA. This suggests each mRNA is transcribed by a mechanism in which transcription starts by synthesizing the leader sequence and then "skips" to the beginning of one of the genes with each mRNA ending at the same 3' end. Only the first gene (the one closest to the 5' end) is translated on each mRNA regardless of how many genes are present. Thus, there is no polyprotein processing in coronavirus replication.

Coronaviruses are a major cause of common colds in the winter months. The virus is found throughout the world. Antibodies begin to appear in childhood, and are found in more than 90% of adults. The frequency of coronavirus respiratory infections is highly variable from year to year. The highest incidence occurs in years when rhinovirus colds are lowest. Coronavirus colds tend to occur in defined outbreaks. Laboratory diagnosis is by ELISA, complement fixation or hemagglutination tests. Human coronaviruses cannot be isolated by growth in culture.

Colds due to coronaviruses cannot be distinguished clinically from rhinovirus colds. The incubation period is 2-5 days and symptoms last 5-7 days. Immunity is directed to the major virus surface glycoprotein, E2. Reinfection may last for several years although reinfection is common probably because of the high level of virus genetic recombination.

Coronaviruses are transmitted by aerosols of respiratory secretions, by the fecal-oral route, and by mechanical transmission. Most virus growth occurs in epithelial cells. Occasionally the liver, kidneys, heart or eyes may be infected, as well as other cell types such as macrophages. In cold-type respiratory infections, growth appears to be localized to the epithelium of the upper respiratory tract, but there is currently no adequate animal model for the human respiratory coronaviruses. Clinically, most infections cause a mild, self-limited disease (classical "cold" or upset stomach), but there may be rare neurological complications.

In late 2002, several hundred cases of an atypical pneumonia were reported in Guangdong Province of the People's Republic of China. Months later, similar cases were identified in Canada, Vietnam and Hong Kong. The World Health Organization (WHO) identified the emergent disease as "severe acute respiratory syndrome" or SARS. In March 2003, a novel coronavirus (SARS-CoV) was discovered in association with cases of SARS. By late April 2003, over 4300 SARS cases, resulting in about 250 deaths, were reported from 25 countries globally. The SARS virus is believed to be spread by droplets produced by coughing and sneezing, but other routes of infection may also be involved, such as contamination of objects by the hands. As of May 7, 2003, the WHO estimates SARS case fatality to be 14-15%. As of Jun. 3, 2003 the total number of worldwide cases of SARS reported by WHO is 8398.

It is now possible to generally describe the course of the disease. The incubation period following initial infection is about 2 to 7 days. The infection is generally characterized by fever, which is followed in the next few days by dry, non-productive cough and shortness of breath. The disease results in death in about 3 to 10% of cases.

The complete genome of SARS-CoV has been identified, as well as common variants thereof The genome of SARS-CoV is a 29,727-nucleotide polyadenylated RNA, has 11 open reading frames, and 41% of the residues are G or C. The genomic organization is typical of coronaviruses, with the characteristic gene order (5'-replicase (rep), spike (S), envelope (E), membrane (M), nucleocapsid (N)-3' and short untranslated regions at both termini. The SARS-CoV rep gene, which comprises about two-thirds of the genome, is predicted to encode two polyproteins that undergo co-translational proteolytic processing. There are four open reading frames (ORFs) downstream of rep that are predicted to encode the structural proteins, S, E, M and N, which are common to all known coronaviruses. The hemagglutinin-esterase gene, which is present between ORF1b and S in group 2 and some group 3 coronaviruses was not found. Phylogenetic analyses and sequence comparisons showed that SARS-CoV is not closely related to any of the previously characterized coronaviruses.

Coronaviurses also encode a number of non-structural proteins that are located between S and E, between M and N, or downstream of N. These non-structural proteins, which vary widely among the different coronavirus species, are of unknown function and are dispensable for virus replication.

Diagnostic tests are now available, but all have limitations as tools for bringing an outbreak quickly under control. An ELISA test detects antibodies reliably but only from about day 20 after the onset of clinical symptoms. It therefore cannot be used to detect cases at an early stage prior to spread of the infection to others. The second test, an immunofluorescence assay (IFA), detects antibodies reliably as of day 10 of infection. It shares the defect of the ELISA test in that test subjects have become infective prior to IFA-based diagnosis. Moreover, the IFA test is a demanding and comparatively slow test that requires the growth of virus in cell culture. The third test is a polymerase chain reaction (PCR) molecular test for detection of SARS virus genetic material is useful in the early stages of infection but undesirably produces false-negatives. Thus the PCR test may fail to detect persons who actually carry the virus, even in conjunction with clinical diagnostic evaluation, creating a dangerous sense of false security in the face of a potential epidemic of a virus that is known to spread easily in close person-to-person contact (WHO. Severe acute respiratory syndrome (SARS). *Wkly Epidemiol. Rec.*, 2003, 78, 121-122).

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure which amplifies a specific target DNA sequence based on the flanking primers used. Finally, detection and data analysis convert the hybridization event into an analytical result.

Other techniques for detection of bioagents include high-resolution mass spectrometry (MS), low-resolution MS, fluorescence, radioiodination, DNA chips and antibody techniques. None of these techniques is entirely satisfactory.

Mass spectrometry provides detailed information about the molecules being analyzed, including high mass accuracy. It is also a process that can be easily automated. However, high-resolution MS alone fails to perform against unknown or bioengineered agents, or in environments where there is a high background level of bioagents ("cluttered" background). Low-resolution MS can fail to detect some known agents, if their spectral lines are sufficiently weak or sufficiently close to those from other living organisms in the sample. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.*, 1996, 7, 1266-1269; Muddiman et al., *Anal. Chem.*, 1997, 69, 1543-1549; Wunschel et al., *Anal. Chem.*, 1998, 70, 1203-1207; and Muddiman et al., *Rev. Anal. Chem.*, 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.*, 1996, 10, 377-382). The use of matrix-assisted laser desorption ionization-time of flight (MALDI-TOF) mass spectrometry for characterization of PCR products has been described. (Muddiman et al., *Rapid Commun. Mass Spec.*, 1999, 13, 1201-1204). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by nonrandomly fragmenting the target into a set of single-stranded nonrandom length fragments and determining their masses by MS.

U.S. Pat. Nos. 5,547,835, 5,605,798, 6,043,031, 6,197,498, 6,221,601, 6,221,605, 6,277,573, 6,235,478, 6,258,538, 6,300,076, 6,428,955 and 6,500,621, describe fast and highly accurate mass spectrometer-based processes for detecting the presence of a particular nucleic acid in a biological sample for diagnostic purposes.

WO 98/21066 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 describe methods of sequencing nucleic acids using mass spectrometry. U.S. Pat. Nos. 5,622,824, 5,872,003 and 5,691,141 describe methods, systems and kits for exonuclease-mediated mass spectrometric sequencing.

Programmed ribosomal frameshifting is used by viruses (including all retroviruses), DNA insertion sequences, bacteria, and yeast (Farabaugh, *Microbiol. Rev.*, 1996, 60, 103-134; and Gesteland et al., *Annu. Rev. Biochem.*, 1996, 65, 741-768), and is an essential mechanism for regulating the relative expression of proteins that are encoded in two overlapping translational reading frames. The shift occurs at a heptanucleotide of general sequence X XXY YYN which is known as a "slippery site" (Giedroc et al., *J. Mol. Biol.*, 2000, 298, 167-185). An mRNA pseudoknot induces elongating ribosomes to pause with their A- and P-site tRNAs positioned over the slippery site. While paused at the slippery site, if the ribosome shifts by 1 base in the 5' direction, the non-wobble bases of both the A- and P-site tRNAs can bind with the new −1 frame codons to make the protein in the −1 frame XXX YYY N as the mRNA pseudoknot is denatured and elongation continues in the new reading frame.

The efficiency of frameshifting depends on the nature of the slippery site, as well as the sequence and complexity of the downstream pseudoknot motif (Egli et al., *Proc. Natl. Acad. Sci.*, 2002, 99, 4302-4307). Thermodynamic or kinetic control of pseudoknot unfolding may be important in regulating the efficiency of ribosomal frameshifting (Giedroc et al., *J. Mol. Biol.*, 2000, 298, 167-185).

Movement of 9 Å by the anticodon loop of the aminoacyl-tRNA at the accommodation step normally pulls the downstream mRNA a similar distance along with it. Plant et al. have suggested that the downstream mRNA pseudoknot provides resistance to this movement by becoming wedged into the entrance of the ribosomal mRNA tunnel. These two opposing forces result in the creation of a local region of tension in the mRNA between the A-site codon and the mRNA pseudoknot. This can be relieved by one of two mechanisms; unwinding the pseudoknot, allowing the downstream region to move forward, or by slippage of the proximal region of the mRNA backwards by one base. The observed result of the latter mechanism is a net shift of reading frame by one base in the 5' direction, that is, a −1 ribosomal frameshift (Plant et al., *RNA*, 2003, 9, 168-174).

Ribosomal frameshifting has been documented as an essential feature in a number of viruses. These include the retroviruses (such as HIV), the Coronaviridae, Astroviridae, Totiviridae, among other families of viruses.

The frameshift site in coronaviruses is in between ORFs 1a and 1b. ORF 1a contains a number of proteins, including proteases, and ORF 1b contains the RNA-dependent-RNA-polymerase.

The RNA-dependent-RNA-polymerase is an essential gene. Unlike some other RNA-genome viruses, coronaviruses do not carry a copy of the RNA-dependent-RNA-polymerase in the virion particle. Therefore, to succeed in replicating, the RNA-dependent-RNA-polymerase must be translated directly from the genomic RNA. Since the RNA-dependent-RNA-polymerase is located downstream of the frameshift site, it is absolutely required that the frameshift signal work in order to produce the coronavirus RNA-dependent-RNA-polymerase, which is −1 out of frame with respect to the upstream ORF 1a.

If the SARS virus behaves the same way as the previously documented coronaviruses, it will have frameshift site in a similar position of the genome, and the function of the frameshift site will be essential to the life cycle of the virus.

Thus, modulation of the frameshifting process is expected to provide a useful strategy with which to disrupt the translation of the RNA-dependent-RNA-polymerase which is essential for the propagation of SARS-CoV.

Previous attempts to modulate ribosomal frameshifting of viral RNA have been limited to investigations of the Human immunodeficiency virus (HIV). For example, disclosed and claimed in U.S. Pat. No. 5,707,866 and PCT publication WO 95/27054 are methods and compositions for inhibition of HIV ribosomal frameshifting with antisense DNA oligomers complementary to regions of the RNA of the small ribosomal subunit of mammalian cells which are involved in the control of translation fidelity (Brakier-Gingras, 1998).

Vickers and Ecker have reported enhancement of ribosomal frameshifting by oligonucleotides targeted to the HIV gag-pol region (Vickers et al., *Nucleic Acids Research*, 1992, 20, 3945-3953).

While it is currently believed that SARS-CoV is the primary etiological agent for SARS, it is not known whether other infective agents, such as viruses, may be responsible for higher virulence, morbidity and/or mortality rates. There may also be a genetic component to morbidity and mortality, at it has been shown in some cases that related patients seem to have similar clinical outcomes. While these possibilities cannot be ruled out, it is accepted that reducing viral load in the lungs will correlate with improved prognosis.

A well studied frameshift site is the Infectious Bronchitis Virus, a coronavirus that infects chickens. The structure of the IBV virus is a slippery site followed by a pseudoknot.

Oligomeric compounds which hybridize to RNA of the frameshift site will provide a useful strategy with which to modulate the function of the frameshift site and provide a basis for discovery of antiviral drugs for viruses such as the coronaviruses which are causally-linked to SARS. Additionally, it is expected that small molecules which specifically bind to RNA regions of specific secondary structure will also provide a means of modulation of ribosomal frameshifting.

The present invention provides methods and compositions for modulation of ribosomal frameshifting, including the frameshifting occurring in the RNA of coronaviruses such as SARS-linked coronaviruses.

Nucleosides and their derivatives have been used successfully in treatment of some viral infections, however to date no effective antiviral therapy has been identified for SARS, especially in the late stages.

Antisense agents, such as antisense oligonucleotides, PNAs, LNAs and morpholinos have been used to treat a variety of disease states. The first FDA-approved antisense drug is a phosphorothioate oligonucleotide (Vitravene®, fomivirsen) available through Isis Pharmaceuticals, Inc., Carlsbad, Calif. Fomivirsen is an antiviral antisense compound effective for treating CMV retinitis. It has been theorized to treat other viruses, e.g. hepatitis C, with antisense drugs, however it has not been previously suggested to treat coronaviruses, and especially SARS-CoV by inhalation of one or more antiviral compounds.

Methods of delivering drugs by pulmonary administration have been described. For example, each of U.S. Pat. Nos. 6,550,472, 6,546,927, 6,543,443, 6,540,154, 6,540,153, 6,467,476 and 6,427,682 teaches methods and devices useful in the pulmonary administration of drugs, and each is specifically incorporated herein by reference, however none has demonstrated successful treatment of SARS by inhalation therapy. Also, each of U.S. Pat. Nos. 6,503,480, 6,447,753, 6,387,390, 5,985,320, 5,985,309 and 5,855,913 teaches methods and devices useful in the pulmonary administration of drugs, and each is specifically incorporated herein by reference, however none has demonstrated successful treatment of SARS by inhalation therapy. In addition, each of U.S. Pat. Nos. 6,431,167, 6,408,854, 6,349,719, 6,167,880, 6,098,620, 5,971,951, 5,957,124, 5,906,202, 5,819,726, 5,755,218, and 5,522,385 teaches methods and devices useful in the pulmonary administration of drugs, and each is specifically incorporated herein by reference, however none has demonstrated successful treatment of SARS by inhalation therapy. Likewise, each of U.S. Pat. Nos. 6,546,929, 6,543,448, 6,509,006, 6,423,344, 6,303,582, and 6,138,668 teach methods of delivering drug to the lung, and each is specifically incorporated herein by reference, however none has demonstrated successful treatment of SARS by inhalation therapy.

Methods of delivering medicaments by nasal instillation have been described. For example, U.S. Pat. Nos. 6,551,578, 6,554,497, 6,485,707, 6,468,507, 6,464,959, 6,294,153, 6,214,805, 6,087,343, 5,985,320, and 5,744,166, each of which is expressly incorporated herein by reference, disclose compositions and methods for intranasal instillation of drug compositions.

Bioadhesives have been described for facilitating transport of medicaments across endothelial mucosa. For example, U.S. Pat. No. 6,228,383, incorporated herein in its entirety, teaches use of bioadhesive fatty acid esters for facilitating transport of drug substances across mucosa in the lung, nose and other tissues.

Penetration enhancers have been described in U.S. patent application Ser. No. 09/315,298, filed on May. 20, 1999 and incorporated herein by reference. Penetration enhancers facilitate the penetration of mucosa, including pulmonary and nasal mucosa.

Oligomeric compounds which hybridize to RNA of the frameshift site will provide a useful strategy with which to modulate the function of the frameshift site and provide a basis for discovery of antiviral drugs for viruses such as the coronaviruses which are causally-linked to SARS. Additionally, it is expected that small molecules which specifically bind to RNA regions of specific secondary structure will also provide a means of modulation of ribosomal frameshifting.

Thus, there is a need for a method for bioagent detection and identification which is both specific and rapid, and in which nucleic acid sequencing is not absolutely required in order to achieve the desired detection or identification. This need is particularly acute for novel infectious agents such as the SARS-CoV that spread rapidly and that may complicate traditional detection methods by mutating over relatively short periods of time.

The present invention provides methods and compositions for modulation of ribosomal frameshifting, including the frameshifting occurring in the RNA of coronaviruses such as SARS-linked coronaviruses, and addresses the need for rapid identification of bioagents, including the SARS coronavirus, which is a major health threat.

SUMMARY OF THE INVENTION

The present invention provides oligomeric compounds comprising from 8 to about 80 nucleobases targeted to a nucleic acid molecule encoding SARS virus, wherein the compound hybridizes with the nucleic acid molecule encoding SARS virus and reduces the expression of SARS virus by at least 50%. In some embodiments, the compound comprises from 12 to about 50 nucleobases or from 15 to about 30 nucleobases. In some embodiments, the compound is an oligonucleotide, an antisense oligonucleotide, a DNA oligonucleotide, an RNA oligonueleotide, or a chimeric oligonucleotide. In some embodiments, at least a portion of the compound hybridizes with RNA to form an oligonucleotide-RNA duplex. In some embodiments, the compound has at least 70%, at least 80%, at least 90%, or at least 95% complementarity with the nucleic acid molecule encoding SARS virus. In some embodiments, the compound comprises at least one modified internucleoside linkage, modified sugar moiety, or modified nucleobase. In some embodiments, the compound comprises at least one 2'-O-methoxyethyl sugar moiety, at least one phosphorothioate internucleoside linkage, or at least one 5-methylcytosine.

The present invention also provides methods of reducing the expression of a SARS virus in cells or tissues comprising contacting the cells or tissues with a compound described herein so that expression of SARS virus is reduced.

The present invention also provides methods of screening for a modulator of a SARS virus comprising contacting a suitable target region of a nucleic acid molecule encoding a SARS virus with one or more candidate modulators of SARS virus, and identifying one or more modulators of SARS virus expression that modulate the expression of the SARS virus.

The present invention also provides diagnostic methods for identifying a disease state comprising identifying the presence of a SARS virus in a sample using at least one primer.

The present invention also provides kits and assay devices comprising a compound described herein.

The present invention also provides methods of treating an animal having a disease or condition associated with a SARS virus comprising administering to the animal a therapeutically or prophylactically effective amount of a compound described herein so that expression of SARS virus is reduced. In some embodiments, the disease or condition is a viral infection.

The present invention also provides compounds 8 to 80 nucleobases in length targeted to a frameshift site of viral RNA, wherein the compound specifically hybridizes with the frameshift site and modulates the process of ribosomal frameshifting of the viral RNA.

The present invention also provides methods of screening for a modulator of a frameshift site by contacting a suitable target segment of a frameshift site with one or more candidate modulators of the frameshift site and measuring the extent of frameshift modulation.

The present invention also provides methods of treating an individual having a disease or condition associated with a coronavirus by administering to the individual a therapeutically or prophylactically effective amount of a compound targeting a frameshift site of a coronavirus so that the propagation of the coronavirus is inhibited as a result of modulation of the frameshift site.

The present invention also provides methods of characterization of a previously uncharacterized frameshift site in a coronavirus RNA by obtaining RNA sequences of known coronaviruses with known frameshift sites, obtaining an RNA sequence of a coronavirus with an uncharacterized frameshift site, and performing covariance analysis on multiple sequence alignments of the RNA sequences of known coronaviruses and the RNA sequence of the coronavirus with an uncharacterized frameshift site.

BRIEF DESCRIPTION OF THE DRAWINGS

FIG. 1 represents an alignment sequence segments of frameshift sites of transmissible gastroenteritis virus (TGEV) (SEQ ID NO: 30064), human coronavirus 229E (HcoV 229E) (SEQ ID NO: 30065), porcine epidemic diarrhea virus (PEDV) (SEQ ID NO: 30066); Avian infectious bronchitis virus (IBV) (SEQ ID NO: 30067); SARS coronavirus (SARS) (SEQ ID NO: 30068); Murine hepatitis virus (MHV) (SEQ ID NO: 30069) and Bovine coronavirus (BcoV) (SEQ ID NO: 30070). Also shown for the alignment are pairing mask symbols corresponding to the slippery sequence, stem 1, and stem 2 represented by shaded regions in the alignment. Nucleotide residues conserved in coronaviruses are shown in bold type.

DESCRIPTION OF EMBODIMENTS

The present invention employs compounds, such as oligomeric compounds, including, for example, oligonucleotides and similar species, for use in modulating the function or effect of nucleic acid molecules encoding SARS virus. This is accomplished by, for example, providing oligonucleotides that hybridize with one or more nucleic acid molecules encoding SARS virus. As used herein, the terms "target nucleic acid" and "nucleic acid molecule encoding SARS virus" have been used for convenience to encompass DNA encoding SARS virus, RNA (including pre-mRNA and mRNA or portions thereof) transcribed from such DNA, and also cDNA derived from such RNA. The hybridization of a compound of this invention with its target nucleic acid is generally referred to as "antisense." Consequently, one mechanism believed to be included in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is suitable to target specific nucleic acid molecules and their functions for such antisense inhibition.

The functions of DNA to be interfered with include, but are not limited to, replication and transcription. Replication and transcription, for example, can be from an endogenous cellular template, a vector, a plasmid construct or otherwise. The functions of RNA to be interfered include, but are not limited to, functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of SARS virus. In the context of the present invention, "modulation" and "modulation of expression" mean either an increase (stimulation) or a decrease (inhibition or reduction) in the amount or levels of a nucleic acid molecule encoding the gene, e.g., DNA or RNA. Inhibition or reduction are often the desired form of modulation of expression and mRNA is often a desired target nucleic acid.

In the context of this invention, "hybridization" means the pairing of complementary strands of oligomeric compounds. One mechanism of pairing involves hydrogen bonding, which may be Watson-Crick, Hoogsteen, or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound, such as an antisense compound, is "specifically hybridizable" when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays. The oligomeric compounds of the invention, however, need not be specifically hybridizable to possess value (i.e., the oligomeric compound may, in fact, possess non-specific binding to non-target nucleic acid sequences under conditions in which specific binding is desired).

In the present invention, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound and its corresponding target molecule. For example, if a nucleobase at a particular position of an oligonucleotide (an oligomeric compound) is capable of hydrogen bonding with a nucleobase at a particular position of a target nucleic acid molecule (the target nucleic acid being a DNA, RNA, or oligonucleotide molecule), then the position of hydrogen bonding between the oligonucleotide and the target nucleic acid molecule is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid molecule.

It is understood in the art that the sequence of an oligomeric compound need not be 100% complementary to that of its target nucleic acid molecule to be specifically hybridizable or hybridizable. Moreover, an oligonucleotide may hybridize over one or more segments such that intervening or adjacent segments are not involved in the hybridization event (e.g., a loop structure or hairpin structure). The oligomeric compounds of the present invention can comprise at least 70%, at least 80%, at least 90%, at least 95%, at least 99%, or 100% sequence complementarity to a target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would, thus, fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

Compounds of the Invention

According to the present invention, oligomeric compounds include, but are not limited to, antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular, or hairpin oligomeric compounds and may contain structural elements such as internal or terminal bulges or loops. Additionally, the compound may have regions of single-strandedness and regions of double-strandedness. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes. 2-5A-dependent RNase is a component of the interferon-regulated 2-5A system that functions in the antiviral and antiproliferative roles of interferons. Treatment of cells with interferon results in enhanced levels of both 2-5A-dependent RNase and a group of synthetases that produce 5-prime-triphosphorylated, 2-prime,5-prime-oligoadenylates (2-5A) from ATP. The role of the 2-5A system in the control of viral and cellular growth suggests that defects in the 2-5A-dependent RNase gene could result in reduced immunity to virus infections and cancer.

While one form of an oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, Cell, 1995, 81, 611-620). Montgomery et al. have shown that the primary interference effects of dsRNA are posttranscriptional (Montgomery et al., Proc. Natl. Acad. Sci. USA, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). Recently, it has been shown that it is, in fact, the single-stranded oligomers of antisense polarity of the dsRNAs which are the potent inducers of RNAi (Tijsterman et al., Science, 2002, 295, 694-697).

While oligonucleotides are a suitable form of the compounds of this invention, the present invention comprehends other families of compounds as well, including but not limited to, oligonucleotide analogs and mimetics such as those described herein.

The compounds in accordance with this invention can comprise from about 8 to about 80 nucleobases (i.e. from about 8 to about 80 linked nucleosides). As used herein, the term "about" means ±5% of the value it modifies (rounded up to the nearest whole number if a nucleobase is the term which is modified). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the compounds of the invention are from 12 to about 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the compounds of the invention are from 15 to about 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In other embodiments, the antisense compounds are from 8 to about 80 nucleobases in length comprising a stretch of at least eight (8) consecutive nucleobases selected from within the illustrative antisense compounds. Exemplary antisense compounds include, but are not limited to, oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly suitable antisense compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the antisense compounds illustrated herein will be able, without undue experimentation, to identify further suitable antisense compounds.

Targets of the Invention

"Targeting" an oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a SARS virus.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller portions or subportions of regions within a target nucleic acid. "Sites," as used in the present invention, are defined as positions within a target nucleic acid.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding SARS virus, regardless of the sequence(s) of such codons.

It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligomeric compounds of the present invention.

The open reading frame (ORF) or "coding region," which is known in the art to refer to the region between the translation initiation codon and the translation termination codon, is also a region which may be targeted effectively. Within the context of the present invention, a suitable region is the intragenic region encompassing the translation initiation or termination codon of the open reading frame (ORF) of a gene.

Other target regions include, but are not limited to, the 5' untranslated region (5' UTR), known in the art to refer to the portion of an mRNA in the 5' direction from the translation initiation codon and, thus, including nucleotides between the 5' cap site and the translation initiation codon of an mRNA (or corresponding nucleotides on the gene), and the 3' untranslated region (3' UTR), known in the art to refer to the portion of an mRNA in the 3' direction from the translation termination codon and, thus, including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and, therefore, translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts." It is also known that introns can be effectively targeted using oligomeric compounds targeted to, for example, DNA or pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant produces a unique mRNA variant as a result of splicing. These mRNA variants are also known as "alternative splice variants." If no splicing of the pre-mRNA variant occurs, then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the oligomeric compounds hybridize are hereinbelow referred to as "suitable target segments." As used herein, the term "suitable target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

While the specific sequences of particular suitable target segments are set forth herein, one of skill in the art will recognize that these serve to illustrate and describe particular embodiments within the scope of the present invention. Additional suitable target segments may be identified by one having ordinary skill using the same type of methodology as disclosed herein.

Target regions or segments from 8 to about 80 nucleobases in length comprising a stretch of at least eight (8) consecutive nucleobases selected from within the illustrative suitable target segments or regions are considered to be suitable for targeting as well.

Target segments or regions can include DNA or RNA sequences that comprise at least the 8 consecutive nucleobases from the 5'-terminus of one of the illustrative suitable target segments or regions (the remaining nucleobases being a consecutive stretch of the same DNA or RNA beginning immediately upstream of the 5'-terminus of the target segment or region and continuing until the DNA or RNA contains from 8 to about 80 nucleobases). Similarly suitable target segments or regions are represented by DNA or RNA sequences that comprise at least the 8 consecutive nucleobases from the 3'-terminus of one of the illustrative suitable target segments or regions (the remaining nucleobases being a consecutive stretch of the same DNA or RNA beginning immediately downstream of the 3'-terminus of the target segment or region and continuing until the DNA or RNA contains from 8 to about 80 nucleobases). One having skill in the art armed with the suitable target segments or regions illustrated herein will be able, without undue experimentation, to identify additional suitable target segments or regions.

Once one or more target regions, segments or sites have been identified, oligomeric compounds are chosen which are sufficiently complementary to the target, i.e., hybridize sufficiently well and with sufficient specificity, to give the desired effect.

Screening and Target Validation

In a further embodiment, the "suitable target segments" or "suitable target regions" identified herein may be employed in a screen for additional compounds that modulate the expression of a SARS virus. "Modulators" are those compounds that decrease or increase the expression of a nucleic acid molecule encoding a SARS virus and which comprise at least an 8-nucleobase portion which is complementary to a suitable target segment or region. In one embodiment, the screening method comprises contacting a suitable target segment of a nucleic acid molecule encoding a SARS virus with one or more candidate modulators, and selecting for one or more candidate modulators which decrease or increase the expression of a nucleic acid molecule encoding a SARS virus. Once it is shown that the candidate modulator or modulators are capable of modulating (e.g. either decreasing or increasing) the expression of a nucleic acid molecule encoding a SARS virus, the modulator may then be employed in further investigative studies of the function of a SARS virus, or for use as a research, diagnostic, or therapeutic agent in accordance with the present invention.

The suitable target segments or regions of the present invention may be also be combined with their respective complementary oligomeric compounds of the present invention to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The compounds of the present invention can also be applied in the areas of drug discovery and target validation. The present invention comprehends the use of the compounds and suitable target segments or regions identified herein in drug discovery efforts to elucidate relationships that exist between a SARS virus and a disease state, phenotype, or condition. These methods include, but are not limited to, detecting or modulating a SARS virus comprising contacting a sample, tissue, cell, or organism with a compound of the present invention, measuring or detecting the nucleic acid or protein level of a SARS virus and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of suitable oligomeric compounds useful in this invention include, but are not limited to, oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that particular oligomeric compounds of the invention can also have one or more modified internucleoside linkages. A suitable phosphorus containing modified internucleoside linkage is the phosphorothioate internucleoside linkage.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

Representative United States patents that teach the preparation of the above phosphorus-containing linkages include, but are not limited to: U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697; and 5,625,050, certain of which are commonly owned with this application, and each of which is incorporated herein by reference in its entirety.

In some embodiments of the invention, oligomeric compounds have one or more phosphorothioate and/or heteroatom internucleoside linkages, in particular $—CH_2—NH—O—CH_2—$, $—CH_2—N(CH_3)—O—CH_2—$ (known as a methylene (methylimino) or MMI backbone), $—CH_2—O—N(CH_3)—CH_2—$, $—CH_2—N(CH_3)—N(CH_3)—CH_2—$ and $—O—N(CH_3)—CH_2—CH_2—$ (wherein the native phosphodiester internucleotide linkage is represented as $—O—P(=O)(OH)—O—CH_2—$). The MMI type internucleoside linkages are disclosed in the above referenced U.S. Pat. No. 5,489,677. Suitable amide internucleoside linkages are disclosed in the above referenced U.S. Pat. No. 5,602,240. Also suitable are oligonucleotides having morpholino backbone structures of the above-referenced U.S. Pat. No. 5,034,506.

Suitable modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to: U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269; and 5,677,439, certain of which are commonly owned with this application, and each of which is incorporated herein by reference in its entirety.

Mimetics

Another group of oligomeric compounds amenable to the present invention includes oligonucleotide mimetics. The term "mimetic" as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA oligomeric compounds include, but are not limited to: U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties, is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that teach the preparation of PNA compounds include, but are not limited to: U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

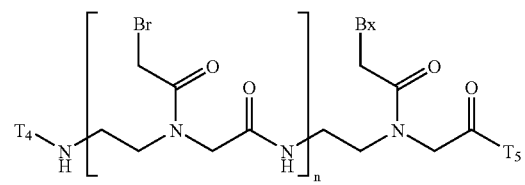

wherein
Bx is a heterocyclic base moiety;
$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the a-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;
$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;
$Z_1$ is hydrogen, $C_1$-$C_6$ alkyl, or an amino protecting group;
$Z_2$ is hydrogen, $C_1$-$C_6$ alkyl, an amino protecting group, —C(=O)—(CH$_2$)$_n$-J-$Z_3$, a D or L α-amino acid linked via the a-carboxyl group or optionally through the co-carboxyl group when the amino acid is aspartic acid or glutamic acid or a peptide derived from D, L or mixed D and L amino acids linked through a carboxyl group;
$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;
each J is O, S or NH;
$R_5$ is a carbonyl protecting group; and
n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

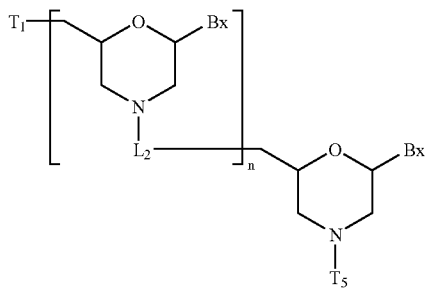

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

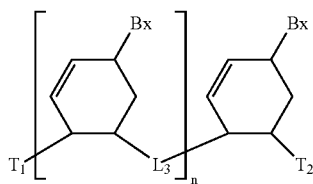

wherein each Bx is a heterocyclic base moiety;

$T_1$ is hydroxyl or a protected hydroxyl; and $T_2$ is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

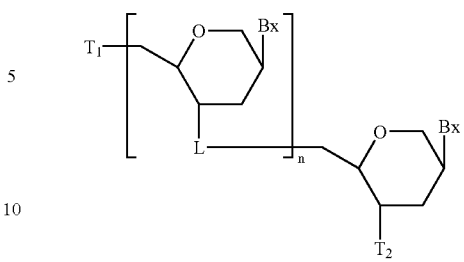

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

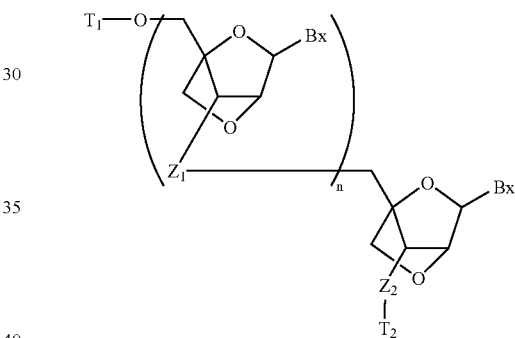

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

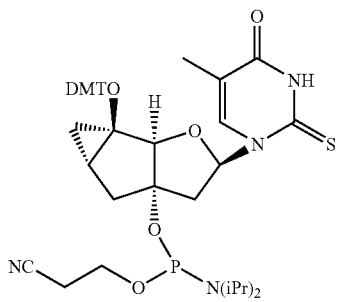

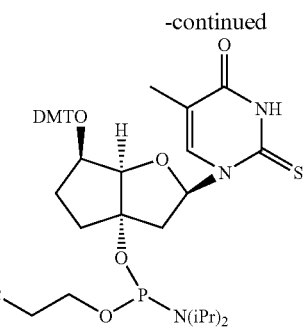

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleozides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

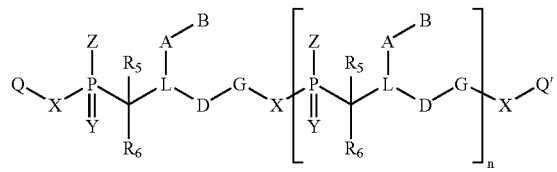

Another oligonucleotide mimetic has been reported wherein the furanosyl ring has been replaced by a cyclobutyl moiety.

Modified Sugars

Oligomeric compounds of the invention may also contain one or more substituted sugar moieties. Suitable oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486-504) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—OCH$_2$CH$_2$CH$_2$NH$_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to: U.S. Pat. Nos. 4,981,957; 5,118,800; 5,319,080; 5,359,044; 5,393,878; 5,446,137; 5,466,786; 5,514,785; 5,519,134; 5,567.811; 5,576,427; 5,591,722; 5,597,909; 5,610,300; 5,627,053; 5,639,873; 5,646,265; 5,658.873; 5,670,633; 5,792,747; and 5,700,920, certain of which are commonly owned with the instant application, and each of which is herein incorporated by reference in its entirety.

Further representative sugar substituent groups include groups of formula I$_a$ or II$_a$:

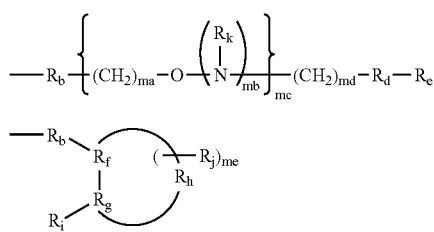

wherein:

R$_b$ is O, S or NH;

R$_d$ is a single bond, O, S or C(═O);

R$_e$ is C$_1$-C$_{10}$ alkyl, N(R$_k$)(R$_m$), N(R$_k$)(R$_n$), N═C(R$_p$)(R$_p$), N═C(R$_p$)(R$_r$) or has formula III$_a$;

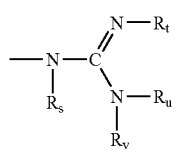

R$_p$ and R$_q$ are each independently hydrogen or C$_1$-C$_{10}$ alkyl;

R$_r$ is —R$_x$—R$_y$;

each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;

each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

R$_k$ is hydrogen, a nitrogen protecting group or —R$_x$—R$_y$;

R$_p$ is hydrogen, a nitrogen protecting group or —R$_x$—R$_y$;

R$_x$ is a bond or a linking moiety;

R$_y$ is a chemical functional group, a conjugate group or a solid support medium;

each R$_m$ and R$_n$ is, independently, H, a nitrogen protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$)(R$_v$) guanidino and acyl where said acyl is an acid amide or an ester;

or R$_m$ and R$_n$, together, are a nitrogen protecting group, are joined in a ring structure that optionally includes an additional heteroatom selected from N and O or are a chemical functional group;

R$_i$ is OR$_z$, SR$_z$, or N(R$_z$)$_2$;

each R$_z$ is, independently, H, C$_1$-C$_8$ alkyl, C$_1$-C$_8$ haloalkyl, C(═NH)N(H)R$_u$, C(═O)N(H)R$_u$ or OC(═O)N(H)R$_u$;

R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$)(R$_m$) OR$_k$, halo, SR$_k$ or CN;

m$_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Suitable sugar substituent groups include $O((CH_2)_nO)_m$ $CH_3$, $O(CH_2)_nOCH_3$, $O(CH_2)_nNH_2$, $O(CH_2)_nCH_3$, $O(CH_2)_n ONH_2$ and $O(CH_2)_nON((CH_2)_nCH_3))_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278) and are presently suitable base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, as well as: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is incorporated herein by reference in its entirety, and U.S. Pat. No. 5,750,692, which is commonly owned with the instant application and which is also incorporated herein by reference in its entirety.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

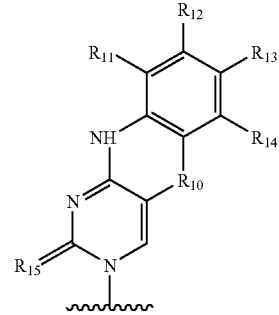

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov, et al., *Nucleosides and Nucleotides*, 1997, 16, 1837-1846), 1,3-diazaphenothiazine-2-one ($R_{10}$=S, $R_{11}$-$R_{14}$=H), (Lin et al., J. Am. Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang et al., Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. patent application Ser. No. 10/155,920, entitled "Modified Peptide Nucleic Acids" filed May 24, 2002; and U.S. patent application Ser. No. 10/013,295, entitled "Nuclease Resistant Chimeric Oligonucleotides" filed May 24, 2002, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12-14}$=H ) (Lin et al., M. J. Am. Chem. Soc., 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity (Lin et al., J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan et al., Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as: 4,845, 205; 5,130,302; 5,134,066; 5,175,273; 5,367,066; 5,432, 272; 5,434,257; 5,457,187; 5,459,255; 5,484,908; 5,502, 177; 5,525,711; 5,552,540; 5,587,469; 5,594,121; 5,596, 091; 5,614,617; 5,645,985; 5,646,269; 5,750,692; 5,830, 653; 5,763,588; 6,005,096; and 5,68 1,941, and U.S. patent application Ser. No. 09/996,292 filed Nov. 28, 2001, certain of which are commonly owned with the instant application, and each of which is herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, each of which is incorporated herein by reference in its entirety.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. Patents that teach the preparation of such oligonucleotide conjugates include, but are not limited to: U.S. Pat. Nos. 4,828,979; 4,948,882; 5,218,105; 5,525, 465; 5,541,313; 5,545,730; 5,552,538; 5,578,717, 5,580, 731; 5,580,731; 5,591,584; 5,109,124; 5,118,802; 5,138, 045; 5,414,077; 5,486,603; 5,512,439; 5,578,718; 5,608, 046; 4,587,044; 4,605,735; 4,667,025; 4,762,779; 4,789, 737; 4,824,941; 4,835,263; 4,876,335; 4,904,582; 4,958, 013; 5,082,830; 5,112,963; 5,214,136; 5,082,830; 5,112, 963; 5,214,136; 5,245,022; 5,254,469; 5,258,506; 5,262, 536; 5,272,250; 5,292,873; 5,317,098; 5,371,241, 5,391, 723; 5,416,203, 5,451,463; 5,510,475; 5,512,667; 5,514, 785; 5,565,552; 5,567,810; 5,574,142; 5,585,481; 5,587, 371; 5,595,726; 5,597,696; 5,599,923; 5,599,928 and 5,688, 941, certain of which are commonly owned with the instant application, and each of which is herein incorporated by reference.

Chimeric Compounds

It is not necessary for all positions in a given compound to be uniformly modified and, in fact, more than one of the aforementioned modifications may be incorporated in a single compound or even at a single nucleoside within an oligomeric compound.

The present invention also includes oligomeric compounds that are chimeric compounds. "Chimeric" oligomeric compounds or "chimeras," in the context of this invention, are oligomeric compounds, particularly antisense oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative U.S. patents that teach the preparation of such hybrid structures include, but are not limited to: U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is incorporated herein by reference in its entirety.

3'-endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

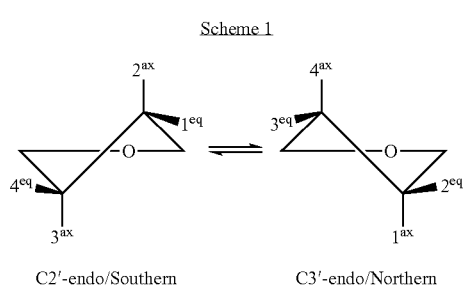

Scheme 1

C2'-endo/Southern          C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron, 2001, 57, 5707-5713; Harry-O'kuru et al., J. Org. Chem., 1997, 62(6), 1754-1759; and Tang et al., J. Org. Chem., 1999, 64, 747-754.) Alternatively, preference for the 3'-endo conformation can be achieved by deletion of the 2'-OH as exemplified by 2'deoxy-2'-nucleosides (Kawasaki et al., J. Med. Chem., 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters, 1995, 5, 1455-1460 and Owen et al., J. Org. Chem., 1976, 41, 3010-3017), or for example modification to yield methanocarba nucleoside analogs (Jacobson et al., J. Med. Chem. Lett., 2000, 43, 2196-2203 and Lee et al., Bioorganic and Medicinal Chemistry Letters, 2001, 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun., 1998, 4, 455-456), and ethylene bridged Nucleic Acids (ENA, Morita et al, Bioorganic & Medicinal Chemistry Letters, 2002, 12, 73-76). Examples of modified nucleosides amenable to the present invention are shown below in Table 1. These examples are meant to be representative and not exhaustive.

TABLE 1

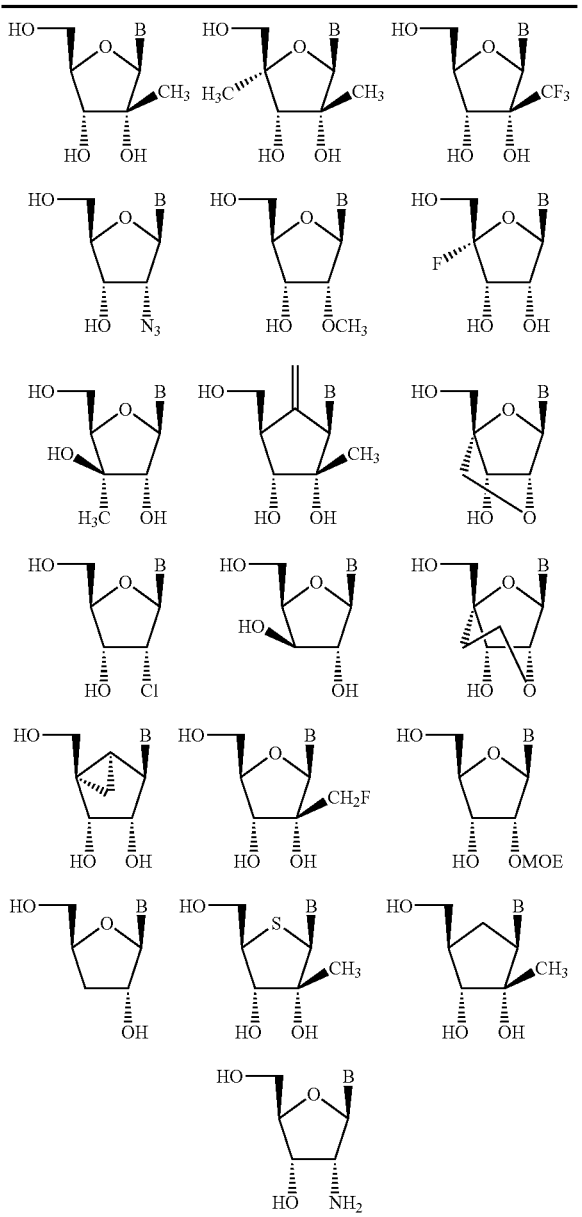

Suitable conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below).

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A suitable modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504). In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry*, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533).

The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one or about 1 to about 3, hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12 or from 1 to about 6, and the total number of ring members can vary from three to about 15 or from about 3 to about 8. Suitable ring heteroatoms are N, O and S. Suitable heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. Also suitable aryl rings include phenyl, napthyl, anthracenyl, and phenanthrenyl.

Unless otherwise defined herein, hetaryl means a ring moiety containing at least one filly unsaturated ring, the ring consisting of carbon and non-carbon atoms. The ring system can contain about 1 to about 4 rings. The number of carbon atoms can vary from 1 to about 12 or from 1 to about 6, and the total number of ring members can vary from three to about 15 or from about 3 to about 8. Suitable ring heteroatoms are N, O and S. Suitable hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209; 5,614,621; 6,051,699; 6,020,475; 6,326,478; 6,169,177; 6,121,437; and 6,465,628; each of which is incorporated herein by reference in its entirety.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative U.S. patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is incorporated herein by reference in its entirety.

The oligomeric compounds of the invention can encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE ((S acetyl-2-thioethyl) phosphate) derivatives according to the methods disclosed in WO 93/24510, WO 94/26764, and U.S. Pat. No. 5,770,713.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, suitable examples of pharmaceutically acceptable salts and their uses are further described in U.S. Pat. No. 6,287,860, which is incorporated herein by reference in its entirety.

The present invention also includes compositions and formulations, including pharmaceutical compositions and formulations, which include one or more of the oligomeric compounds of the invention. The compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes, but is not limited to, intravenous, intraarterial, subcutaneous, intraperitoneal, or intramuscular injection or infusion; or intracranial, e.g., intrathecal or intraventricular, administration. Oligonucleotides with at least one 2'-O-methoxyethyl modification are believed to be particularly useful for oral administration. Compositions and formulations for topical administration may include transdermal patches, ointments, lotions, creams, gels, drops, suppositories, sprays, liquids, and powders. Conventional pharmaceutical carriers, aqueous, powder or oily bases, thickeners and the like may be necessary or desirable. Coated condoms, gloves and the like may also be useful.

The formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

The compositions of the present invention may include solutions, emulsions, foams and liposome-containing formulations. The compositions and formulations of the present invention may comprise one or more penetration enhancers, carriers, excipients, or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein by reference in its entirety.

Formulations of the present invention may include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH sensitive or negatively charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present invention may also include surfactants. The use of surfactants in drug products, formulations and in emulsions is well known in the art. Surfactants and their uses are further described in U.S. Pat. No. 6,287,860, which is incorporated herein by reference in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

One of skill in the art will recognize that formulations are routinely designed according to their intended use, i.e. route of administration.

Suitable formulations for topical administration include those in which the oligonucleotides of the invention are in admixture with a topical delivery agent such as lipids, liposomes, fatty acids, fatty acid esters, steroids, chelating agents and surfactants. Suitable lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Suitable fatty acids and esters, pharmaceutically acceptable salts thereof, and their uses are further described in U.S. Pat. No. 6,287,860, which is incorporated herein by reference in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations are those in which oligonucleotides of the invention are administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860, which is incorporated herein by reference in its entirety. Also suitable are combinations of penetration enhancers, for example, fatty acids/salts in combination with bile acids/salts. A particularly suitable combination is the sodium salt of lauric acid, capric acid, and UDCA. Further penetration enhancers include, but are not limited to, polyoxyethylene-9-lauryl ether, and polyoxyethylene-20-cetyl ether.

Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference in its entirety. Oral formulations for oligonucleotides and their preparation are described in detail in U.S. application Ser. Nos. 09/108,673 (filed Jul. 1, 1998), 09/315, 298 (filed May 20, 1999) and 10/071,822, filed Feb. 8, 2002, each of which is incorporated herein by reference in its entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide compositions containing one or more oligomeric compounds and one or more other chemotherapeutic agents which function by a non-antisense mechanism. Examples of such chemotherapeutic agents include, but are not limited to, cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including, but not limited to, nonsteroidal anti-inflammatory drugs and corticosteroids, and antiviral drugs, including but not limited to ribivirin, vidarabine, acyclovir and ganciclovir, may also be combined in compositions of the invention. Combinations of oligomeric compounds and other non-antisense drugs are also within the scope of this invention. Two or more combined compounds may be used together or sequentially.

In another related embodiment, compositions of the invention may contain one or more oligomeric compounds, particularly antisense oligonucleotides, targeted to a first nucleic acid and one or more additional oligomeric compounds targeted to a second nucleic acid target. Alternatively, compositions of the invention may contain two or more oligomeric compounds targeted to different regions or segments of the same nucleic acid target. Numerous examples of oligomeric compounds are known in the art. Two or more combined compounds may be used together or sequentially.

Delivery

In some embodiments, the present invention is directed to methods and compositions for pulmonary delivery of oligonucleotide therapeutic compositions comprising penetration enhancers, carrier compounds and/or transfection agents. These methods are disclosed in International Publication WO 99/60166, which is incorporated herein by reference in its entirety.

Briefly, the compounds and methods of the invention employ particles containing oligonucleotide therapeutics or diagnostics. The particles can be solid or liquid, and can be of respirable size: that is, particles of a size sufficiently small to pass through the mouth and larynx upon inhalation and into the bronchi and alveoli of the lungs. In general, particles ranging from about 5 to 20 microns in size are respirable and are expected to reach the bronchioles (Allen, Secundum Artem, Vol. 6, No. 3, on-line publication updated May 8, 1998, and available at www.paddocklabs.com/secundum/secarndx.html). It is greatly desirable to avoid particles of non-respirable size, as these tend to deposit in the throat and be swallowed, thus reducing the quantity of oligonucleotide reaching the lung. Liquid pharmaceutical compositions of oligonucleotide can be prepared by combining the oligonucleotide with a suitable vehicle, for example sterile pyrogen free water, or saline solution. Other therapeutic compounds may optionally be included.

The present invention also contemplates the use of solid particulate compositions. Such compositions can comprise particles of oligonucleotide that are of respirable size. Such particles can be prepared by, for example, grinding dry oligonucleotide by conventional means, fore example with a mortar and pestle, and then passing the resulting powder composition through a 400 mesh screen to segregate large particles and agglomerates. A solid particulate composition comprised of an active oligonucleotide can optionally contain a dispersant which serves to facilitate the formation of an aerosol, for example lactose.

In accordance with the methods of the present invention, oligonucleotide compositions are aerosolized. Aerosolization of liquid particles can be produced by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blairex® under the name PARI LC PLUS, PARI DURA-NEB 2000, PARI-BABY Size, PARI PRONEB Compressor with LC PLUS, PARI WALKHALER Compressor/Nebulizer System, PARI LC PLUS Reusable Nebulizer, and PARI LC Jet+ ®Nebulizer.

Exemplary formulations for use in nebulizers comprise an oligonucleotide in a liquid, such as sterile, pyragen free water, or saline solution, wherein the oligonucleotide comprises up to about 40% w/w of the formulation. The oligonucleotide can comprise less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers. Metered dose inhalers suitable fore used in the art (along with the trade name, manufacturer and indication they are used for) and useful in the present invention include:

Delivery Device/Trade name/Manufacturer/Indication

Metered Dose Inhaler (MDI)/Alupent/Boehringer Ingelheim/Beta-adrenergic bronchodilator Metered Dose Inhaler (MDI)/Atrovent/Boehringer Ingelheim/Anticholinergic bronchodilator Aerobid/Aerobid-M/Forest/Steriodal Anti-inflammatory Beclovent/Beconase/Glaxo Wellcome/Steriodal Anti-inflammatory Flovent/Glaxo Wellcome/Steriodal Anti-inflammatory Ventolin/Glaxo Wellcome/Beta-adrenergic bronchodilator Proventil/Key Pharm./Beta-adrenergic bronchodilator Maxair/3M Pharm./Beta-adrenergic bronchodilator Azmacort/Rhone-Poulenc Rorer/Steriodal Anti-inflammatory Tilade/Rhone-Poulenc Rorer/Anti-inflammatory (inhibits release of inflammatory mediators)

Intal/Rhone-Poulenc Rorer/Inhibits mast cell degranulation (Asthma)

Vanceril/Schering/Steriodal Anti-inflammatory

Tornalate/Dura Pharm./Beta-adrenergic bronchodilator

Solutions for Nebulization

Alupent/Boehringer Ingelheim/Beta-adrenergic bronchodilator

Pulmozyme/Genetech/Recombinant human deoxyribonuclease I

Ventolin/Glaxo Wellcome/Beta-adrenergic bronchodilator

Tornalate/Dura Pharm./Beta-adrenergic bronchodilator

Intal/Rhone-Poulenc Rorer/Inhibits mast cell degranulation (Asthma)

Capsules (Powder) for Inhalation

Ventolin/Glaxo Wellcome/(Rotocaps for use in Rotohaler device)/Beta-adrenergic bronchodilator Powder for Inhalation Pulmicort/Astra USA/(Turbuhaler device)/Steroidal Anti-inflammatory In some embodiments, liquid or solid aerosols are produced at a rate of from about 10 to 150 liters per minute, from about 30 to 150 liters per minute, or about 60 liters per minute.

In some embodiments, a nucleic acid therapeutic or diagnostic composition is prepared, aerosolizing the nucleic acid composition, introducing the aerosolized nucleic acid composition into the lung of a mammal, and wherein the aerosolized nucleic acid composition comprises at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage. In some embodiments, the sugar moiety of at least one nucleoside unit of said oligonucleotide is not a 2'-deoxyribofuranosyl sugar moiety. In some embodiments, the nucleoside unit is a 2'-O-substituted nucleoside unit. In some embodiments, the 2-O-substituent of said 2'-O-substituted nucleoside unit is a 2'-O-alkoxyalkoxy substituent. In some embodiments, said 2-O-substituent of said 2'-O-substituted nucleoside unit is a 2'-O-dialkylaminooxyalkyl substituent. In some embodiments, at least one internucleotide linkage within said oligonucleotide is not a phosphodiester or a phosphorothioate linkage. In some embodiments, at least one internucleotide linkage within said oligonucleotide is a 3'-methylenephosphonate, a non-phosphorus containing oligonucleoside linkage, a 2'-5' linkage or is a 3'-deoxy-3'-amino phosphoramide linkage. In some embodiments, said pharmaceutical composition further comprises one or more pharmaceutically acceptable carriers. In some embodiments, said nucleic acid therapeutic or diagnostic composition is in aqueous media. In some embodiments, said nucleic acid therapeutic or diagnostic composition is sterilized, pyrogen free water. In some embodiments, said nucleic acid therapeutic or diagnostic composition is saline solution. In some embodiments, the nucleic acid therapeutic or diagnostic composition is a powder. In some embodiments, the nucleic acid therapeutic composition contains more than one oligonucleotide. In some embodiments, the oligonucleotide is an antisense oligonucleotide. In some embodiments, the nucleic acid therapeutic composition is aerosolized solution consists essentially of an antisense oligonucleotide in saline solution. In some embodiments, an animal having or suspected of having a disease or disorder that is treatable with one or more nucleic acids comprising administering a therapeutically effective amount of an aerosolized nucleic acid composition to the lung of the animal, wherein the aerosolized nucleic acid composition comprises at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage.

The compounds of the present invention may also be administered by pulsatile delivery. "Pulsatile delivery" refers to a pharmaceutical formulation that delivers a first pulse of drug combined with a penetration enhancer and a second pulse of penetration enhancer to promote absorption of drug which is not absorbed upon release with the first pulse of penetration enhancer.

One embodiment of the present invention is a delayed release oral formulation for enhanced intestinal drug absorption, comprising a first population of carrier particles comprising the drug and a penetration enhancer, wherein the drug and penetration enhancer are released at a first location in the intestine, and a second population of carrier particles comprising a penetration enhancer and a delayed release coating or matrix, wherein the penetration enhancer is released at a second location in the intestine downstream from the first location, whereby absorption of the drug is enhanced when the drug reaches the second location. Alternatively, the penetration enhancers in the populations of carrier particles are different.

This enhancement is obtained by encapsulating at least two populations of carrier particles. The first population of carrier particles comprises a biologically active substance and a penetration enhancer, and the second (and optionally additional) population of carrier particles comprises a penetration enhancer and a delayed release coating or matrix.

A "first pass effect" that applies to orally administered drugs is degradation due to the action of gastric acid and various digestive enzymes. One means of ameliorating first pass clearance effects is to increase the dose of administered drug, thereby compensating for proportion of drug lost to first pass clearance. Although this may be readily achieved with i.v. administration by, for example, simply providing more of the drug to an animal, other factors influence the bioavailability of drugs administered via non-parenteral means. For example, a drug may be enzymatically or chemically degraded in the alimentary canal or blood stream and/or may be impermeable or semipermeable to various mucosal membranes.

It is also contemplated that these pharmaceutical compositions are capable of enhancing absorption of biologically active substances when administered via the rectal, vaginal, nasal or pulmonary routes. It is also contemplated that release of the biologically active substance can be achieved in any part of the gastrointestinal tract.

Enhanced bioavailability of the biologically active substances is also achieved via the oral administration of the compositions and methods of the present invention. The term "bioavailability" refers to a measurement of what portion of an administered drug reaches the circulatory system when a non-parenteral mode of administration is used to introduce the drug into an animal.

Penetration enhancers include, but are not limited to, members of molecular classes such as surfactants, fatty acids, bile salts, chelating agents, and non-chelating non-surfactant molecules (Lee et al., Critical Reviews in Therapeutic Drug Carrier Systems, 1991, p. 92). Carriers are inert molecules that may be included in the compositions of the present invention to interfere with processes that lead to reduction in the levels of bioavailable drug.

Dosing

The formulation of therapeutic compositions and their subsequent administration (dosing) is believed to be within the skill of those in the art. Dosing is dependent on several criteria, including severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in vitro and in vivo animal models. In general, dosage is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight, once or more daily, to once every 20 years.

In some embodiments, 4-6 mg/kg of oligomer can be delivered intravenously. In other embodiments, 100 mg of oligomer can be delivered to the lungs in an aerosol.

Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include, but are not limited to, DNA arrays or microarrays (Brazma et al., FEBS Lett., 2000, 480, 17-24; Celis et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar et al., Methods Enzymol., 1999, 303, 258-72), TOGA (total gene expression analysis) (Sutcliffe et al., Proc. Natl. Acad. Sci. U.S.A., 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem., 2000, 286, 91-98; Larson et al., Cytometry, 2000, 41, 203-208), subtractive cloning, differential display (DD) (Jurecic et al., Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going et al., Eur. J. Cancer, 1999, 35, 1895-904) and mass spectrometry methods (To, Comb. Chem. High Throughput Screen, 2000, 3, 235-41).

The compounds of the invention are useful for research and diagnostics, for example, because these compounds hybridize to nucleic acids encoding a SARS virus. For example, oligonucleotides that are shown to hybridize with such efficiency and under such conditions as disclosed herein as to be effective SARS virus inhibitors will also be effective primers or probes under conditions favoring gene amplification or detection, respectively. These primers and probes are useful in methods requiring the specific detection of nucleic acid molecules encoding a SARS virus and in the amplification of nucleic acid molecules for detection or for use in further studies of SARS virus. Hybridization of the antisense oligonucleotides, particularly the primers and probes, of the invention with a nucleic acid encoding SARS virus can be detected by means known in the art. Such means include, but are not limited to, conjugation of an enzyme to the oligonucleotide, radiolabelling of the oligonucleotide, or any other suitable detection means. Kits using such detection means for detecting the level of a SARS virus in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is, thus, established that antisense compounds can be useful therapeutic modalities that can be configured to be useful in treatment regimes for the treatment of cells, tissues and animals, especially humans.

For therapeutics, an animal such as a human, suspected of having a disease or disorder which can be treated by modulating the expression of a SARS virus, is treated by administering oligomeric compounds, or compositions comprising the same, in accordance with this invention. For example, in one non-limiting embodiment, the methods comprise the step of administering to the animal in need of treatment, a therapeutically effective amount of a SARS virus inhibitor. The SARS virus inhibitors of the present invention effectively inhibit or reduce the activity of the SARS virus protein or inhibit or reduce the expression of a SARS virus protein. In one embodiment, the activity or expression of SARS virus in an animal is reduced by about 10% or more, about 20% or more, about 30% or more, about 40% or more, about 50% or more, about 60% or more, about 70% or more, about 80% or more, about 90% or more, about 95% or more, about 99% or more, or 100%.

For example, the reduction of the expression of a SARS virus may be measured in serum, adipose tissue, liver or any other body fluid, tissue or organ of the animal. In some embodiments, the cells contained within the fluids, tissues or organs being analyzed contain a nucleic acid molecule encoding a SARS virus protein and/or a SARS virus protein itself.

The compounds of the invention can be utilized in pharmaceutical compositions by adding an effective amount of a compound to a suitable pharmaceutically acceptable diluent or carrier. Use of the compounds and methods of the invention may also be useful, prophylactically.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-N4-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N4-benzoyl-5-methyl-cytidine penultimate intermediate, (5'-O-(4,4'-Dimethoxytriphenylmethyl)-2'-O-(2-methoxyethyl)-N$^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N$^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N$^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,Ndimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl)phosphoramidite.

Example 2

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hours), the oligonucleotides were recovered by precipitating with >3 volumes of ethanol from a 1 M NH$_4$OAc solution. Phosphinate oligonucleotides are prepared as described in U.S. Pat. No. 5,508,270, which is incorporated herein by reference in its entirety.

Alkyl phosphonate oligonucleotides are prepared as described in U.S. Pat. No. 4,469,863, which is incorporated herein by reference in its entirety.

3'-Deoxy-3'-methylene phosphonate oligonucleotides are prepared as described in U.S. Pat. Nos. 5,610,289 or 5,625,050, each of which is incorporated herein by reference in its entirety.

Phosphoramidite oligonucleotides are prepared as described in U.S. Pat. Nos. 5,256,775 or 5,366,878, each of which is incorporated herein by reference in its entirety.

Alkylphosphonothioate oligonucleotides are prepared as described in International Publications WO 94/17093 and WO 94/02499, each of which is incorporated herein by reference in its entirety.

3'-Deoxy-3'-amino phosphoramidate oligonucleotides are prepared as described in U.S. Pat. No. 5,476,925, each of which is incorporated herein by reference in its entirety.

Phosphotriester oligonucleotides are prepared as described in U.S. Pat. No. 5,023,243, which is incorporated herein by reference in its entirety.

Borano phosphate oligonucleotides are prepared as described in U.S. Pat. Nos. 5,130,302 and 5,177,198, each of which is incorporated herein by reference in its entirety.

Oligonucleosides

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, each of which is incorporated herein by reference in its entirety.

Formacetal and thioformacetal linked oligonucleosides are prepared as described in U.S. Pat. Nos. 5,264,562 and 5,264,564, each of which is incorporated herein by reference in its entirety.

Ethylene oxide linked oligonucleosides are prepared as described in U.S. Pat. No. 5,223,618, which is incorporated herein by reference in its entirety.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular, bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group that has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethylhydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, Ph.D. Thesis, University of Colorado, 1996; Scaringe et al., *J. Am. Chem. Soc.*, 1998, 120, 11820-11821; Matteucci et al., *J. Am. Chem. Soc.*, 1981, 103, 3185-3191; Beaucage et al., *Tetrahedron Lett.*, 1981, 22, 1859-1862; Dahl et al., *Acta Chem. Scand*, 1990, 44, 639-641; Reddy et al., *Tetrahedrom Lett.*, 1994, 25, 4311-4314; Wincott et al., *Nucleic Acids Res.*, 1995, 23, 2677-2684; Griffin et al., *Tetrahedron*, 1967, 23, 2301-2313; Griffin et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5X annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligomeric compounds, such as, oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hours at 55° C. The deprotected oligo is then recovered by an appropriate method (precipitation, column chromatography, volume reduced in vacuo and analyzed spetrophotometrically for yield and for purity by capillary electrophoresis and by mass spectrometry.

(2'-O-(2-Methoxyethyl))-(2'-deoxy)-(2'-O-(Methoxyethyl)) Chimeric Phosphorothioate Oligonucleotides (2'-O-(2-methoxyethyl))-(2'-deoxy)-(-2'-O-(methoxyethyl)) chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl) Phosphodiester) Chimeric Oligonucleotides (2'-O-(2-methoxyethyl phosphodiester)-(2'-deoxy phosphorothioate)-(2'-O-(methoxyethyl) phosphodiester) chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, which is incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition, specific protocols for the synthesis of oligomeric compounds of the invention are illustrated in the examples below.

RNA oligomers can be synthesized by methods disclosed herein or purchased from various RNA synthesis companies such as for example Dharmacon Research Inc., (Lafayette, Colo.).

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Example 5

Design and Screening of Duplexed Antisense Compounds Targeting SARS Virus

In accordance with the present invention, a series of nucleic acid duplexes comprising the antisense compounds of the present invention and their complements can be designed to target SARS virus. The nucleobase sequence of the antisense strand of the duplex comprises at least a portion of an oligonucleotide in the Sequence Listing. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:1) and having a two-nucleobase overhang of deoxythymidine(dT) would have the following structure:

```
cgagaggcggacgggaccgTT  Antisense Strand
|||||||||||||||||||    (SEQ ID NO:2)
TTgctctccgcctgccctggc  Complement Strand
                       (SEQ ID NO:3)
```

In another embodiment, a duplex comprising an antisense strand having the same sequence CGAGAGGCGGACGG-GACCG (SEQ ID NO:1) may be prepared with blunt ends (no single stranded overhang; i.e., the two "TT" overhangs shown above are omitted).

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 μM. Once diluted, 30 μL of each strand is combined with 15 μL of a 5X solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate SARS virus expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Additional Approaches to Targeting the SARS Virus Pseudoknot and Frameshift Site Ribosomal Frameshifting Programmed ribosomal frameshifting is ubiquitous in all three domains of life. Two components are required to cause frameshifting: a slippery site and a stable RNA structure a little bit downstream. Slippery sites are characterized by the sequence string X XXY YYN, where the initial reading frame is indicated by the spaces and the X and Y can be identical nucleotides. Frameshifting occurs because the RNA structural element a few nucleotides downstream from the slippery site (usually less than 8 nucleotides) causes the ribosome to pause briefly while the tRNA's for the XXY and YYN codons are docked to the mRNA in the ribosome. Because these tRNA's can also dock to the RNA in the −1 frame and still match (at least in the non-wobble positions) the complex slips one position backwards, and then continues to make protein in the −1 frame (XXX YYY N). The downstream RNA structure facilitates the slippage.

Frameshifting is a widespread phenomenon in viruses, bacteria, protozoa and mammalian systems. Some mammalian genes have programmed frameshift sites. Of course, since viruses replicate in eukaryotic cells, we know that a wide variety of viral frameshift signals work well with eukaryotic ribosomes. Natural frameshift signals vary in efficiency from just a few percent up to nearly 100 percent, depending upon the strength of the signal.

In viruses, frameshifting is used to produce two different proteins in a desired ratio. HIV uses ribosomal frameshifting to make the structural protein gag, and its polymerase in a specific ratio. HIV needs a lot of gag, but only a little polymerase. About 95% of the time there is no frameshift, and only the gag structural protein is made using the first half of the mRNA. An in-frame stop codon for gag terminates translation. But 5% of the time, when frameshifting occurs, a fusion protein is made that contains polymerase, which HIV needs less of. The strength of the frameshift signal is tuned to produce the desired balance of each protein.

Another use of frameshifting is to produce two proteins with the same sequence, but different lengths. In this case there is only one productive reading frame and the frameshift throws translation out of frame immediately into a stop codon that results in a shorter than the full length product. An example of this is the dnaX gene of enteric bacteria. The dnax gene produces two proteins, tau and gamma, with different lengths. Tau is shorter than gamma because of the programmed frameshift.

In nature, the stability of the RNA structure downstream of the frameshift site controls the frequency of frameshifting. In the high percentage frameshift signals the structure is a pseudoknot, and in the low percentage frameshifts, such as HIV, it's a simple hairpin. Furthermore, it has been shown that by increasing the stability of the RNA structure, frameshifting can be enhanced. This can be accomplished by either a site directed mutagenesis that causes a more stable structure, or by adding an antisense oligonucleotide that adds to the length of a stem in a pre-existing structure.

Potential Ribosomal Frameshift Site in SARS Virus

Ribosomal frameshifting has been documented as an essential feature in a number of viruses. These include the retroviruses (such as HIV), the Coronaviridae, Astroviridae, Totiviridae, among other families of viruses. The Coronaviridae is the family of viruses that infect humans and animals, and includes a species of virus that causes a common cold-like respiratory illness known as Human Coronavirus 229E (HCo-V-229E). Also included in this family are an avian infectious bronchitis virus (IBV), murine hepatitis virus (MHV), porcine transmissible gastroenteritis virus PRCoV, procine respiratory coronavirus and bovine coronavirus, among others (Lai and Holmes, Chapter 35 in the virus book). A well studied frameshift site is the Infectious Bronchitis Virus, a coronavirus that infects chickens. The structure of the IBV virus is a slippery site followed by a pseudoknot (see, FIG. 1).

The reason that coronavirus frameshift site exists is not clear. The frameshift site in coronaviruses is in between ORFs 1a and 1b. ORF 1a contains a number of proteins, including proteases, and ORF 1b contains the RNA-dependent-RNA-Polymerase. The RNA-dependent-RNA-Polymerase is an essential gene. Unlike some other RNA-genome viruses, Coronaviruses do not carry a copy of the RNA-dependent-RNA-Polymerase in the virion particle. Therefore, to succeed in replicating, the RNA-dependent-RNA-Polymerase must be translated directly from the genomic RNA. Since the RNA-dependent-RNA-Polymerase is located downstream of the frameshift site, it is absolutely required that the frameshift signal work in order to produce the coronavirus RNA-dependent-RNA-Polymerase, which is −1 out of frame with respect to the upstream ORF 1a. Perhaps this is why the infectious bronchitis virus frameshift site is so efficient (most are from 20-40% efficient).

If the SARS virus behaves the same way as the previously documented coronaviruses, it will have frameshift signal is a similar position of the genome, and the function of the frameshift site will be essential to the lifecycle of the virus. To determine if the SARS virus has a similar frameshift signal, a comparative analysis of SARS virus sequences published in GenBank, and previously known coronaviruses was conducted. The results of this analysis suggest that the SARS virus has a significant degree of sequence homology with the other coronaviruses that have documented frameshift sites. Confirmation that the SARS virus indeed likely has a frameshift site is shown by a comparison of structure. From the sequence comparison it can be determined that the regions involved in forming the slippery site and pseudoknot are more conserved in the alignment. Where changes occur in the pseudoknot structure, they are covarying pairs, which changes sequence, but conserves structure.

Antisense Inhibition of the SARS Virus Ribosomal Frameshift Site

Oligonucleotides can be designed to disrupt or enhance the frameshift site. Oligonucleotides can be run beyond the end of stem 2, but breaking it up after nucleating outside the structure.

Cellular Localization

The present invention also encompasses compounds or molecules that are equipped or formulated with motifs that modulate intracellular distribution, localization, or retention of the molecule within a specific compartment of the cell. The motif specifically associates, complexes, or interacts with cellular components or macromolecules that predominantly reside or traffic to a location, compartment, or domain of a cell in which the basis of antisense activity, be it enzyme or process, occurs. The compounds or molecules of the invention may be synthetic or biological in nature, that regulate gene expression in a sequence-specific manner.

This invention is useful for antisense-based molecules which distribute or localize to sites in addition to or other than those which precede or are associated with antisense activity. This invention is intended to increase the effective concentration of the antisense molecule at point of action to increase its potency and/or efficacy.

The following motifs are candidate motifs for attachment or formulation with antisense molecules of interest, e.g. Rnase H ASOs (nucleus/nucleolus), siRNAs (cytoplasm), asRNAs (cytoplasm), 5' capping inhibitors (nucleus), splicing inhibitors (nucleus), polyadenylation inhibitors (nucleus), translation inhibitors (cytoplasm, or preload in nucleus), 2-5 RNAseL (cytoplasm).

Peptide Motifs

"Leucine-rich" nuclear export signal (NES) for cytoplasmic localization; e.g. LQLPPLERLTL (rev) (SEQ ID NO:4), DLQKKLEELEL (MAPKK) (SEQ ID NO:5), ELALKLAGLDI (PKI-alpha) (SEQ ID NO:6), ALPHAIMRLDLA (actin) (SEQ ID NO:7).

KDEL (SEQ ID NO:8) for endoplasmic reticulum localization.

Arginine/lysine rich motifs for nuclear and/or nucleolar localization; e.g. nucleolar, PQRRNRSRRRRFRGQ (FXR2P) (SEQ ID NO:9), IMRRRGL (Angiogenin) (SEQ ID NO:10), GRKKRRQRRR (HIV-1 TAT) (SEQ ID NO:11).

Dermaseptin Derivatives (antimicrobial peptide), e.g. ALWKTLLKKVLKA (SEQ ID NO:12), demonstrated uptake into HeLa cells, cytoplasmic localization.

RS, RE, and RD repeat motifs for nuclear and nuclear speckle localization.

RG and KS repeat motifs for cytoplasmic localization.

Hydrophobic Motifs

Alkyl chains, e.g. $C_{10}$ to $C_{30}$.

Nucleic Acid Motifs

A strings—poly A binding protein (nuclear and cytoplasmic forms), e.g. An.

AU Rich Elements—ELAV Family
  e.g. UUAUUUAUU minimum seq/length.

CU rich elements—ELAV Family
  e.g. (CUUU)n recognized by HuD and HuR.

hnRNP Substrates
  e.g. hnRNP A1 and K shuttle between the nucleus and cytoplasm, A1 associates w/PAPBl, transportin, and mRNA in the cytoplasm. High affinity binding site for A1 is UAGGGA/U.

Other Shuttling Protein Substrates (hnRNP-Like)
  e.g. JKTBPs, consensus binding sites (GG)ACUAGC(A).

Y Strings or Tracts
  e.g. substrates for hnRNP I (PTBP1/PTB).

Pumilio Recognition Sequence
  e.g. UGUANAUR, where N is any base and R is a purine (Cell, 2002, 110, 501-12).

Combinatorial Selection
  e.g. $N_{10}$-Fluorescent or Biotin Tag for identification of sequences that distribute to different subcellular locations.

Once localized in the correct compartment, enzymes residing there can effect modification of the target nucleic acid. For example, if localization to the cytoplasm is effected, RNAse L can be activated and result in the destruction of nucleic acid targets.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen or can be transfected into the cell type or, in the case of an infectious agent, if the foreign nucleic acid is found in the cell type infected. This can be readily determined by methods routine in the art, for example Northern blot analysis, ribonuclease protection assays, or RT-PCR.

Human Cell Lines

T-24 Cells:
  The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:
  The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Primate Cell Lines

Vero E6 Cells:

These cells can be maintained, cultured and inoculated with biological specimens thought to contain the SARS virus via the method of Ksiazek et al., New England Journal of Medicine, 2003, 348(20), 1947-1958. Following infection, RNA can be isolated from the cells and oligonucleotide primers and probes to the virus can be used for quantitation of RNA by RT-PCR by any of the methods of Ksiazek et al., New England Journal of Medicine, 2003, 348(20), 1947-1958 or Drosten et al., New England Journal of Medicine, 2003, volume 348(20), 1967-1976.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEMm-1 containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG) (SEQ ID NO:13) which is targeted to human H-ras, or ISIS 18078, (GTGCGCGCGAGCCCGAAATC) (SEQ ID NO:14) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA (SEQ ID NO:15), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of SARS Virus Expression

Antisense modulation of SARS virus expression can be assayed in a variety of ways known in the art. For example, SARS virus mRNA levels can be quantitated by, e.g., Northern blot analysis, competitive polymerase chain reaction (PCR), or real-time PCR (RT-PCR). Real-time quantitative PCR is presently suitable. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of SARS virus can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to SARS virus can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and in vivo Studies for the Use of SARS Virus Inhibitors Phenotypic Assays Once SARS virus inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of SARS virus in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.) blood and other body fluid viral titres.

In one non-limiting example, cells determined to be appropriate for a particular phenotypic assay (i.e., MCF-7 cells selected for breast cancer studies; adipocytes for obesity studies; blood or sputum samples for viral titres) are treated with SARS virus inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals, viral titres, infection or inflammatory markers. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the SARS virus inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or SARS virus inhibitor. Furthermore, to prevent the doctors from being biased in treatments, they are not informed as to whether the medication they are administering is a SARS virus inhibitor or a placebo. Using this randomization approach, each volunteer has the same chance of being given either the new treatment or the placebo.

Volunteers receive either the SARS virus inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding SARS virus or SARS virus protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/ great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and SARS virus inhibitor treatment. In general, the volunteers treated with placebo have little or no response to treatment, whereas the volunteers treated with the SARS virus inhibitor show positive trends in their disease state or condition index at the conclusion of the study.

Example 12

RNA Isolation

Poly(A)+ mRNA Isolation

Poly(A)+ mRNA was isolated according to Miura et al., (Clin. Chem., 1996, 42, 1758-1764). Other methods for poly(A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of SARS Virus mRNA Levels

Quantitation of SARS virus mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreenr are taught in Jones et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to SARS virus were designed to hybridize to a SARS virus VIRUS sequence, using published sequence information (GenBank accession number NC_004718.1, incorporated herein as SEQ ID NO:16). For SARS virus the PCR primers can be prepared as by the method of Drosten et al. For human GAPDH the PCR primers can be:

```
forward   GAAGGTGAAGGTCGGAGTC     (SEQ ID NO: 17)
primer:

reverse   GAAGATGGTGATGGGATTTC    (SEQ ID NO: 18)
primer:
``` and the PCR probe was:

```
5'
JOE-CAAGCTTCCCGTTCTCAGCC-TAMRA 3  (SEQ ID NO: 19)
``` where JOE is the fluorescent reporter dye and TAMRA is the quencher dye.

Example 14

Northern Blot Analysis of SARS Virus mRNA Levels

Eighteen hours after antisense treatment, cell monolayers were washed twice with cold PBS and lysed in 1 mL RNAZOL™ (TEL-TEST "B" Inc., Friendswood, Tex.).

Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect SARS virus, a SARS virus specific probe was prepared. To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of SARS Virus Expression by Chimeric Phosphorothioate Oligonucleotides having 2'-MOE Wings and a Deoxy Gap In accordance with the present invention, a series of antisense compounds are designed to target different regions of the SARS virus RNA, using published sequences (GenBank accession number NC_004718.1, incorporated herein as SEQ ID NO:16). The compounds listed in the accompanying Sequence Listing. "Target site" indicates the first (5'-most) nucleotide number on the particular target sequence to which the compound binds. The compounds can be "gapmers" 20 nucleotides in length. The compounds can be analyzed for their effect on SARS virus mRNA levels by quantitative real-time PCR as described in other examples herein.

The target regions to which these sequences are complementary are herein referred to as "suitable target segments" and are therefore suitable for targeting by compounds of the present invention. The sequences represent the reverse complement of the compounds listed in the Sequence Listing.

As these "suitable target segments" can be found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these suitable target segments and consequently inhibit the expression of SARS virus.

According to the present invention, antisense compounds include antisense oligomeric compounds, antisense oligonucleotides, siRNAs, miRNAs, dsRNAs, duplexed compounds, ribozymes, external guide sequence (EGS) oligonucleotides, alternate splicers, primers, probes, and other short oligomeric compounds which hybridize to at least a portion of the target nucleic acid.

Example 16

Western Blot Analysis of SARS Virus Protein Levels

Western blot analysis (immunoblot analysis) is carried out using standard methods. Cells are harvested 16-20 hours after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to SARS virus is used, with a radiolabeled or fluorescently labeled secondary antibody directed against the primary antibody species. Bands are visualized using a PHOSPHORIMAGERT (Molecular Dynamics, Sunnyvale Calif.).

Example 17

SARS-CoV Sequences

Several fragments and complete genome sequences of SARS variants are available in the public databases. In accordance with the present invention, antisense compounds can be designed to target different structural regions or variants or motifs of SARS, using the published sequences in Table 2. Such compounds can be designed, synthesized, and tested as disclosed herein.

TABLE 2

Sequences of SARS genomes and fragments

| GENBANK ACCESSION NUMBER | SEQUENCE LENGTH | SEQ ID NO |
|---|---|---|
| NC_004718.1 | 29736 | 16 |
| AY278741.1 | 29727 | 29737 |
| AY278490.1 | 29291 | 29738 |
| AY278489.1 | 29429 | 29739 |
| AY278488.1 | 28920 | 29740 |
| AY278487.1 | 29430 | 29741 |
| AY278554.1 | 29206 | 29742 |
| AY268049.1 | 433 | 29743 |
| AY278491.2 | 29742 | 29744 |
| AY269391.1 | 405 | 29745 |
| AY274119.1 | 29736 | 29746 |
| AY278554.2 | 29736 | 29747 |
| AY279354.1 | 24774 | 29748 |
| AY274119.2 | 29736 | 29749 |
| NC_004718.2 | 29736 | 29750 |
| AY274119.3 | 29751 | 29751 |
| NC_004718.3 | 29751 | 29752 |
| AY278488.2 | 29725 | 29753 |
| AY271716.1 | 158 | 29754 |
| AY283798.1 | 29711 | 29755 |
| AY283797.1 | 29706 | 29756 |
| AY283796.1 | 29711 | 29757 |
| AY283795.1 | 29705 | 29758 |
| AY283794.1 | 29711 | 29759 |
| AY297028.1 | 29715 | 29760 |
| AY286402.1 | 368 | 29761 |
| AY291451.1 | 29729 | 29762 |
| AY282752.1 | 29736 | 29763 |
| AY268070.1 | 646 | 29764 |
| AY268049.1 | 433 | 29765 |
| AY286320.2 | 1215 | 29766 |
| AY307165.1 | 1269 | 29767 |
| AY278487.3 | 29745 | 29768 |
| AY278489.2 | 29757 | 29769 |
| AY278490.3 | 29740 | 29770 |
| AY279354.2 | 29732 | 29771 |
| AY290752.1 | 1620 | 29772 |
| AY291315.1 | 29727 | 29773 |

TABLE 2-continued

Sequences of SARS genomes and fragments

| GENBANK ACCESSION NUMBER | SEQUENCE LENGTH | SEQ ID NO |
|---|---|---|
| AY321118.1 | 29725 | 29774 |
| AY323974.1 | 666 | 29775 |
| AY323975.1 | 231 | 29776 |
| AY323976.1 | 3768 | 29777 |
| AY323977.1 | 29751 | 29778 |
| AY283798.2 | 29711 | 29779 |
| AP006557.1 | 29727 | 29780 |
| AP006558.1 | 29725 | 29781 |
| AP006559.1 | 29727 | 29782 |
| AP006560.1 | 29727 | 29783 |
| AP006561.1 | 29727 | 29784 |
| AY278488.2 | 29725 | 29785 |
| AY278489.2 | 29757 | 29786 |
| AY278490.3 | 29740 | 29787 |
| AY279354.2 | 29732 | 29788 |
| AY282752.2 | 29736 | 29789 |
| AY283794.1 | 29711 | 29790 |
| AY283795.1 | 29705 | 29791 |
| AY283796.1 | 29711 | 29792 |
| AY283797.1 | 29706 | 29793 |
| AY283798.2 | 29711 | 29794 |
| AY297028.1 | 29715 | 29795 |
| AY304486.1 | 29741 | 29796 |
| AY304488.1 | 29731 | 29797 |
| AY304495.1 | 29720 | 29798 |
| AY310120.1 | 29740 | 29799 |
| AY313906.1 | 29754 | 29800 |
| AY323977.2 | 29751 | 29801 |
| AY338174.1 | 29573 | 29802 |
| AY338175.1 | 29573 | 29803 |
| AY345986.1 | 29736 | 29804 |
| AY345987.1 | 29736 | 29805 |
| AY345988.1 | 29736 | 29806 |
| AY348314.1 | 29573 | 29807 |
| AY350750.1 | 29738 | 29808 |
| AY351680.1 | 29749 | 29809 |
| AY357075.1 | 29738 | 29810 |
| AY357076.1 | 29745 | 29811 |
| AY362698.1 | 29727 | 29812 |
| AY362699.1 | 29727 | 29813 |
| AY394850.1 | 29735 | 29814 |
| AY427439.1 | 29711 | 29815 |
| AY461660.1 | 29715 | 29816 |
| AY485277.1 | 29741 | 29817 |
| AY485278.1 | 29740 | 29818 |
| AY463060.1 | 29013 | 29819 |
| AY463059.1 | 29592 | 29820 |
| AY502923.1 | 29729 | 29821 |
| AY502924.1 | 29727 | 29822 |
| AY502925.1 | 29729 | 29823 |
| AY502926.1 | 29729 | 29824 |
| AY502927.1 | 29729 | 29825 |
| AY502928.1 | 29729 | 29826 |
| AY502929.1 | 29729 | 29827 |
| AY502930.1 | 29729 | 29828 |
| AY502931.1 | 29729 | 29829 |
| AY502932.1 | 29729 | 29830 |

Example 18

Antisense Inhibition of the SARS-CoV with Oligonucleotides Complementary to the Positive Strand of the Virus In accordance with the present invention, compounds were designed to target different regions or variants or motifs of the SARS virus RNA, using published sequences (Genbank accession number NC_004718.1, NC_004718.3, AY278741.1, AY274119.3 or AY278489.1).

Compounds targeting SARS are shown in Table 3. "Target site" indicates the first (5'-most) nucleotide number on the particular target sequence to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-O-methoxyethyl nucleotides, also known as 2'-MOE. The internucleoside (backbone) linkages are phosphorothioate (P=S) throughout the oligonucleotide. All cytidine residues are 5-methylcytidines.

TABLE 3

Chimeric phosphorothioate oligonucleotides targeted to SARS

| ISIS # | TARGET SEQ ID NO | TARGET | SEQUENCE (5' to 3') | SEQ ID NO |
|---|---|---|---|---|
| 329410 | 16 | 13971 | AGATCCTGATTATCTAATGT | 13990 |
| 329411 | 16 | 13977 | CCATTAAGATCCTGATTATC | 13996 |
| 329412 | 16 | 15195 | GGATAATCCCAACCCATAAG | 15214 |
| 329413 | 16 | 15435 | ACAGCTTGACAAATGTTAAA | 15454 |
| 329414 | 16 | 15618 | TCATCAGAAAGAATCATCAT | 15637 |
| 329415 | 16 | 15714 | AACACATTATTTTGATAATA | 15733 |
| 329416 | 16 | 17079 | GCATCAACAGCTGCATGAGA | 17098 |
| 329417 | 16 | 18543 | GGTCCAATCTTGACAAAGTA | 18562 |
| 329418 | 16 | 18770 | ATCTAGTCATGATAGCATCA | 18789 |
| 329419 | 16 | 25053 | CAAACATACCAAGGCCATTT | 25072 |
| 329420 | 16 | 1 | GGTTGGCTTTTCCTGGGTAG | 20 |
| 329421 | 16 | 2 | TGGTTGGCTTTTCCTGGGTA | 21 |
| 329422 | 29737 | 1 | GGTAGGTAAAAACCTAATAT | 29831 |
| 329423 | 29739 | 1 | TGGTTGCGAAAATAAAGGGG | 29832 |
| 329424 | 16 | 192 | CTGATGATCGACTGCAACAC | 211 |
| 329425 | 16 | 202 | CCTAGGTATGCTGATGATCG | 221 |
| 329426 | 16 | 353 | CTCCGATAGGGCCTCTTCCA | 372 |
| 329427 | 16 | 371 | TTTGAGGTGTTCACGTGCCT | 390 |
| 329428 | 16 | 1316 | AGTAGGTAGGTACCCACATG | 1335 |
| 329429 | 16 | 1753 | TTACCGCAGGACTCAACAAT | 1772 |
| 329430 | 16 | 1755 | AGTTACCGCAGGACTCAACA | 1774 |
| 329431 | 16 | 1850 | AGCCTGTGAGGGAAAACCAC | 1869 |
| 329432 | 16 | 2075 | ATTAGACAACCACTGAGAAG | 2094 |
| 329433 | 16 | 2384 | ACGGTAAAGTCCCTTGCTTT | 2403 |
| 329434 | 16 | 2734 | TGAACTTCCCAAACAGTATC | 2753 |
| 329435 | 16 | 2811 | AGACAGAGCACTTTTCATTA | 2830 |
| 329436 | 16 | 3131 | TGAGGCACCAAATTCCAGAG | 3150 |
| 329437 | 16 | 3289 | CATTTAATGGCAACATTGTC | 3308 |
| 329438 | 16 | 4006 | GCATCCTTCTCAAGGAAAGA | 4025 |

TABLE 3-continued

Chimeric phosphorothioate oligonucleotides targeted to SARS

| ISIS # | TARGET SEQ ID NO | TARGET | SEQUENCE (5' to 3') | SEQ ID NO |
|---|---|---|---|---|
| 329439 | 16 | 4252 | TCCTTAGCATTAGGTGCTTC | 4271 |
| 329440 | 16 | 4823 | GTCAAGTGAAAGAACCTCAC | 4842 |
| 329441 | 16 | 5275 | CCAGCACGGGCTCTATAATA | 5294 |
| 329442 | 16 | 5329 | CCAACAGTTTTATTACTGTA | 5348 |
| 329443 | 16 | 5467 | ATCACAGCTTCTACACCCGT | 5486 |
| 329444 | 16 | 5624 | GAATGTACCTTGCTGTAATT | 5643 |
| 329445 | 16 | 5634 | TCGCACATAAGAATGTACCT | 5653 |
| 329446 | 16 | 5995 | GTCATTTGATTTAAATCATC | 6014 |
| 329447 | 16 | 6462 | CCACATAAGCAGCCATAAGA | 6481 |
| 329448 | 16 | 6600 | CTAAGAATGGTTTGACATAA | 6619 |
| 329449 | 16 | 6975 | TAAGATACAATTCTCTAACG | 6994 |
| 329450 | 16 | 7009 | TCACAGAAATCCATAGTAGT | 7028 |
| 329451 | 16 | 7146 | AAACCCACTCAGCGGCCAGA | 7165 |
| 329452 | 16 | 7522 | TTGAGACAATTCCAATTGTG | 7541 |
| 329453 | 16 | 7952 | GGTGTCGACATAAGCATCAA | 7971 |
| 329454 | 16 | 8006 | TGTAGCAACAAGTGCCTTAA | 8025 |
| 329455 | 16 | 8570 | TGTGTAACCATCATGGATTG | 8589 |
| 329456 | 16 | 8578 | ATTTCATTTGTGTAACCATC | 8597 |
| 329457 | 16 | 9091 | GTTACTACTCTAACAGAACC | 9110 |
| 329458 | 16 | 9132 | TTTCGCATGTACCATGTCTA | 9151 |
| 329459 | 16 | 9365 | TCTGAATTTCATAAAGTAGT | 9384 |
| 329460 | 16 | 9875 | TAGAGCCTTTGCTAAGTGGC | 9894 |
| 329461 | 16 | 9918 | GTGGTTGGTAGAGAACATCA | 9937 |
| 329462 | 16 | 9989 | AACTTTGCCTGACGGGAATG | 10008 |
| 329463 | 16 | 10446 | CCATATGATGCATATAGCAG | 10465 |
| 329464 | 16 | 10777 | ATACCATTCTGCAGCAGCTC | 10796 |
| 329465 | 16 | 11187 | CAGACAAGCTAGTGTCAGCC | 11206 |
| 329466 | 16 | 11494 | CACTGTAAGGTGTTGCCAGT | 11513 |
| 329467 | 16 | 11963 | CATTTCCTCGCACAACCTAT | 11982 |
| 329468 | 16 | 11988 | CCTGAAGAGTAGCACGGTTA | 12007 |
| 329469 | 16 | 12254 | TGTTTGCATAGCACTAGTTA | 12273 |
| 329470 | 16 | 12435 | CATATGTAAAGGTGTTACCA | 12454 |
| 329471 | 16 | 13159 | TGGCATCTACAATACAGACA | 13178 |
| 329472 | 16 | 13176 | GATTTGGATGGTCAATGTGG | 13195 |
| 329473 | 16 | 13223 | GGTAGGTATTTGGACGTACT | 13242 |
| 329474 | 16 | 13608 | TTAACCAAGTTATAAATAGT | 13627 |
| 329475 | 16 | 13978 | CCCATTAAGATCCTGATTAT | 13997 |
| 329476 | 16 | 14039 | CCACAATAGGAACTCCGCAG | 14058 |
| 329477 | 16 | 14239 | ACAGTTAATACAATTGGGAT | 14258 |
| 329478 | 16 | 14705 | GATAATAGTCATAATCACTG | 14724 |
| 329479 | 16 | 14828 | GATTGTTAACGATTACTTGG | 14847 |
| 329480 | 16 | 14976 | GCATACTTAAGATTCATTTG | 14995 |
| 329481 | 16 | 15065 | TCAATAATTTCTGATGAAAC | 15084 |
| 329482 | 16 | 15401 | AAGCAGTTGTAGCATCACCG | 15420 |
| 329483 | 16 | 15725 | CCTCAGACATGAACACATTA | 15744 |
| 329484 | 16 | 15817 | CACGTAATCATCTCCTTGTT | 15836 |
| 329485 | 16 | 15885 | GTTTTGACAATATCATCGAC | 15904 |
| 329486 | 16 | 16634 | CCCATGAAAGATGCAATTCT | 16653 |
| 329487 | 16 | 16869 | TAGTGCTCTTGTGGCACTAG | 16888 |
| 329488 | 16 | 17309 | CACGAAGTCTAGCATTGACA | 17328 |
| 329489 | 16 | 17719 | AGGCAATCCTAAGATTTTTG | 17738 |
| 329490 | 16 | 17749 | AGAACCCTGTGATGAATCAA | 17768 |
| 329491 | 16 | 18401 | CTTTATACATGAGTGGTATA | 18420 |
| 329492 | 16 | 18429 | TTAATACGCACTACATTCCA | 18448 |
| 329493 | 16 | 18507 | TCAAAGCCATGCGCCCAAAG | 18526 |
| 329494 | 16 | 18925 | ATGAAGAACTGGAAACTTAT | 18944 |
| 329495 | 16 | 19520 | AACTCTGTAACCTGGTAAAT | 19539 |
| 329496 | 16 | 19532 | CCACATTTTCTAAACTCTGT | 19551 |
| 329497 | 16 | 20753 | CTCTCATGTTGTAGGGTACA | 20772 |
| 329498 | 16 | 21032 | TTTGCTTTATAAATCCACAC | 21051 |
| 329499 | 16 | 21353 | TTTGATTCTCCTTAAGAGAC | 21372 |
| 329500 | 16 | 22147 | ATTTGTAATGTTAATACCAA | 22166 |
| 329501 | 16 | 22992 | CCACAAACCGTGGCCGGTGC | 23011 |
| 329502 | 16 | 23069 | ACACACCAGTACCAGTGAGT | 23088 |
| 329503 | 16 | 23507 | CAGCACCTAAAGACATAGTA | 23526 |
| 329504 | 16 | 23829 | GGGTCAGGTAATATTTGTGA | 23848 |
| 329505 | 16 | 24421 | GGTTTGAAGGCTTTGAAGTC | 24440 |
| 329506 | 16 | 24871 | GAAGTACTTGTCCAGCTCTT | 24890 |
| 329507 | 16 | 25466 | TGGAAGCCCTTATAAAGGGC | 25485 |
| 329508 | 16 | 25880 | GACTCAAGCTGGTAGTAAAC | 25899 |
| 329509 | 16 | 25899 | GTCTGTAGTAATTTGTGTAG | 25918 |
| 329510 | 16 | 26389 | ACGGTAATAGTACCGTTGTC | 26408 |

TABLE 3-continued

Chimeric phosphorothioate oligonucleotides targeted to SARS

| ISIS # | TARGET SEQ ID NO | TARGET | SEQUENCE (5' to 3') | SEQ ID NO |
|---|---|---|---|---|
| 329511 | 16 | 26433 | CTATTACTAGGTTCCATTGT | 26452 |
| 329512 | 16 | 26482 | TTAGAATAGGCAAATTGTAG | 26501 |
| 329513 | 16 | 26781 | CAATGACAAGTTCACTTTCC | 26800 |
| 329514 | 16 | 27130 | CGTCAAGATTCCAAATAGCA | 27149 |
| 329515 | 16 | 27266 | TCAATGTCAGGAAGAGAATA | 27285 |
| 329516 | 16 | 27406 | TAGTGCAAATTTATTGTCAG | 27425 |
| 329517 | 16 | 27501 | ATGAAAAGTTTTGGTGAAAC | 27520 |
| 329518 | 16 | 27538 | TGGCGAGTAGAGCTCTTGTT | 27557 |
| 329519 | 16 | 27894 | CAAAGCCAAGCAGTGCTATA | 27913 |
| 329520 | 16 | 28161 | CAGTTGAATCTGTGGGTCCA | 28180 |
| 329521 | 16 | 29109 | CATCCAATTTAATGGCTCCA | 29128 |
| 329522 | 16 | 29468 | CTTGTGCTGTTTAGTTACGA | 29487 |
| 329523 | 16 | 29504 | AAGATTGCTATGTGAGATTA | 29523 |
| 329524 | 16 | 13377 | ACACCGCAAACCCGTTTAAA | 13396 |
| 329525 | 16 | 13385 | CTGCACTTACACCGCAAACC | 13404 |
| 329526 | 16 | 13392 | AGACGGGCTGCACTTACACC | 13411 |
| 329527 | 16 | 13396 | TGTAAGACGGGCTGCACTTA | 13415 |
| 329528 | 16 | 13426 | GACATCAGTACTAGTGCCTG | 13445 |
| 329529 | 16 | 13445 | TATCAAAAGCCCTGTAGACG | 13464 |
| 329530 | 16 | 13452 | TTGTAAATATCAAAAGCCCT | 13471 |
| 329531 | 16 | 45 | TTTTAAAGTTCGTTTAGAGA | 64 |
| 329532 | 16 | 21464 | TAAACATGTTCGTTTAGTTG | 21483 |
| 329533 | 16 | 25238 | TCCATAAGTTCGTTTATGTG | 25257 |
| 329534 | 16 | 26087 | TACATAAGTTCGTACTCACT | 26106 |
| 329535 | 16 | 26326 | ATAGTTAGTTCGTTTAGACC | 26345 |
| 329536 | 16 | 26891 | AGAAAGCGTTCGTGATGTAG | 26910 |
| 329537 | 16 | 27245 | TTTTCATGTTCGTTTTATGG | 27264 |
| 329538 | 16 | 27751 | GTTTCATGTTCGTTTAGACT | 27770 |
| 329539 | 16 | 28084 | TTAATTTGTTCGTTTATTTA | 28103 |
| 348236 | 29752 | 2 | GGGTAGGTAAAAACCTAATA | 29833 |
| 348468 | 29752 | 257 | AAGGCTCTCCATCTTACCTT | 261 |
| 348469 | 29752 | 21484 | GAAAATAAACATGTTCGTTT | 21488 |
| 348470 | 29752 | 25260 | AAACAAATCCATAAGTTCGT | 25264 |
| 348471 | 29752 | 25681 | AGTTGGCATCATAAAGTAAT | 25685 |
| 348472 | 29752 | 26109 | GAATGAGTACATAAGTTCGT | 26113 |
| 348473 | 29752 | 26390 | GTTGTCTGCCATGATAAGCA | 26394 |
| 348474 | 29752 | 27066 | AAGATGAAACATCTGTTGTC | 27070 |
| 348475 | 29752 | 27265 | AATAATTTTCATGTTCGTTT | 27269 |
| 348476 | 29752 | 28112 | ATTATCAGACATTTTAATTT | 28116 |
| 348477 | 29752 | 28122 | ATTGGGGTCCATTATCAGAC | 28126 |
| 348478 | 29752 | 248 | CATCTTACCTTTCGGTCACA | 252 |
| 348479 | 29752 | 21475 | CATGTTCGTTTAGTTGTTAA | 21479 |
| 348480 | 29752 | 25251 | CATAAGTTCGTTTATGTGTA | 25255 |
| 348481 | 29752 | 25672 | CATAAAGTAATGGGTTCTTG | 25676 |
| 348482 | 29752 | 26100 | CATAAGTTCGTACTCACTTT | 26104 |
| 348483 | 29752 | 26381 | CATGATAAGCAATGTTAAAG | 26385 |
| 348484 | 29752 | 27057 | CATCTGTTGTCACTTACTGT | 27061 |
| 348485 | 29752 | 27256 | CATGTTCGTTTTATGGATAA | 27260 |
| 348486 | 29752 | 28103 | CATTTTAATTTGTTCGTTTA | 28107 |
| 348487 | 29752 | 28113 | CATTATCAGACATTTTAATT | 28117 |
| 348488 | 29752 | 235 | GGTCACACCCGGACGAAACC | 239 |
| 348489 | 29752 | 21462 | TTGTTAACAAGAATATCACT | 21466 |
| 348490 | 29752 | 25238 | ATGTGTAATGTAAT1TGACA | 25242 |
| 348491 | 29752 | 25659 | GTTCTTGGATTTGCACTTCC | 25663 |
| 348492 | 29752 | 26087 | TCACTTTCTTGTGCTTACAA | 26091 |
| 348493 | 29752 | 26368 | GTTAAAGTTCCAAACAGAAT | 26372 |
| 348494 | 29752 | 27044 | TTACTGTACTAGCAAAGCAA | 27048 |
| 348495 | 29752 | 27243 | TGGATAATCTAACTCCATAG | 27247 |
| 348496 | 29752 | 28090 | TCGTTTATTTAAAACAACAA | 28094 |
| 348497 | 29752 | 28100 | TTTAATTTGTTCGTTTATTT | 28104 |

Another series of compounds targeting SARS are shown in Table 4. "Target site" indicates the first (5'-most) nucleotide number on the particular target sequence to which the compound binds. All compounds in Table 4 are composed of 2'-O-methoxyethyl nucleotides, also known as 2'-MOE. The internucleoside (backbone) linkages are phosphodiester (P═O) throughout the oligonucleotide. All cytidine residues are 5-methylcytidines.

TABLE 4

Uniform 2'-MOE phosphodiester oligonucleotides targeting SARS

| ISIS # | TARGET SEQ ID NO | TARGET | SEQUENCE (5' to 3') | SEQ ID NO |
|---|---|---|---|---|
| 329720 | 16 | 13377 | ACACCGCAAACCCGTTTAAA | 13396 |
| 329721 | 16 | 13385 | CTGCACTTACACCGCAAACC | 13404 |

TABLE 4-continued

Uniform 2'-MOE phosphodiester oligonucleotides targeting SARS

| ISIS # | TARGET SEQ ID NO | TARGET | SEQUENCE (5' to 3') | SEQ ID NO |
|---|---|---|---|---|
| 329722 | 16 | 13392 | AGACGGGCTGCACTTACACC | 13411 |
| 329724 | 16 | 13396 | TGTAAGACGGGCTGCACTTA | 13415 |
| 329727 | 16 | 13426 | GACATCAGTACTAGTGCCTG | 13445 |
| 329729 | 16 | 13445 | TATCAAAAGCCCTGTAGACG | 13464 |
| 329731 | 16 | 13452 | TTGTAAATATCAAAAGCCCT | 13471 |
| 332768 | 29752 | 13418 | AGACGGGCT | 29834 |
| 334923 | 29752 | 13378 | AAACGTTGATGCATC | 29835 |
| 334924 | 29752 | 13379 | AAAACGTTGATGCAT | 29836 |
| 334925 | 29752 | 13380 | AAAAACGTTGATGCA | 29837 |
| 334926 | 29752 | 13381 | TAAAAACGTTGATGC | 29838 |
| 334927 | 29752 | 13382 | TTAAAAACGTTGATG | 29839 |
| 334928 | 29752 | 13383 | TTTAAAAACGTTGAT | 29840 |
| 334929 | 29752 | 13384 | GTTTAAAAACGTTGA | 29841 |
| 334930 | 29752 | 13385 | CGTTTAAAAACGTTG | 29842 |
| 334931 | 29752 | 13386 | CCGTTTAAAAACGTT | 29843 |
| 334932 | 29752 | 13387 | CCCGTTTAAAAACGT | 29844 |
| 334933 | 29752 | 13388 | ACCCGTTTAAAAACG | 29845 |
| 334934 | 29752 | 13389 | AACCCGTTTAAAAAC | 29846 |
| 334935 | 29752 | 13390 | AAACCCGTTTAAAAA | 29847 |
| 334936 | 29752 | 13391 | CAAACCCGTTTAAAA | 29848 |
| 334937 | 29752 | 13392 | GCAAACCCGTTTAAA | 29849 |
| 334938 | 29752 | 13393 | CGCAAACCCGTTTAA | 29850 |
| 334939 | 29752 | 13394 | CCGCAAACCCGTTTA | 29851 |
| 334940 | 29752 | 13395 | ACCGCAAACCCGTTT | 29852 |
| 334941 | 29752 | 13396 | CACCGCAAACCCGTT | 29853 |
| 334942 | 29752 | 13397 | ACACCGCAAACCCGT | 29854 |
| 334943 | 29752 | 13398 | TACACCGCAAACCCG | 29855 |
| 334944 | 29752 | 13399 | TTACACCGCAAACCC | 29856 |
| 334945 | 29752 | 13400 | CTTACACCGCAAACC | 29857 |
| 334946 | 29752 | 13401 | ACTTACACCGCAAAC | 29858 |
| 334947 | 29752 | 13402 | CACTTACACCGCAAA | 29859 |
| 334948 | 29752 | 13403 | GCACTTACACCGCAA | 29860 |
| 334949 | 29752 | 13404 | TGCACTTACACCGCA | 29861 |
| 334950 | 29752 | 13405 | CTGCACTTACACCGC | 29862 |
| 334951 | 29752 | 13406 | GCTGCACTTACACCG | 29863 |
| 334952 | 29752 | 13407 | GGCTGCACTTACACC | 29864 |
| 334953 | 29752 | 13408 | GGGCTGCACTTACAC | 29865 |
| 334954 | 29752 | 13409 | CGGGCTGCACTTACA | 29866 |
| 334955 | 29752 | 13410 | ACGGGCTGCACTTAC | 29867 |
| 334956 | 29752 | 13411 | GACGGGCTGCACTTA | 29868 |
| 334957 | 29752 | 13412 | AGACGGGCTGCACTT | 29869 |
| 334958 | 29752 | 13413 | AAGACGGGCTGCACT | 29870 |
| 334959 | 29752 | 13414 | TAAGACGGGCTGCAC | 29871 |
| 334960 | 29752 | 13415 | GTAAGACGGGCTGCA | 29872 |
| 334961 | 29752 | 13416 | TGTAAGACGGGCTGC | 29873 |
| 334962 | 29752 | 13417 | GTGTAAGACGGGCTG | 29874 |
| 334963 | 29752 | 13418 | GGTGTAAGACGGGCT | 29875 |
| 334964 | 29752 | 13419 | CGGTGTAAGACGGGC | 29876 |
| 334965 | 29752 | 13420 | ACGGTGTAAGACGGG | 29877 |
| 334966 | 29752 | 13421 | CACGGTGTAAGACGG | 29878 |
| 334967 | 29752 | 13422 | GCACGGTGTAAGACG | 29879 |
| 334968 | 29752 | 13423 | CGCACGGTGTAAGAC | 29880 |
| 334969 | 29752 | 13424 | CCGCACGGTGTAAGA | 29881 |
| 334970 | 29752 | 13425 | GCCGCACGGTGTAAG | 29882 |
| 334971 | 29752 | 13426 | TGCCGCACGGTGTAA | 29883 |
| 334972 | 29752 | 13427 | GTGCCGCACGGTGTA | 29884 |
| 334973 | 29752 | 13428 | TGTGCCGCACGGTGT | 29885 |
| 334974 | 29752 | 13429 | CTGTGCCGCACGGTG | 29886 |
| 334975 | 29752 | 13430 | CCTGTGCCGCACGGT | 29887 |
| 334976 | 29752 | 13431 | GCCTGTGCCGCACGG | 29888 |
| 334977 | 29752 | 13432 | TGCCTGTGCCGCACG | 29889 |
| 334978 | 29752 | 13433 | GTGCCTGTGCCGCAC | 29890 |
| 334979 | 29752 | 13434 | AGTGCCTGTGCCGCA | 29891 |
| 334980 | 29752 | 13435 | TAGTGCCTGTGCCGC | 29892 |
| 334981 | 29752 | 13436 | CTAGTGCCTGTGCCG | 29893 |
| 334982 | 29752 | 13437 | ACTAGTGCCTGTGCC | 29894 |
| 334983 | 29752 | 13438 | TACTAGTGCCTGTGC | 29895 |
| 334984 | 29752 | 13439 | GTACTAGTGCCTGTG | 29896 |
| 334985 | 29752 | 13440 | AGTACTAGTGCCTGT | 29897 |
| 334986 | 29752 | 13441 | CAGTACTAGTGCCTG | 29898 |
| 334987 | 29752 | 13442 | TCAGTACTAGTGCCT | 29899 |

TABLE 4-continued

Uniform 2'-MOE phosphodiester oligonucleotides targeting SARS

| ISIS # | TARGET SEQ ID NO | TARGET SITE | SEQUENCE (5' to 3') | SEQ ID NO |
|---|---|---|---|---|
| 334988 | 29752 | 13443 | ATCAGTACTAGTGCC | 29900 |
| 334989 | 29752 | 13444 | CATCAGTACTAGTGC | 29901 |
| 334990 | 29752 | 13445 | ACATCAGTACTAGTG | 29902 |
| 334991 | 29752 | 13446 | GACATCAGTACTAGT | 29903 |
| 334992 | 29752 | 13447 | CGACATCAGTACTAG | 29904 |
| 334993 | 29752 | 13448 | ACGACATCAGTACTA | 29905 |
| 334994 | 29752 | 13449 | GACGACATCAGTACT | 29906 |
| 334995 | 29752 | 13450 | AGACGACATCAGTAC | 29907 |
| 334996 | 29752 | 13451 | TAGACGACATCAGTA | 29908 |
| 334997 | 29752 | 13452 | GTAGACGACATCAGT | 29909 |
| 334998 | 29752 | 13453 | TGTAGACGACATCAG | 29910 |
| 334999 | 29752 | 13454 | CTGTAGACGACATCA | 29911 |
| 335000 | 29752 | 13455 | CCTGTAGACGACATC | 29912 |
| 335001 | 29752 | 13456 | CCCTGTAGACGACAT | 29913 |
| 335002 | 29752 | 13457 | GCCCTGTAGACGACA | 29914 |
| 335003 | 29752 | 13458 | AGCCCTGTAGACGAC | 29915 |
| 335004 | 29752 | 13459 | AAGCCCTGTAGACGA | 29916 |
| 335005 | 29752 | 13460 | AAAGCCCTGTAGACG | 29917 |
| 335006 | 29752 | 13461 | AAAAGCCCTGTAGAC | 29918 |
| 335007 | 29752 | 13462 | CAAAAGCCCTGTAGA | 29919 |
| 335008 | 29752 | 13463 | TCAAAAGCCCTGTAG | 29920 |
| 335009 | 29752 | 13464 | ATCAAAAGCCCTGTA | 29921 |
| 335010 | 29752 | 13465 | TATCAAAAGCCCTGT | 29922 |
| 335011 | 29752 | 13466 | ATATCAAAAGCCCTG | 29923 |
| 335012 | 29752 | 13467 | AATATCAAAAGCCCT | 29924 |
| 335013 | 29752 | 13468 | AAATATCAAAAGCCC | 29925 |
| 335014 | 29752 | 13469 | TAAATATCAAAAGCC | 29926 |
| 335015 | 29752 | 13470 | GTAAATATCAAAAGC | 29927 |
| 335016 | 29752 | 13471 | TGTAAATATCAAAAG | 29928 |
| 335017 | 29752 | 13472 | TTGTAAATATCAAAA | 29929 |
| 335018 | 29752 | 13473 | GTTGTAAATATCAAA | 29930 |
| 335019 | 29752 | 13474 | CGTTGTAAATATCAA | 29931 |
| 335020 | 29752 | 13475 | TCGTTGTAAATATCA | 29932 |
| 335021 | 29752 | 13476 | TTCGTTGTAAATATC | 29933 |
| 339281 | 29752 | 13448 | TGTAGACGACATCAGTACTA | 13452 |
| 339282 | 29752 | 13449 | CTGTAGACGACATCAGTACT | 13453 |
| 339283 | 29752 | 13450 | CCTGTAGACGACATCAGTAC | 13454 |
| 339284 | 29752 | 13451 | CCCTGTAGACGACATCAGTA | 13455 |
| 339285 | 29752 | 13452 | GCCCTGTAGACGACATCAGT | 13456 |
| 339286 | 29752 | 13453 | AGCCCTGTAGACGACATCAG | 13457 |
| 339287 | 29752 | 13454 | AAGCCCTGTAGACGACATCA | 13458 |
| 339288 | 29752 | 13455 | AAAGCCCTGTAGACGACATC | 13459 |
| 339289 | 29752 | 13456 | AAAAGCCCTGTAGACGACAT | 13460 |
| 339290 | 29752 | 13457 | CAAAAGCCCTGTAGACGACA | 13461 |
| 339291 | 29752 | 13458 | TCAAAAGCCCTGTAGACGAC | 13462 |
| 339292 | 29752 | 13459 | ATCAAAAGCCCTGTAGACGA | 13463 |
| 339293 | 29752 | 13461 | ATATCAAAAGCCCTGTAGAC | 13465 |
| 339294 | 29752 | 13462 | AATATCAAAAGCCCTGTAGA | 13466 |
| 339295 | 29752 | 13463 | AAATATCAAAAGCCCTGTAG | 13467 |
| 339296 | 29752 | 13464 | TAAATATCAAAAGCCCTGTA | 13468 |
| 339297 | 29752 | 13465 | GTAAATATCAAAAGCCCTGT | 13469 |
| 339298 | 29752 | 13466 | TGTAAATATCAAAAGCCCTG | 13470 |

ISIS 329733, also a uniform 2'-MOE oligonucleotide with a phosphodiester backbone (AGTAGGCT, incorporated herein as SEQ ID NO:29934), was designed to target site 13398 of the sequence with Genbank accession number NC_004718.1 (SEQ ID NO:16). This 9-mer mimics one side of stem 2 and part of stem 1, and is designed to disrupt the pseudoknot by binding to one side of stem 2 and coaxially stacked nucleotides in stem 1, and as such, is not antisense to a contiguous nucleotide stretch on the target sequence.

Another series of compounds targeting SARS are shown in Table 5. "Target site" indicates the first (5'-most) nucleotide number on the particular target sequence to which the compound binds. All compounds in Table 5 are composed of 2'-O-methoxyethyl nucleotides, also known as 2'-MOE. The internucleoside (backbone) linkages are phosphorothioate (P=S) throughout the oligonucleotide. All cytidine residues are 5-methylcytidines.

TABLE 5

Uniform 2'-MOE phosphorothioate oligonucleotides targeting SARS

| ISIS # | TARGET SEQ ID NO | TARGET | SEQUENCE (5' to 3') | SEQ ID NO |
|---|---|---|---|---|
| 329540 | 16 | 1 | GGTTGGCTTTTCCTGGGTAG | 20 |
| 329541 | 16 | 2 | TGGTTGGCTTTTCCTGGGTA | 21 |
| 329542 | 29737 | 1 | GGTAGGTAAAAACCTAATAT | 29831 |
| 329543 | 29739 | 1 | TGGTTGCGAAAATAAAGGGG | 29832 |
| 329545 | 29739 | 13377 | ACACCGCAAACCCGTTTAAA | 13396 |
| 329546 | 16 | 13385 | CTGCACTTACACCGCAAACC | 13404 |
| 329547 | 16 | 13392 | AGACGGGCTGCACTTACACC | 13411 |
| 329548 | 16 | 13396 | TGTAAGACGGGCTGCACTTA | 13415 |
| 329549 | 16 | 13426 | GACATCAGTACTAGTGCCTG | 13445 |
| 329550 | 16 | 13445 | TATCAAAAGCCCTGTAGACG | 13464 |
| 329551 | 16 | 13452 | TTGTAAATATCAAAAGCCCT | 13471 |
| 329552 | 16 | 45 | TTTTAAAGTTCGTTTAGAGA | 64 |
| 329553 | 16 | 21464 | TAAACATGTTCGTTTAGTTG | 21483 |
| 329554 | 16 | 25238 | TCCATAAGTTCGTTTATGTG | 25257 |
| 329555 | 16 | 26087 | TACATAAGTTCGTACTCACT | 26106 |
| 329556 | 16 | 26326 | ATAGTTAGTTCGTTTAGACC | 26345 |
| 329557 | 16 | 26891 | AGAAAGCGTTCGTGATGTAG | 26910 |
| 329558 | 16 | 27245 | TTTTCATGTTCGTTTTATGG | 27264 |
| 329559 | 16 | 27751 | GTTTCATGTTCGTTTAGACT | 27770 |
| 329560 | 16 | 28084 | TTAATTTGTTCGTTTATTTA | 28103 |
| 330674 | 16 | 53 | GTTCGTTTAGAGAACAGATC | 57 |
| 332767 | 29751 | 13418 | AGACGGGCT | 29834 |
| 348237 | 29752 | 2 | GGGTAGGTAAAAACCTAATA | 29833 |
| 348240 | 29752 | 3 | TGGGTAGGTAAAAACCTAAT | 29936 |
| 348241 | 29752 | 4 | CTGGGTAGGTAAAAACCTAA | 29937 |
| 348242 | 29752 | 5 | CCTGGGTAGGTAAAAACCTA | 29938 |
| 348243 | 29752 | 6 | TCCTGGGTAGGTAAAAACCT | 29939 |
| 348244 | 29752 | 7 | TTCCTGGGTAGGTAAAAACC | 29940 |
| 348245 | 29752 | 8 | TTTCCTGGGTAGGTAAAAAC | 29941 |
| 348246 | 29752 | 9 | TTTTCCTGGGTAGGTAAAAA | 29942 |
| 348247 | 29752 | 10 | CTTTTCCTGGGTAGGTAAAA | 29943 |
| 348248 | 29752 | 11 | GCTTTTCCTGGGTAGGTAAA | 29944 |
| 348249 | 29752 | 12 | GGCTTTTCCTGGGTAGGTAA | 29945 |
| 348250 | 29752 | 13 | TGGCTTTTCCTGGGTAGGTA | 29946 |
| 348251 | 29752 | 14 | TTGGCTTTTCCTGGGTAGGT | 29947 |
| 348252 | 29752 | 15 | GTTGGCTTTTCCTGGGTAGG | 29948 |
| 348253 | 29752 | 18 | TTGGTTGGCTTTTCCTGGGT | 22 |

TABLE 5-continued

Uniform 2'-MOE phosphorothioate oligonucleotides targeting SARS

| ISIS # | TARGET SEQ ID NO | TARGET | SEQUENCE (5' to 3') | SEQ ID NO |
|---|---|---|---|---|
| 348254 | 29752 | 19 | GTTGGTTGGCTTTTCCTGGG | 23 |
| 348255 | 29752 | 20 | GGTTGGTTGGCTTTTCCTGG | 24 |
| 348256 | 29752 | 22 | GAGGTTGGTTGGCTTTTCCT | 26 |
| 348257 | 29752 | 24 | TCGAGGTTGGTTGGCTTTTC | 28 |
| 348258 | 29752 | 26 | GATCGAGGTTGGTTGGCTTT | 30 |
| 348259 | 29752 | 30 | AAGAGATCGAGGTTGGTTGG | 34 |
| 348260 | 29752 | 32 | ACAAGAGATCGAGGTTGGTT | 36 |
| 348261 | 29752 | 34 | CTACAAGAGATCGAGGTTGG | 38 |
| 348262 | 29752 | 36 | ATCTACAAGAGATCGAGGTT | 40 |
| 348263 | 29752 | 38 | AGATCTACAAGAGATCGAGG | 42 |
| 348264 | 29752 | 40 | ACAGATCTACAAGAGATCGA | 44 |
| 348265 | 29752 | 42 | GAACAGATCTACAAGAGATC | 46 |
| 348266 | 29752 | 44 | GAGAACAGATCTACAAGAGA | 48 |
| 348267 | 29752 | 46 | TAGAGAACAGATCTACAAGA | 50 |
| 348268 | 29752 | 48 | TTTAGAGAACAGATCTACAA | 52 |
| 348269 | 29752 | 50 | CGTTTAGAGAACAGATCTAC | 54 |
| 348270 | 29752 | 52 | TTCGTTTAGAGAACAGATCT | 56 |
| 348271 | 29752 | 54 | AGTTCGTTTAGAGAACAGAT | 58 |
| 348528 | 29752 | 257 | AAGGCTCTCCATCTTACCTT | 261 |
| 348529 | 29752 | 21484 | GAAAATAAACATGTTCGTTT | 21488 |
| 348530 | 29752 | 25260 | AAACAAATCCATAAGTTCGT | 25264 |
| 348531 | 29752 | 25681 | AGTTGGCATCATAAAGTAAT | 25685 |
| 348532 | 29752 | 26109 | GAATGAGTACATAAGTTCGT | 26113 |
| 348533 | 29752 | 26390 | GTTGTCTGCCATGATAAGCA | 26394 |
| 348534 | 29752 | 27066 | AAGATGAAACATCTGTTGTC | 27070 |
| 348535 | 29752 | 27265 | AATAATTTTCATGTTCGTTT | 27269 |
| 348536 | 29752 | 28112 | ATTATCAGACATTTTAATTT | 28116 |
| 348537 | 29752 | 28122 | ATTGGGGTCCATTATCAGAC | 28126 |
| 348538 | 29752 | 248 | CATCTTACCTTTCGGTCACA | 252 |
| 348539 | 29752 | 21475 | CATGTTCGTTTAGTTGTTAA | 21479 |
| 348540 | 29752 | 25251 | CATAAGTTCGTTTATGTGTA | 25255 |
| 348541 | 29752 | 25672 | CATAAAGTAATGGGTTCTTG | 25676 |
| 348542 | 29752 | 26100 | CATAAGTTCGTACTCACTTT | 25104 |
| 348543 | 29752 | 26381 | CATGATAAGCAATGTTAAAG | 26385 |
| 348544 | 29752 | 27057 | CATCTGTTGTCACTTACTGT | 26061 |
| 348545 | 29752 | 27256 | CATGTTCGTTTTATGGATAA | 27260 |
| 348546 | 29752 | 28103 | CATTTTAATTTGTTCGTTTA | 28107 |

TABLE 5-continued

Uniform 2'-MOE phosphorothioate oligonucleotides targeting SARS

| ISIS # | TARGET SEQ ID NO | TARGET SITE | SEQUENCE (5' to 3') | SEQ ID NO |
|---|---|---|---|---|
| 348547 | 29752 | 28113 | CATTATCAGACATTTTAATT | 28117 |
| 348548 | 29752 | 235 | GGTCACACCCGGACGAAACC | 239 |
| 348549 | 29752 | 21462 | TTGTTAACAAGAATATCACT | 21466 |
| 348550 | 29752 | 25238 | ATGTGTAATGTAATTTGACA | 25242 |
| 348551 | 29752 | 25659 | GTTCTTGGATTTGCACTTCC | 25663 |
| 348552 | 29752 | 26087 | TCACTTTCTTGTGCTTACAA | 26091 |
| 348553 | 29752 | 26368 | GTTAAAGTTCCAAACAGAAT | 26372 |
| 348554 | 29752 | 27044 | TTACTGTACTAGCAAAGCAA | 27048 |
| 348555 | 29752 | 27243 | TGGATAATCTAACTCCATAG | 27247 |
| 348556 | 29752 | 28090 | TCGTTTATTTAAAACAACAA | 28094 |
| 348557 | 29752 | 28100 | TTTAATTTGTTCGTTTATTT | 28104 |
| 329544 | 29752 | 1 | ATGATGTTGAGCTGGTTGCGAAAATAAAGGGG | 29935 |

ISIS 329591, also a uniform 2'-MOE oligonucleotide with a phosphorothioate backbone (AGTAGGGCT, incorporated herein as SEQ ID NO:29934), was designed to target site 13398 of the sequence with Genbank accession number NC_004718.1 (SEQ ID NO:16). This 9-mer mimics one side of stem 2 and part of stem 1, and is designed to disrupt the pseudoknot by binding to one side of stem 2 and coaxially stacked nucleotides in stem 1, and as such, is not antisense to a contiguous nucleotide stretch on the target sequence.

Another series of compounds targeting SARS are shown in Table 6. "Target site" indicates the first (5'-most) nucleotide number on the particular target sequence to which the compound binds. All compounds in Table 6 are LNAs. The internucleoside (backbone) linkages are phosphodiester (P=O) throughout the oligonucleotide. All cytidine residues are 5-methylcytidines.

TABLE 6

LNA oligonucleotides targeting SARS

| ISIS # | TARGET SEQ ID NO | TARGET SITE | SEQUENCE (5' to 3') | SEQ ID NO |
|---|---|---|---|---|
| 339335 | 29752 | 13453 | TGTAGACGACATCAG | 29949 |
| 339336 | 29752 | 13456 | CCCTGTAGACGACAT | 29950 |

Oligonucleotides disclosed herein can be designed and used to target particular features or structural attributes of the SARS Co-V. The series of oligonucleotides ISIS 329410 to ISIS 329419 targets sites conserved between SARS and at least one other coronavirus. The series ISIS 329424 to ISIS 329523 targets randomly selected sites conserved among SARS variants. ISIS 329420 to ISIS 329423 and ISIS 329540 to ISIS 329544 target the 5' end of the positive strand of at least one of the full-length variants. ISIS 329524 to ISIS 329530, ISIS 329545 to ISIS 329551, ISIS 329720 to ISIS 329722, ISIS 329724, ISIS 329727, ISIS 329729 and ISIS 329731 target sites in or near the pseudoknot. ISIS 332767 and ISIS 332768 are 9-mers targeting the end of stem 1 and stem 2 of the pseudoknot. ISIS 329531 to ISIS 329539 and ISIS 329552 to ISIS 329560 target possible primer binding sites. ISIS 330674 is designed to prevent hybridization of the leader by targeting the 3' end of the leader sequence.

ISIS 329591 (AGTAGGGCT, incorporated herein as SEQ ID NO:29934), a uniform 2'-MOE oligonucleotide with a phosphorothioate backbone, and ISIS 329733, a uniform 2'-MOE oligonucleotide with a phosphodiester backbone (AGTAGGGCT, SEQ ID NO:29934), were designed to site 13398 of the sequence with Genbank accession number NC_004718.1 (SEQ ID NO:16). These 9-mers mimic one side of stem 2 and part of stem 1, and are designed to disrupt the pseudoknot by binding to one side of stem 2 and coaxially stacked nucleotides in stem 1.

Example 19

RNA/DNA Duplexes Targeting SARS Co-V

In accordance with the present invention, a series of nucleic acid duplexes comprising the antisense compounds of the present invention and their complements were designed to target SARS with siRNA. The ends of the strands have been modified by the addition of one or more nucleobases to form an overhang. The sense strand of the dsRNA is then designed and synthesized as the complement of the antisense strand and also contains additions to the 3'-terminus. Thus, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:1) and having a two-nucleobase overhang of deoxythymidine(dT) would have the following structure:

```
cgagaggcggacgggaccgTT   Antisense Strand
|||||||||||||||||||     (SEQ ID NO:2)
TTgctctccgcctgccctggc   Complement Strand
                        (SEQ ID NO:3)
```

Once synthesized, the complementary strands are annealed. The duplex compounds targeting SARS are shown in Table 7. Each antisense oligonucleotide is immediately followed by its complement in Table 7. "Target site" indicates the first (5'-most) nucleotide number on the particular target sequence to which the antisense strand of the compound binds. All antisense compounds and their complements in Table 5 are oligonucleotides composed of a central region consisting of ribonucleotides, flanked on the 3' end with 2 2'-deoxyribonucleotides (shown in BOLD). The internucleoside (backbone) linkages are phosphodiester (P=O) throughout the antisense oligonucleotide and the complement sequence of the duplex.

TABLE 7

Full oligonucleotide duplexes with 3'-overhangs targeting SARS

| ISIS # | STRAND | TARGET SEQ ID NO | TARGET SITE | SEQUENCE (5' to 3') | SEQ ID NO |
|---|---|---|---|---|---|
| 329608 | Antisense | 16 | 190 | UGAUGAUCGACUGCAACACGG | 29951 |
| 329598 | Complement | 16 | 190 | GUGUUGCAGUCGAUCAUCAGC | 29952 |
| 329609 | Antisense | 16 | 2732 | GAACUUCCCAAACAGUAUCTT | 29953 |
| 329599 | Complement | 16 | 2732 | GAUACUGUUUGGGAAGUUCAA | 29954 |
| 329610 | Antisense | 16 | 5622 | AAUGUACCUUGCUGUAAUUTA | 29955 |
| 329600 | Complement | 16 | 5622 | AAUUACAGCAAGGUACAUUCT | 29956 |
| 329611 | Antisense | 16 | 8004 | GUAGCAACAAGUGCCUUAAGT | 29957 |
| 329601 | Complement | 16 | 8004 | UUAAGGCACUUGUUGCUACAG | 29958 |
| 329612 | Antisense | 16 | 10775 | UACCAUUCUGCAGCAGCUCTT | 29959 |
| 329602 | Complement | 16 | 10775 | GAGCUGCUGCAGAAUGGUATG | 29960 |
| 329613 | Antisense | 16 | 13606 | UAACCAAGUUAUAAAUAGUCT | 29961 |
| 329603 | Complement | 16 | 13606 | ACUAUUUAUAACUUGGUUAAA | 29962 |
| 329614 | Antisense | 16 | 17717 | GGCAAUCCUAAGAUUUUUGAA | 29963 |
| 329604 | Complement | 16 | 17717 | CAAAAAUCUUAGGAUUGCCTA | 29964 |
| 329615 | Antisense | 16 | 21351 | UUGAUUCUCCUUAAGAGACAT | 29965 |
| 329605 | Complement | 16 | 21351 | GUCUCUUAAGGAGAAUCAAAT | 29966 |
| 329616 | Antisense | 16 | 25897 | UCUGUAGUAAUUUGUGUAGAC | 29967 |
| 329606 | Complement | 16 | 25897 | CUACACAAAUUACUACAGACA | 29968 |
| 329617 | Antisense | 16 | 27892 | AAAGCCAAGCAGUGCUAUAAG | 29969 |
| 329607 | Complement | 16 | 27892 | UAUAGCACUGCUUGGCUUUGT | 29970 |

The siRNA duplexes disclosed in Table 7 target randomly selected sites conserved among SARS variants.

Example 20

Antisense Inhibition of the SARS-CoV with Oligonucleotides Complentary to the Negative Strand of the Virus Compounds targeting SARS are shown in Table 8. "Target site" indicates the first (5'-most) nucleotide number on the particular target sequence to which the compound binds. All compounds in Table 8 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-O-methoxyethyl nucleotides, also known as 2'-MOE. The internucleoside (backbone) linkages are phosphorothioate (P=S) throughout the oligonucleotide. All cytidine residues are 5-methylcytidines.

TABLE 8

Chimeric phosphorothioate oligonucleotides targeted to SARS

| ISIS # | TARGET SEQ ID NO | TARGET SITE | SEQUENCE (5' to 3') | SEQ ID NO |
|---|---|---|---|---|
| 329561 | 16 | 192 | GTGTTGCAGTCGATCATCAG | 29971 |
| 329562 | 16 | 1753 | ATTGTTGAGTCCTGCGGTAA | 29972 |
| 329563 | 16 | 2734 | GATACTGTTTGGGAAGTTCA | 29973 |
| 329564 | 16 | 4252 | GAAGCACCTAATGCTAAGGA | 29974 |
| 329565 | 16 | 5624 | AATTACAGCAAGGTACATTC | 29975 |
| 329566 | 16 | 6975 | CGTTAGAGAATTGTATCTTA | 29976 |
| 329567 | 16 | 8006 | TTAAGGCACTTGTTGCTACA | 29977 |
| 329568 | 16 | 9132 | TAGACATGGTACATGCGAAA | 29978 |
| 329569 | 16 | 10777 | GAGCTGCTGCAGAATGGTAT | 29979 |
| 329570 | 16 | 12254 | TAACTAGTGCTATGCAAACA | 29980 |
| 329571 | 16 | 13608 | ACTATTTATAACTTGGTTAA | 29981 |
| 329572 | 16 | 15817 | AACAAGGAGATGATTACGTG | 29982 |
| 329573 | 16 | 17719 | CAAAAATCTTAGGATTGCCT | 29983 |
| 329574 | 16 | 18925 | ATAAGTTTCCAGTTCTTCAT | 29984 |
| 329575 | 16 | 21353 | GTCTCTTAAGGAGAATCAAA | 29985 |
| 329576 | 16 | 23829 | TCACAAATATTACCTGACCC | 29986 |
| 329577 | 16 | 25899 | CTACACAAATTACTACAGAC | 29987 |
| 329578 | 16 | 27130 | TGCTATTTGGAATCTTGACG | 29988 |
| 329579 | 16 | 27894 | TATAGCACTGCTTGGCTTTG | 29989 |
| 329580 | 16 | 29504 | TAATCTCACATAGCAATCTT | 29990 |
| 330481 | 16 | 45 | TCTCTAAACGAACTTTAAAA | 29991 |
| 330482 | 16 | 21464 | CAACTAAACGAACATGTTTA | 29992 |
| 330483 | 16 | 25238 | CACATAAACGAACTTATGGA | 29993 |
| 330484 | 16 | 26087 | AGTGAGTACGAACTTATGTA | 29994 |
| 330485 | 16 | 26326 | GGTCTAAACGAACTAACTAT | 29995 |
| 330486 | 16 | 26891 | CTACATCACGAACGCTTTCT | 29996 |
| 330487 | 16 | 27245 | CCATAAAACGAACATGAAAA | 29997 |
| 330488 | 16 | 27751 | AGTCTAAACGAACATGAAAC | 29998 |
| 330489 | 16 | 28084 | TAAATAAACGAACAAATTAA | 29999 |

Another series of compounds targeting SARS is shown in Table 9. "Target site" indicates the first (5'-most) nucleotide number on the particular target sequence to which the compound binds. All compounds in Table 9 are composed of 2'-O-methoxyethyl nucleotides, also known as 2'-MOE. The internucleoside (backbone) linkages are phosphodiester (P=O) throughout the oligonucleotide. All cytidine residues are 5-methylcytidines.

TABLE 9

Uniform 2'-MOE phosphodiester oligonucleotides targeting SARS

| ISIS # | TARGET SEQ ID NO | TARGET SITE | SEQUENCE (5' to 3') | SEQ ID NO |
|---|---|---|---|---|
| 329581 | 29752 | 16 | CTACCCAGGAAAAGCCAACC | 30000 |
| 329582 | 29752 | 17 | TACCCAGGAAAAGCCAACCA | 30001 |
| 329583 | 29737 | 1 | ATATTAGGTTTTTACCTACC | 30002 |
| 329584 | 29739 | 1 | CCCCTTTATTTTCGCAACCA | 30003 |
| 329585 | 29739 | 1 | CCCCTTTATTTTCGCAACCAGCTCAACATCAT | 30004 |
| 330490 | 16 | 45 | TCTCTAAACGAACTTTAAAA | 30005 |

TABLE 9-continued

Uniform 2'-MOE phosphodiester oligonucleotides targeting SARS

| ISIS # | TARGET SEQ ID NO | TARGET SITE | SEQUENCE (5' to 3') | SEQ ID NO |
|---|---|---|---|---|
| 330491 | 16 | 21464 | CAACTAAACGAACATGTTTA | 30006 |
| 330492 | 16 | 25238 | CACATAAACGAACTTATGGA | 30007 |
| 330493 | 16 | 26087 | AGTGAGTACGAACTTATGTA | 30008 |
| 330494 | 16 | 26326 | GGTCTAAACGAACTAACTAT | 30009 |
| 330495 | 16 | 26891 | CTACATCACGAACGCTTTCT | 30010 |
| 330496 | 16 | 27245 | CCATAAAACGAACATGAAAA | 30011 |
| 330497 | 16 | 27751 | AGTCTAAACGAACATGAAAC | 30012 |
| 330498 | 16 | 28084 | TAAATAAACGAACAAATTAA | 30013 |

Oglionucleotides dislosed herein can be designed and used to target particular features or structural attributes of the SARS Co-V. The series ISIS 329561 to 329580 targets randomly selected sites conserved among SARS variants. The series ISIS 329581 to ISIS 329585 mimic the 5' end of the positive strand of at least one of the full-length variants. ISIS 330481 to ISIS 330489 and ISIS 330490 to ISIS 330498 target possible primer binding sites.

ISIS 330673 (ATATTAGGTTTTTACCTACCCAGGAAAAGCCAACCAACCTC GATCTCTTGTAGATCTGTTCTCTAAACGAAC, incorporated herein as SEQ ID NO:30014), which targets site 1 of the sequence with Genbank accession number AY274119.3 (SEQ ID NO:29751), is a uniform 2'-MOE oligonucleotide with phosphorothioate backbone (P=S), and a single 3' dideoxy nucleotide. This oligonucleotide is a 72-mer mimic of the leader sequence with a non-extendable 3' end.

Example 21

Control Oligonucleotides for SARS Experiments

The control oligonucleotides for the experiments are listed in Table 10.

Except for ISIS 289606, 329586 and 329587 which are uniform 2'-MOE oligonucleotides with phosphorothioate (P=S) backbones, and ISIS 329804, which is a uniform 2'-MOE oligonucleotide with a phosphodiester (P=O) backbone, all control compounds in Table 10 are "gapmers" 20 nucleotides in length, composed of a central "gap" region consisting of ten 2'-deoxynucleotides, which is flanked on both sides (5' and 3' directions) by five-nucleotide 2'-MOE "wings." The gapmers have phosphorothioate backbones (P=S) and all cytidine residues are 5-methylcytidine.

TABLE 10

Control oligonucleotides

| ISIS # | SEQUENCE (5' to 3') | SEQ ID NO |
|---|---|---|
| 20569 | GTGCGCGCGAGCCCGAAA | 30015 |
| 29837 | TCGATCTCCTTTTATGCCC | 30016 |

TABLE 10-continued

Control oligonucleotides

| ISIS # | SEQUENCE (5' to 3') | SEQ ID NO |
|---|---|---|
| 113529 | CTCTTACTGTGCTGTGGAC | 30017 |
| 114845 | TACGTCCGGAGGCGTACG | 30018 |
| 122291 | TATTCCACGAACGTAGGCT | 30019 |
| 129686 | CGTTATTAACCTCCGTTGA | 30020 |
| 129687 | ACAAGCGTCAACCGTATT | 30021 |
| 129688 | TTCGCGGCTGGACGATTCA | 30022 |
| 129689 | GAGGTCTCGACTTACCCGC | 30023 |
| 129690 | TTAGAATACGTCGCGTTAT | 30024 |
| 129691 | ATGCATACTACGAAAGGC | 30025 |
| 129694 | GTACAGTTATGCGCGGTA | 30026 |
| 129695 | TTCTACCTCGCGCGATTTA | 30027 |
| 129696 | ATTCGCCAGACAACACTG | 30028 |
| 129700 | TAGTGCGGACCTACCCAC | 30029 |
| 141923 | CCTTCCCTGAAGGTTCCTC | 30030 |
| 289606 | CCTTCCCTGAAGGTTCCTC | 30031 |
| 329586 | GTGCGCGCGAGCCCGAAA | 30032 |
| 329587 | TAGTGCGGACCTACCCAC | 30033 |
| 329804 | CCTTCCCTGAAGGTTCCTC | 30034 |

Example 22

Target mRNA Reduction in Vero C1008 Cells

To confirm the feasibility of using antisense oligonucleotides to inhibit target mRNA expression in a cell line permissive for SARS infection, ISIS 116847 (CTGCTAGC-CTCTGGATTTGA, incorporated herein as SEQ ID NO:30035), targeted to PTEN, an endogenous mRNA in Vero C1008 cells, was tested for its ability to inhibit expression. The high homology between monkey and human PTEN allowed for the use of the ISIS 116847, which was designed to target the human PTEN sequence. Also tested were ISIS 289841 (CTAAGCGCTCAATGAACATG, incorporated herein as SEQ ID NO:30036), targeted to human Forkhead box OIA (Forkhead), ISIS 122976 (TTGTCAC-CTTGTGCTCCACA, incorporated herein as SEQ ID NO:30037), targeted to human MEKK3, and ISIS 129690 (TTAGAATACGTCGCGTTATG, incorporated herein as SEQ ID NO:30024), a scrambled control.

ISIS 116847, ISIS 289841, and ISIS 122976 are "gapmers" 20 nucleotides in length, composed of a central "gap" region consisting of ten 2'-deoxynucleotides, which is flanked on both sides (5' and 3' directions) by five-nucleotide 2'-MOE "wings." The gapmers have, phosphorothioate backbones (P=S) and all cytidine residues are 5-methylcytidine.

In addition, siRNA designed to target human PTEN (Dharmacon, Inc., Lafayette, Colo.) were tested. The siRNA was comprised of an antisense strand and a complement strand, which were comprised of 19 ribonucleotides linked by alternating phosphothioate and phosphodiester bonds, and flanked on the 3' end with 2 2'-deoxyribonucleotides (shown in BOLD). For PTEN siRNA, the antisense strand is ISIS 263186 (CTGCTAGCCTCTGGATTTGTT, incorporated herein as SEQ ID NO:30038) and the complement strand is ISIS 263187 (CAAATCCAGAGGCTAGCAGTT, incorporated herein as SEQ ID NO:30039). Also tested were siRNAs targeted to human MEKK3. For MEKK3 siRNA, the antisense strand is ISIS 316404 (TGTCACCTTGT-GCTCCACATC, incorporated herein as SEQ ID NO:30040) and the complement strand is ISIS 316398 (TGTGGAG-CACAAGGTGACAAC, incorporated herein as SEQ ID NO:30041). The primer probe set designed to target the human PTEN was

```
Forward primer:
AATGGCTAAGTGAAGATGACAATCAT      (SEQ ID NO: 30042)

Reverse primer:
TGCACATATCATTACACCAGTTCGT       (SEQ ID NO: 30043)

Probe:
FAM-                            (SEQ ID NO: 30044)
TTGCAGCAATTCACTGTAAAGCTGGAAAGG-
TAMRA,
``` where FAM is the fluorescent reporter dye and TAMRA is the quencher dye.

The African green monkey normal kidney cell line Vero C1008 (also known as Vero E6) was obtained from the American Type Culture Collection (Manassas, Va.). (Vero C1008 is a clone of Vero 76 which is also obtained from the American Type Culture Collection (Manassas, Va.), and can be cultured under the same conditions.) Vero C1008 cells were routinely cultured in DMEM supplemented with 10% fetal bovine serum and 1% penicillin/streptomycin and adjusted to contain 4 mM L-glutamine, 1.5 g/L sodium bicarbonate and 4.5 g/L glucose (Invitrogen Life Technologies, Carlsbad, Calif. Cells were routinely passaged by trypsinization and dilution when they reached 90% confluence, and were seeded onto 96-well plates (Falcon-353047) for use in antisense oligonucleotide transfection. Cells were transfected with 2.5 µg Lipofectin/100 µM oligonucleotide/mL Opti-MEM. The siRNAs were also tested using 5 µg Lipofectin/100 nM oligonucleotide/mL OptiMEM (labeled as 2× in the table). Ribogreen was used to measure total RNA.

Results of the experiment are presented in Table 11 as percent inhibition relative to untreated controls.

TABLE 11

PTEN mRNA Target Reduction in Vero C1008 Cells

| Treatment | % Inhibition Dose of oligonucleotides (nM) | | |
|---|---|---|---|
| | 25 | 50 | 100 |
| 289841 | 10 | 15 | 24 |
| 129690 | 7 | 6 | 8 |
| 116847 | 74 | 86 | 92 |
| 263186 + 263187 | 48 | 48 | 64 |
| 263186 + 263187 2x | 34 | 54 | 82 |
| 122976 | 0 | 0 | 10 |
| si-122976 | 0 | 0 | 0 |
| si-122976 2x | 20 | 0 | 0 |

The results presented in Table 11 show that antisense oligonucleotides targeted to PTEN (ISIS 116847, si-116847) successfully reduce expression in a dose-dependent, target-specific manner in Vero C1008 cells.

Similarly, reduction of Forkhead mRNA was assayed in Vero C1008 Cells.

A primer probe set designed to target human Forkhead is

```
Forward primer:
TGCATTTCGCTACCCGAGTT            (SEQ ID NO: 30045)

Reverse primer:
CATCAACATCAGGCACTTCTCAG         (SEQ ID NO: 30046)

Probe:
FAM-                            (SEQ ID NO: 30047)
CAGTGCAGATTCCACGTTCTTGTTCCGATA-
TAMRA,
``` where FAM is the fluorescent reporter dye and TAMRA is the quencher dye.

Results are presented in Table 12 as percent inhibition relative to untreated control.

TABLE 12

Forkhead mRNA Target Reduction in Vero C1008 Cells

| Treatment | % Inhibition Dose of oligonucleotides (nM) | | |
|---|---|---|---|
| | 25 | 50 | 100 |
| 289841 | 32 | 51 | 81 |
| 129690 | 7 | 15 | 8 |
| 116847 | 17 | 0 | 22 |
| 263186 + 263187 | 33 | 17 | 21 |
| 263186 + 263187 2x | 10 | 3 | 32 |
| 122976 | 6 | 0 | 8 |
| si-122976 | 3 | 8 | 11 |
| si-122976 2x | 42 | 15 | 13 |

The results presented in Table 12 show that ISIS 289841 targeted to Forkhead mRNA successfully reduces expression in a dose-dependent, target-specific manner in Vero C1008 cells.

Example 23

Determination of Non-specific Inhibition of SARS-CoV by Transfection Reagent Methods and Validation of SARS Infection Assay in Vero 76 Cells Transfection reagents were tested for toxicity in Vero 76 cells. Furthermore, control oligonucleotides were tested for efficacy against infection of Vero 76 cells with the Toronto-2 strain of SARS-CoV.

The protocols described indicate volumes were optimized for transfection experiments in 96-well plate format. Reagent volumes can be adjusted to compensate for other cell culture formats.

Oligonucleotide plates were removed from storage and brought to room temperature. Pre-warmed Opti-MEM (Invitrogen Life Technologies, Carlsbad, Calif.) was added to oligonucleotide plates at a volume of 50 μL/well. Plates were agitated to dissolve oligonucleotides (generally a minimum time of 15 minutes). 45 minutes to an hour prior to oligonucleotide transfection, 15 μL of Lipofectin (Invitrogen Life Technologies, Carlsbad, Calif.) was added into 2 mL of Opi-MEM, 20 μL of OligofectAMINE (Invitrogen Life Technologies, Carlsbad, Calif.) was added in 2 mL of Opti-MEM, and 5 μL Cytofectin (Gene Therapy Systems, San Diego, Calif.) was added in 2 mL Opti-MEM. Each mixture was incubated for 30 minutes at room temperature before 75 μL/well of each mixture was added onto appropriate wells of the oligonucleotide plate that contains 200 nM oligonucleotide. The oligonucleotides and transfection reagents were incubated at room temperature for about 15 minutes to allow complex formation.

Media was removed from a 96 well plate containing Vero 76 cells which had been seeded at a density of ~$10^5$ cells/mL. For this assay, cells can be transfected at confluency of about 65-100%. Results presented in Table 13 are from cells transfected at a confluency of about 90-95%. 100 μL/well of oligonucleotide/transfection reagent/Opti-MEM was transferred from the oligonucleotide plate onto the cells. Cells were incubated for 4 hours at which time the transfection reagent was removed and cells were washed once with serum containing growth medium prior to addition of 50 μL assay medium (IMEM containing 2% FBS, L-glutamine, and penicillin/streptomycin) per well. Cells were allowed to recover for at least 2 hours in standard cell culture conditions prior to viral infection.

For viral infection, pre-titred SARS Toronto-2 virus ($2.1 \times 10^8$ pfu/mL) stock, diluted in assay medium and added at a multiplicity of infection of 0.3 to 0.5 or media was added to the wells at 50 μL/well. The plate was incubated for 72 hours in normal cell culture conditions. Quantification of live cells was performed using an MTS reagent (Cell Titer 96 Aqueous One solution, Promega, Madison, Wis.), and the % toxicity and % killing was calculated.

Control oligonucleotides ISIS 129686, ISIS 129689, ISIS 129690, ISIS 129691, ISIS 129694, ISIS 129695, ISIS 129700, and ISIS 141923, described in Example 20 were tested in the above assay for toxicity and efficacy. Results are presented in Table 14 as % toxicity and % viral activity. Toxicity refers to the toxicity due to the transfection reagent or oligonucleotide. Viral activity reflects the ability of the virus to infect the cells, wherein a viral activity greater than 100% would indicate increased virulence and a viral activity less than 100% would indicate inhibition of virulence. Viral activity for virus control was 84%.

TABLE 13

Effect of transfection reagents and control antisense oligonucleotides on SARS activity in Vero 76 cells

| Compound | Transfection Reagent | % Toxicity | % Viral Activity | SEQ ID NO |
|---|---|---|---|---|
| 129686 | Lipofectin | 2.4 | 89 | 30020 |
|  | OligofectAMINE | 2.4 | 92 |  |
|  | Cytofectin | 0.0 | 93 |  |
| 129689 | Lipofectin | 3.7 | 91 | 30023 |
|  | OligofectAMINE | 3.1 | 93 |  |
|  | Cytofectin | 3.9 | 92 |  |
| 129690 | Lipofectin | 7.4 | 88 | 30024 |
|  | OligofectAMINE | 0.9 | 92 |  |
|  | Cytofectin | 3.0 | 93 |  |
| 129691 | Lipofectin | 8.3 | 92 | 30025 |
|  | OligofectAMINE | 6.7 | 92 |  |
|  | Cytofectin | 9.7 | 93 |  |
| 129694 | Lipofectin | 7.7 | 90 | 30026 |
|  | OligofectAMINE | 5.6 | 91 |  |
|  | Cytofectin | 4.6 | 91 |  |
| 129695 | Lipofectin | 6.7 | 91 | 30027 |
|  | OligofectAMINE | 6.2 | 91 |  |
|  | Cytofectin | 5.2 | 92 |  |
| 129700 | Lipofectin | 6.2 | 91 | 30029 |
|  | OligofectAMINE | 10.5 | 91 |  |
|  | Cytofectin | 8.2 | 93 |  |
| 141923 | Lipofectin | 7.7 | 88 | 30030 |
|  | OligofectAMINE | 6.0 | 93 |  |
|  | Cytofectin | 8.2 | 93 |  |

No significant toxicity was observed with any transfection reagent or oligonucleotide used in the assay. None of the test compounds demonstrated efficacy versus the SARS Toronto-2 strain. Thus, the assay was deemed valid for use with the ilogonucleotide/transfection reagent system described. Lipofectin was chosen as the transfection reagent for subsequent studies, and was used at a ratio of 3 μL Lipofectin/100 nM oligonucleotide/1 mL Opti-MEM.

Example 24

Antisense Oligonucleotide Inhibition of SARS Activity in Vero 76 Cells: MTS Assay Antisense oligonucleotides targeting the SARS-CoV gene were tested in the assay described in Example 22, using the Lipofectin reagent (Invitrogen Life Technologies, Carlsbad, Calif.) at 3 μL Lipofectin/100 nM oligonucleotide/1 mL Opti-MEM.

The experiment consisted of 4 plates containing the compounds, and each plate was tested in duplicate yielding a total of 8 plates. Each plate contained 12 negative control oligonucleotides: ISIS 129686, 129687, 129688, 129689, 129690, 129691, 129694, 129695, 141923, 289606, 329586, 329804, indicated in bold in the table. Included in the assay were the 5-10-5 MOE gapmers ISIS 330538 (ATAAAT-TATTTCTGTGGCTG, incorporated herein as SEQ ID NO:30048) targeted to CEACAMI, and ISIS 333040 (TTGAGCTTCTTGCTGTGGAT, incorporated herein as SEQ ID NO:30049), ISIS 333048 (CATGATGTCCCG-CACGGTGG, incorporated herein as SEQ ID NO:30050), ISIS 333049 AATAGCCCGTCACATTGAGG, incorporated herein as SEQ ID NO:30051), ISIS 333054 (AC-CCACTTGATGTTGGCTTT, incorporated here in as SEQ ID NO:30052), and ISIS 333057 (GCTGTTTTCTGT-GAACCACT, incorporated herein as SEQ ID NO:30053) targeted to aminopeptidase N. Also contemplated as a control is ISIS 2922 (GCGTTTGCTCTTCTTCTTGCG, incorporated herein as SEQ ID NO:30054), a uniform 2'-deoxynucleotide with a phosphothioate backbone designed to human herpesvirus 5. Data are presented as the average of two O.D. measurements (Envision microplate reader, Perkin-Elmer) per antisense oligonucleotide tested. The replicate plates averaged for each data point are indicated in Table 14 "Plates." Each plate contained 4 of each of the following control wells: media alone with no cells (Media), media and virus with no cells (Media+Virus), cells alone with no virus or oligonucleotide treatment (Cell Control), and cells and virus with no oligonucleotide treatment (Virus Control). The O.D. presented for each of these controls is thus the average of eight measurements for each set of duplicate plates. Because the O.D. measured is proportional to the number of living cells in culture, the O.D. is indicative of "viral activity", wherein an O.D. reading close to that for the Cell Control suggests inhibition of virus activity by the treatment, and an O.D. reading close to that for the Virus Control suggest no affect on virus activity.

TABLE 14

Effect of antisense inhibitors on SARS activity in Vero 76 cells: MTS assay

| Plates | Treatment (ISIS # or description) | Viral activity (O.D.) | SEQ ID NO |
|---|---|---|---|
| A + B | Media | 0.09 | N/A |
| A + B | Media + V | 0.09 | N/A |
| A + B | CC | 0.87 | N/A |
| A + B | VC | 0.46 | N/A |
| A + B | 129686 | 0.50 | 30020 |
| A + B | 129687 | 0.55 | 30021 |
| A + B | 129688 | 0.52 | 30022 |
| A + B | 129689 | 0.52 | 30023 |
| A + B | 129690 | 0.52 | 30024 |
| A + B | 129691 | 0.52 | 30025 |
| A + B | 129694 | 0.51 | 30026 |
| A + B | 129695 | 0.51 | 30027 |
| A + B | 141923 | 0.53 | 30027 |
| A + B | 289606 | 0.47 | 30030 |
| A + B | 329586 | 0.50 | 30031 |
| A + B | 329804 | 0.55 | 30032 |
| A + B | 329492 | 0.54 | 18448 |
| A + B | 329493 | 0.57 | 18526 |
| A + B | 329494 | 0.53 | 18944 |
| A + B | 329495 | 0.53 | 19539 |
| A + B | 329496 | 0.40 | 19551 |
| A + B | 329497 | 0.46 | 20772 |
| A + B | 329498 | 0.45 | 21051 |
| A + B | 329499 | 0.47 | 21372 |
| A + B | 329500 | 0.49 | 22166 |
| A + B | 329501 | 0.45 | 23011 |
| A + B | 329502 | 0.49 | 23088 |
| A + B | 329503 | 0.42 | 23526 |
| A + B | 329504 | 0.49 | 23848 |
| A + B | 329505 | 0.48 | 24440 |
| A + B | 329506 | 0.53 | 24890 |
| A + B | 329507 | 0.47 | 25485 |
| A + B | 329508 | 0.52 | 25899 |
| A + B | 329509 | 0.50 | 25918 |
| A + B | 329510 | 0.51 | 26408 |
| A + B | 329511 | 0.49 | 26452 |
| A + B | 329512 | 0.46 | 26501 |
| A + B | 329513 | 0.45 | 26800 |
| A + B | 329514 | 0.54 | 27149 |
| A + B | 329515 | 0.45 | 27285 |
| A + B | 329516 | 0.51 | 27425 |
| A + B | 329517 | 0.52 | 27520 |
| A + B | 329518 | 0.50 | 27557 |
| A + B | 329519 | 0.41 | 27913 |
| A + B | 329410 | 0.47 | 13990 |
| A + B | 329411 | 0.45 | 13996 |
| A + B | 329412 | 0.51 | 15214 |
| A + B | 329413 | 0.56 | 15454 |
| A + B | 329414 | 0.47 | 15637 |
| A + B | 329415 | 0.46 | 15733 |

TABLE 14-continued

Effect of antisense inhibitors on SARS activity in Vero 76 cells: MTS assay

| Plates | Treatment (ISIS # or description) | Viral activity (O.D.) | SEQ ID NO |
|---|---|---|---|
| A + B | 329416 | 0.50 | 17098 |
| A + B | 329417 | 0.44 | 18562 |
| A + B | 329418 | 0.49 | 18789 |
| A + B | 329419 | 0.49 | 25072 |
| A + B | 329520 | 0.48 | 28180 |
| A + B | 329521 | 0.50 | 29128 |
| A + B | 329522 | 0.51 | 29487 |
| A + B | 329523 | 0.53 | 29523 |
| A + B | 329561 | 0.49 | 29971 |
| A + B | 329562 | 0.51 | 29972 |
| A + B | 329563 | 0.45 | 29973 |
| A + B | 329564 | 0.48 | 29974 |
| A + B | 329565 | 0.45 | 29975 |
| A + B | 329566 | 0.49 | 29976 |
| A + B | 329567 | 0.51 | 29977 |
| A + B | 329568 | 0.53 | 29978 |
| A + B | 329569 | 0.31 | 29979 |
| A + B | 329570 | 0.46 | 29980 |
| A + B | 329571 | 0.47 | 29981 |
| A + B | 329572 | 0.31 | 29982 |
| A + B | 329573 | 0.43 | 29983 |
| A + B | 329574 | 0.35 | 29984 |
| A + B | 329575 | 0.41 | 29985 |
| A + B | 329576 | 0.48 | 29986 |
| A + B | 329577 | 0.50 | 29987 |
| A + B | 329578 | 0.53 | 29988 |
| A + B | 329579 | 0.53 | 29989 |
| A + B | 329580 | 0.52 | 29990 |
| A + B | 329420 | 0.49 | 20 |
| A + B | 329421 | 0.56 | 21 |
| A + B | 329422 | 0.43 | 29831 |
| A + B | 329423 | 0.49 | 29832 |
| A + B | 329540 | 0.55 | 20 |
| A + B | 329541 | 0.56 | 21 |
| C + D | Media | 0.09 | N/A |
| C + D | Media + V | 0.09 | N/A |
| C + D | CC | 0.87 | N/A |
| C + D | VC | 0.46 | N/A |
| C + D | 129686 | 0.50 | 30020 |
| C + D | 129687 | 0.55 | 30021 |
| C + D | 129688 | 0.52 | 30022 |
| C + D | 129689 | 0.52 | 30023 |
| C + D | 129690 | 0.52 | 30024 |
| C + D | 129691 | 0.52 | 30025 |
| C + D | 129694 | 0.51 | 30026 |
| C + D | 129695 | 0.51 | 30027 |
| C + D | 141923 | 0.53 | 30027 |
| C + D | 289606 | 0.47 | 30030 |
| C + D | 329586 | 0.50 | 30031 |
| C + D | 329804 | 0.55 | 30032 |
| C + D | 329492 | 0.54 | 18448 |
| C + D | 329493 | 0.57 | 18526 |
| C + D | 329494 | 0.53 | 18944 |
| C + D | 329495 | 0.53 | 19539 |
| C + D | 329496 | 0.40 | 19551 |
| C + D | 329497 | 0.46 | 20772 |
| C + D | 329498 | 0.45 | 21051 |
| C + D | 329499 | 0.47 | 21372 |
| C + D | 329500 | 0.49 | 22166 |
| C + D | 329501 | 0.45 | 23011 |
| C + D | 329502 | 0.49 | 23088 |
| C + D | 329503 | 0.42 | 23526 |
| C + D | 329504 | 0.49 | 23848 |
| C + D | 329505 | 0.48 | 24440 |
| C + D | 329506 | 0.53 | 24890 |
| C + D | 329507 | 0.47 | 25485 |
| C + D | 329508 | 0.52 | 25899 |
| C + D | 329509 | 0.50 | 25918 |
| C + D | 329510 | 0.51 | 26408 |
| C + D | 329511 | 0.49 | 26452 |
| C + D | 329512 | 0.46 | 26501 |
| C + D | 329513 | 0.45 | 26800 |
| C + D | 329514 | 0.54 | 27149 |

TABLE 14-continued

Effect of antisense inhibitors on SARS activity in Vero 76 cells: MTS assay

| Plates | Treatment (ISIS # or description) | Viral activity (O.D.) | SEQ ID NO |
|---|---|---|---|
| C + D | 329515 | 0.45 | 27285 |
| C + D | 329516 | 0.51 | 27425 |
| C + D | 329517 | 0.52 | 27520 |
| C + D | 329518 | 0.50 | 27557 |
| C + D | 329519 | 0.41 | 27913 |
| C + D | 329410 | 0.47 | 13990 |
| C + D | 329411 | 0.45 | 13996 |
| C + D | 329412 | 0.51 | 15214 |
| C + D | 329413 | 0.56 | 15454 |
| C + D | 329414 | 0.47 | 15637 |
| C + D | 329415 | 0.46 | 15733 |
| C + D | 329416 | 0.50 | 17098 |
| C + D | 329417 | 0.44 | 18562 |
| C + D | 329418 | 0.49 | 18789 |
| C + D | 329419 | 0.49 | 25072 |
| C + D | 329520 | 0.48 | 28180 |
| C + D | 329521 | 0.50 | 29128 |
| C + D | 329522 | 0.51 | 29487 |
| C + D | 329523 | 0.53 | 29523 |
| C + D | 329561 | 0.49 | 29971 |
| C + D | 329562 | 0.51 | 29972 |
| C + D | 329563 | 0.45 | 29973 |
| C + D | 329564 | 0.48 | 29974 |
| C + D | 329565 | 0.45 | 29975 |
| C + D | 329566 | 0.49 | 29976 |
| C + D | 329567 | 0.51 | 29977 |
| C + D | 329568 | 0.53 | 29978 |
| C + D | 329569 | 0.31 | 29979 |
| C + D | 329570 | 0.46 | 29980 |
| C + D | 329571 | 0.47 | 29981 |
| C + D | 329572 | 0.31 | 29982 |
| C + D | 329573 | 0.43 | 29983 |
| C + D | 329574 | 0.35 | 29984 |
| C + D | 329575 | 0.41 | 29985 |
| C + D | 329576 | 0.48 | 29986 |
| C + D | 329577 | 0.50 | 29987 |
| C + D | 329578 | 0.53 | 29988 |
| C + D | 329579 | 0.53 | 29989 |
| C + D | 329580 | 0.52 | 29990 |
| C + D | 329420 | 0.49 | 20 |
| C + D | 329421 | 0.56 | 21 |
| C + D | 329422 | 0.43 | 29831 |
| C + D | 329423 | 0.49 | 29832 |
| C + D | 329540 | 0.55 | 20 |
| C + D | 329541 | 0.56 | 21 |
| E + F | Media | 0.09 | N/A |
| E + F | Media + V | 0.09 | N/A |
| E + F | CC | 0.80 | N/A |
| E + F | VC | 0.44 | N/A |
| E + F | 129686 | 0.46 | 30020 |
| E + F | 129687 | 0.44 | 30021 |
| E + F | 129688 | 0.50 | 30022 |
| E + F | 129689 | 0.46 | 30023 |
| E + F | 129690 | 0.47 | 30024 |
| E + F | 129691 | 0.45 | 30025 |
| E + F | 129694 | 0.48 | 30026 |
| E + F | 129695 | 0.48 | 30027 |
| E + F | 141923 | 0.52 | 30027 |
| E + F | 289606 | 0.49 | 30030 |
| E + F | 329586 | 0.45 | 30031 |
| E + F | 329804 | 0.47 | 30032 |
| E + F | 329542 | 0.45 | 29831 |
| E + F | 329543 | 0.49 | 29832 |
| E + F | 329544 | 0.48 | 29833 |
| E + F | 329581 | 0.41 | 30000 |
| E + F | 329582 | 0.43 | 30001 |
| E + F | 329583 | 0.49 | 30002 |
| E + F | 329584 | 0.47 | 30003 |
| E + F | 329585 | 0.52 | 30004 |
| E + F | 329524 | 0.52 | 13396 |
| E + F | 329525 | 0.54 | 13404 |
| E + F | 329526 | 0.49 | 13411 |
| E + F | 329527 | 0.44 | 13415 |
| E + F | 329528 | 0.51 | 13445 |
| E + F | 329529 | 0.43 | 13464 |
| E + F | 329530 | 0.50 | 13471 |
| E + F | 329545 | 0.40 | 29833 |
| E + F | 329546 | 0.47 | 13396 |
| E + F | 329547 | 0.57 | 13404 |
| E + F | 329548 | 0.47 | 13411 |
| E + F | 329549 | 0.53 | 13415 |
| E + F | 329550 | 0.57 | 13445 |
| E + F | 329551 | 0.53 | 13464 |
| E + F | 329552 | 0.54 | 13471 |
| E + F | 329553 | 0.57 | 64 |
| E + F | 329554 | 0.51 | 21483 |
| E + F | 329555 | 0.51 | 25257 |
| E + F | 329556 | 0.50 | 26106 |
| E + F | 329557 | 0.47 | 26345 |
| E + F | 329558 | 0.54 | 26910 |
| E + F | 329559 | 0.55 | 27264 |
| E + F | 329560 | 0.50 | 27770 |
| E + F | 330490 | 0.53 | 30005 |
| E + F | 330491 | 0.48 | 30006 |
| E + F | 330492 | 0.48 | 30007 |
| E + F | 330493 | 0.50 | 30008 |
| E + F | 330494 | 0.49 | 30009 |
| E + F | 330495 | 0.47 | 30010 |
| E + F | 330496 | 0.51 | 30011 |
| E + F | 330497 | 0.41 | 30012 |
| E + F | 330498 | 0.44 | 30013 |
| E + F | 329531 | 0.50 | 64 |
| E + F | 329532 | 0.54 | 21483 |
| E + F | 329533 | 0.48 | 25257 |
| E + F | 329534 | 0.54 | 26106 |
| E + F | 329535 | 0.51 | 26345 |
| E + F | 329536 | 0.52 | 26910 |
| E + F | 329537 | 0.52 | 27264 |
| E + F | 329538 | 0.55 | 27770 |
| E + F | 329539 | 0.49 | 28103 |
| E + F | 330481 | 0.46 | 28103 |
| E + F | 330482 | 0.41 | 29992 |
| E + F | 330483 | 0.46 | 29993 |
| E + F | 330484 | 0.54 | 29994 |
| E + F | 330485 | 0.51 | 29995 |
| E + F | 330486 | 0.49 | 29996 |
| E + F | 330487 | 0.51 | 29997 |
| E + F | 330488 | 0.48 | 29998 |
| E + F | 330489 | 0.52 | 29999 |
| E + F | 333040 | 0.56 | 30049 |
| E + F | 333048 | 0.55 | 30050 |
| E + F | 333049 | 0.51 | 30051 |
| E + F | 333054 | 0.48 | 30052 |
| E + F | 333057 | 0.41 | 30053 |
| E + F | 330538 | 0.45 | 30048 |
| E + F | 329591 | 0.49 | 29934 |
| E + F | 329729 | 0.38 | 13464 |
| E + F | 334962 | 0.41 | 29874 |
| E + F | 334963 | 0.46 | 298975 |
| G + H | Media | 0.09 | N/A |
| G + H | Media + V | 0.09 | N/A |
| G + H | CC | 0.87 | N/A |
| G + H | VC | 0.38 | N/A |
| G + H | 129686 | 0.44 | 30020 |
| G + H | 129687 | 0.49 | 30021 |
| G + H | 129688 | 0.43 | 30022 |
| G + H | 129689 | 0.55 | 30023 |
| G + H | 129690 | 0.56 | 30024 |
| G + H | 129691 | 0.50 | 30025 |
| G + H | 129694 | 0.54 | 30026 |
| G + H | 129695 | 0.54 | 30027 |
| G + H | 141923 | 0.52 | 30027 |
| G + H | 289606 | 0.50 | 30030 |
| G + H | 329586 | 0.36 | 30031 |
| G + H | 329804 | 0.50 | 30032 |
| G + H | 334996 | 0.48 | 30034 |

TABLE 14-continued

Effect of antisense inhibitors on SARS activity in Vero 76 cells: MTS assay

| Plates | Treatment (ISIS # or description) | Viral activity (O.D.) | SEQ ID NO |
|---|---|---|---|
| G + H | 334998 | 0.51 | 29910 |
| G + H | 335001 | 0.51 | 29913 |
| G + H | 335003 | 0.51 | 29914 |
| G + H | 335005 | 0.47 | 29917 |

Example 25

Antisense Oligonucleotide Inhibition of SARS Activity in Vero 76 Cells: Neutral Red (NR) Assay Antisense oligonucleotides targeting the SARS-CoV gene were transfected as in example 23, using 3 μL Lipofectin/ 100 nM oligonucleotide/1 mL Opti-MEM. Cells were exposed to CoV at an MOI of 0.3 for 1 hour, and washed with assay medium which was replaced.

Viability was tested using NR after cells had recovered for 72 hours post-infection. As cells lose viability, they lose the ability to take up NR. Each plate contained 12 negative control oligonucleotides indicated in bold in the table. Data are presented as the average of two O.D. measurements per antisense oligonucleotide tested. The replicate plates averaged for each data point are indicated in Table 15 "Plates." Each plate contained 4 of each of the following control wells: media alone with no cells (Media), media and virus with no cells (Media+Virus), cells alone with no virus or oligonucleotide treatment (Cell Control), and cells and virus with no oligonucleotide treatment (Virus Control). The O.D. presented for each of these controls is thus the average of eight measurements for each set of duplicate plates. Because the O.D. measured is proportional to the number of living cells in culture, the O.D. is indicative of "viral activity", wherein an O.D. reading close to that for the Cell Control suggests inhibition of virus activity by the treatment, and an O.D. reading close to that for the Virus Control suggest no affect on virus activity.

TABLE 15

Effect of antisense inhibitors on SARS activity in Vero 76 cells: NR assay

| Plates | Treatment (ISIS # or description) | Viral Activity (O.D.) | SEQ ID NO |
|---|---|---|---|
| 1 + 2 | Media | 0.97 | N/A |
| 1 + 2 | Media + Virus | 0.64 | N/A |
| 1 + 2 | Cell Control | 0.83 | N/A |
| 1 + 2 | Virus Control | 1.15 | N/A |
| 1 + 2 | 129686 | 0.40 | 30020 |
| 1 + 2 | 129687 | 0.47 | 30021 |
| 1 + 2 | 129688 | 0.47 | 30022 |
| 1 + 2 | 129689 | 0.60 | 30023 |
| 1 + 2 | 129690 | 0.69 | 30024 |
| 1 + 2 | 129691 | 0.36 | 30025 |
| 1 + 2 | 129694 | 0.71 | 30026 |
| 1 + 2 | 129695 | 0.52 | 30027 |
| 1 + 2 | 141923 | 1.39 | 30027 |
| 1 + 2 | 289606 | 0.44 | 30030 |
| 1 + 2 | 329586 | 1.20 | 30031 |
| 1 + 2 | 329804 | 1.00 | 30032 |
| 1 + 2 | 329424 | 0.39 | 211 |
| 1 + 2 | 329425 | 0.29 | 221 |
| 1 + 2 | 329426 | 0.47 | 372 |
| 1 + 2 | 329427 | 0.56 | 390 |
| 1 + 2 | 329428 | 0.36 | 1335 |
| 1 + 2 | 329429 | 0.61 | 1772 |
| 1 + 2 | 329430 | 1.01 | 1774 |
| 1 + 2 | 329431 | 0.68 | 1869 |
| 1 + 2 | 329432 | 0.52 | 2094 |
| 1 + 2 | 329433 | 0.80 | 2403 |
| 1 + 2 | 329434 | 0.40 | 2753 |
| 1 + 2 | 329435 | 0.76 | 2830 |
| 1 + 2 | 329436 | 1.10 | 3150 |
| 1 + 2 | 329437 | 0.36 | 3308 |
| 1 + 2 | 329438 | 0.67 | 4025 |
| 1 + 2 | 329439 | 0.75 | 4271 |
| 1 + 2 | 329440 | 1.00 | 4842 |
| 1 + 2 | 329441 | 0.56 | 5294 |
| 1 + 2 | 329442 | 0.78 | 5348 |
| 1 + 2 | 329443 | 0.64 | 5486 |
| 1 + 2 | 329444 | 0.37 | 5643 |
| 1 + 2 | 329445 | 0.85 | 5653 |
| 1 + 2 | 329446 | 0.54 | 6014 |
| 1 + 2 | 329447 | 0.31 | 6481 |
| 1 + 2 | 329448 | 0.81 | 6619 |
| 1 + 2 | 329449 | 0.87 | 6994 |
| 1 + 2 | 329450 | 0.55 | 7028 |
| 1 + 2 | 329451 | 0.70 | 7165 |
| 1 + 2 | 329452 | 0.53 | 7541 |
| 1 + 2 | 329453 | 1.10 | 7971 |
| 1 + 2 | 329454 | 0.57 | 8025 |
| 1 + 2 | 329455 | 0.55 | 8589 |
| 1 + 2 | 329456 | 0.77 | 8597 |
| 1 + 2 | 329457 | 0.60 | 9110 |
| 1 + 2 | 329458 | 0.86 | 9151 |
| 1 + 2 | 329459 | 1.10 | 9384 |
| 1 + 2 | 329460 | 0.57 | 9894 |
| 1 + 2 | 329461 | 1.07 | 9937 |
| 1 + 2 | 329462 | 0.50 | 10008 |
| 1 + 2 | 329463 | 1.16 | 10465 |
| 1 + 2 | 329464 | 0.92 | 10796 |
| 1 + 2 | 329465 | 0.85 | 11206 |
| 1 + 2 | 329466 | 0.72 | 11513 |
| 1 + 2 | 329467 | 0.61 | 11982 |
| 1 + 2 | 329468 | 0.81 | 12007 |
| 1 + 2 | 329469 | 0.63 | 12273 |
| 1 + 2 | 329470 | 0.85 | 12454 |
| 1 + 2 | 329471 | 1.08 | 13178 |
| 1 + 2 | 329472 | 1.11 | 13195 |
| 1 + 2 | 329473 | 0.84 | 13242 |
| 1 + 2 | 329591 | 0.43 | 29934 |
| 1 + 2 | 329729 | 0.40 | 13464 |
| 3 + 4 | Media | 0.64 | N/A |
| 3 + 4 | Media + Virus | 0.67 | N/A |
| 3 + 4 | Cell Control | 1.36 | N/A |
| 3 + 4 | Virus Control | 0.47 | N/A |
| 3 + 4 | 129686 | 0.91 | 30020 |
| 3 + 4 | 129687 | 0.47 | 30021 |
| 3 + 4 | 129688 | 0.61 | 30022 |
| 3 + 4 | 129689 | 0.37 | 30023 |
| 3 + 4 | 129690 | 0.38 | 30024 |
| 3 + 4 | 129691 | 0.39 | 30025 |
| 3 + 4 | 129694 | 0.66 | 30026 |
| 3 + 4 | 129695 | 0.24 | 30027 |
| 3 + 4 | 141923 | 0.50 | 30027 |
| 3 + 4 | 289606 | 0.57 | 30030 |
| 3 + 4 | 329586 | 0.47 | 30031 |
| 3 + 4 | 329804 | 0.51 | 30032 |
| 3 + 4 | 329410 | 0.39 | 13990 |
| 3 + 4 | 329411 | 0.41 | 13996 |
| 3 + 4 | 329412 | 0.28 | 15214 |
| 3 + 4 | 329413 | 0.39 | 15454 |
| 3 + 4 | 329474 | 0.37 | 13627 |
| 3 + 4 | 329475 | 0.83 | 13997 |
| 3 + 4 | 329476 | 0.49 | 14058 |
| 3 + 4 | 329477 | 0.38 | 14258 |

TABLE 15-continued

Effect of antisense inhibitors on SARS activity in Vero 76 cells: NR assay

| Plates | Treatment (ISIS # or description) | Viral Activity (O.D.) | SEQ ID NO |
|---|---|---|---|
| 3 + 4 | 329478 | 0.88 | 14724 |
| 3 + 4 | 329479 | 0.56 | 14847 |
| 3 + 4 | 329480 | 0.98 | 14995 |
| 3 + 4 | 329481 | 0.65 | 15084 |
| 3 + 4 | 329482 | 0.34 | 15420 |
| 3 + 4 | 329483 | 0.36 | 15744 |
| 3 + 4 | 329484 | 0.38 | 15836 |
| 3 + 4 | 329485 | 0.35 | 15904 |
| 3 + 4 | 329486 | 0.38 | 16653 |
| 3 + 4 | 329487 | 0.44 | 16888 |
| 3 + 4 | 329488 | 0.29 | 17328 |
| 3 + 4 | 329489 | 0.40 | 17738 |
| 3 + 4 | 329490 | 0.62 | 17768 |
| 3 + 4 | 329491 | 0.35 | 18420 |
| 3 + 4 | 329492 | 0.39 | 18448 |
| 3 + 4 | 329493 | 0.32 | 18526 |
| 3 + 4 | 329494 | 0.34 | 18944 |
| 3 + 4 | 329495 | 0.36 | 19539 |
| 3 + 4 | 329496 | 0.28 | 19551 |
| 3 + 4 | 329497 | 0.27 | 20772 |
| 3 + 4 | 329498 | 0.47 | 21051 |
| 3 + 4 | 329499 | 0.44 | 21372 |
| 3 + 4 | 329500 | 0.64 | 22166 |
| 3 + 4 | 329501 | 0.33 | 23011 |
| 3 + 4 | 329502 | 0.46 | 23088 |
| 3 + 4 | 329503 | 0.50 | 23526 |
| 3 + 4 | 329504 | 0.37 | 23848 |
| 3 + 4 | 329505 | 0.25 | 24440 |
| 3 + 4 | 329506 | 1.07 | 24890 |
| 3 + 4 | 329507 | 0.62 | 25485 |
| 3 + 4 | 329508 | 0.47 | 25899 |
| 3 + 4 | 329509 | 0.38 | 25918 |
| 3 + 4 | 329510 | 0.47 | 26408 |
| 3 + 4 | 329511 | 0.40 | 26452 |
| 3 + 4 | 329512 | 0.94 | 26501 |
| 3 + 4 | 329513 | 0.32 | 26800 |
| 3 + 4 | 329514 | 0.41 | 27149 |
| 3 + 4 | 329515 | 0.53 | 27285 |
| 3 + 4 | 329516 | 0.49 | 27425 |
| 3 + 4 | 329517 | 0.44 | 27520 |
| 3 + 4 | 329518 | 0.54 | 27557 |
| 3 + 4 | 329519 | 0.44 | 27913 |
| 3 + 4 | 334962 | 0.53 | 29874 |
| 3 + 4 | 334963 | 0.32 | 29875 |
| 5 + 6 | Media | 0.75 | N/A |
| 5 + 6 | Media + Virus | 0.81 | N/A |
| 5 + 6 | Cell Control | 1.24 | N/A |
| 5 + 6 | Virus Control | 0.50 | N/A |
| 5 + 6 | 129686 | 0.44 | 30020 |
| 5 + 6 | 129687 | 0.47 | 30021 |
| 5 + 6 | 129688 | 0.37 | 30022 |
| 5 + 6 | 129689 | 0.39 | 30023 |
| 5 + 6 | 129690 | 0.39 | 30024 |
| 5 + 6 | 129691 | 0.70 | 30025 |
| 5 + 6 | 129694 | 0.43 | 30026 |
| 5 + 6 | 129695 | 0.43 | 30027 |
| 5 + 6 | 141923 | 0.38 | 30027 |
| 5 + 6 | 289606 | 0.47 | 30030 |
| 5 + 6 | 329586 | 0.52 | 30031 |
| 5 + 6 | 329804 | 0.41 | 30032 |
| 5 + 6 | 329414 | 0.40 | 15637 |
| 5 + 6 | 329415 | 0.43 | 15733 |
| 5 + 6 | 329416 | 0.42 | 17098 |
| 5 + 6 | 329417 | 0.29 | 18562 |
| 5 + 6 | 329418 | 0.35 | 18789 |
| 5 + 6 | 329419 | 0.32 | 25072 |
| 5 + 6 | 329420 | 0.26 | 20 |
| 5 + 6 | 329421 | 0.80 | 21 |
| 5 + 6 | 329422 | 0.38 | 29831 |
| 5 + 6 | 329423 | 0.35 | 29832 |
| 5 + 6 | 329520 | 0.38 | 28180 |
| 5 + 6 | 329521 | 0.32 | 29128 |
| 5 + 6 | 329522 | 0.36 | 29487 |
| 5 + 6 | 329523 | 0.51 | 29523 |
| 5 + 6 | 329524 | 0.30 | 13396 |
| 5 + 6 | 329525 | 0.29 | 13404 |
| 5 + 6 | 329526 | 0.39 | 13411 |
| 5 + 6 | 329527 | 0.52 | 13415 |
| 5 + 6 | 329528 | 0.49 | 13445 |
| 5 + 6 | 329529 | 0.43 | 13464 |
| 5 + 6 | 329540 | 0.61 | 20 |
| 5 + 6 | 329541 | 0.60 | 21 |
| 5 + 6 | 329542 | 0.31 | 29831 |
| 5 + 6 | 329543 | 0.40 | 29832 |
| 5 + 6 | 329544 | 0.30 | 28104 |
| 5 + 6 | 329561 | 0.43 | 29971 |
| 5 + 6 | 329562 | 0.28 | 29972 |
| 5 + 6 | 329563 | 0.40 | 29973 |
| 5 + 6 | 329564 | 0.27 | 29974 |
| 5 + 6 | 329565 | 0.30 | 29975 |
| 5 + 6 | 329566 | 0.46 | 29976 |
| 5 + 6 | 329567 | 0.33 | 29977 |
| 5 + 6 | 329568 | 0.43 | 29978 |
| 5 + 6 | 329569 | 0.39 | 29979 |
| 5 + 6 | 329570 | 0.30 | 29980 |
| 5 + 6 | 329571 | 0.39 | 29981 |
| 5 + 6 | 329572 | 0.29 | 29982 |
| 5 + 6 | 329573 | 0.35 | 29983 |
| 5 + 6 | 329574 | 0.35 | 29984 |
| 5 + 6 | 329575 | 0.38 | 29985 |
| 5 + 6 | 329576 | 0.34 | 29986 |
| 5 + 6 | 329577 | 0.34 | 29987 |
| 5 + 6 | 329578 | 0.28 | 29988 |
| 5 + 6 | 329579 | 0.26 | 29989 |
| 5 + 6 | 329580 | 0.56 | 29990 |
| 5 + 6 | 329581 | 0.33 | 30000 |
| 5 + 6 | 329582 | 0.25 | 30001 |
| 5 + 6 | 329583 | 0.31 | 30002 |
| 5 + 6 | 329584 | 0.40 | 30003 |
| 5 + 6 | 329585 | 0.31 | 30004 |
| 5 + 6 | 334996 | 0.42 | 29908 |
| 5 + 6 | 334998 | 0.36 | 29910 |
| 7 + 8 | Media | 0.99 | N/A |
| 7 + 8 | Media + Virus | 0.70 | N/A |
| 7 + 8 | Cell Control | 1.21 | N/A |
| 7 + 8 | Virus Control | 0.58 | N/A |
| 7 + 8 | 129686 | 0.57 | 30020 |
| 7 + 8 | 129687 | 0.47 | 30021 |
| 7 + 8 | 129688 | 0.44 | 30022 |
| 7 + 8 | 129689 | 0.39 | 30023 |
| 7 + 8 | 129690 | 0.74 | 30024 |
| 7 + 8 | 129691 | 1.04 | 30025 |
| 7 + 8 | 129694 | 0.46 | 30026 |
| 7 + 8 | 129695 | 0.41 | 30027 |
| 7 + 8 | 141923 | 0.31 | 30027 |
| 7 + 8 | 289606 | 0.87 | 30030 |
| 7 + 8 | 329586 | 0.55 | 30031 |
| 7 + 8 | 329804 | 0.52 | 30032 |
| 7 + 8 | 329530 | 0.83 | 13471 |
| 7 + 8 | 329531 | 0.26 | 64 |
| 7 + 8 | 329532 | 0.22 | 21483 |
| 7 + 8 | 329533 | 0.24 | 25257 |
| 7 + 8 | 329534 | 0.21 | 26106 |
| 7 + 8 | 329535 | 0.27 | 26345 |
| 7 + 8 | 329536 | 0.19 | 26910 |
| 7 + 8 | 329537 | 0.29 | 27264 |
| 7 + 8 | 329538 | 0.26 | 27770 |
| 7 + 8 | 329539 | 0.46 | 28103 |
| 7 + 8 | 329545 | 1.03 | 29833 |
| 7 + 8 | 329546 | 0.60 | 13396 |
| 7 + 8 | 329547 | 0.98 | 13404 |
| 7 + 8 | 329548 | 1.00 | 13411 |
| 7 + 8 | 329549 | 0.45 | 13415 |
| 7 + 8 | 329550 | 0.53 | 13445 |
| 7 + 8 | 329551 | 0.68 | 13464 |
| 7 + 8 | 329552 | 0.40 | 13471 |

TABLE 15-continued

Effect of antisense inhibitors on SARS activity in Vero 76 cells: NR assay

| Plates | Treatment (ISIS # or description) | Viral Activity (O.D.) | SEQ ID NO |
|---|---|---|---|
| 7 + 8 | 329553 | 0.29 | 64 |
| 7 + 8 | 329554 | 0.27 | 21483 |
| 7 + 8 | 329555 | 0.31 | 25257 |
| 7 + 8 | 329556 | 0.42 | 26106 |
| 7 + 8 | 329557 | 0.22 | 26345 |
| 7 + 8 | 329558 | 0.38 | 26910 |
| 7 + 8 | 329559 | 0.30 | 27264 |
| 7 + 8 | 329560 | 0.32 | 27770 |
| 7 + 8 | 330481 | 0.27 | 29991 |
| 7 + 8 | 330482 | 0.33 | 29992 |
| 7 + 8 | 330483 | 0.40 | 29993 |
| 7 + 8 | 330484 | 0.37 | 29994 |
| 7 + 8 | 330485 | 0.35 | 29995 |
| 7 + 8 | 330486 | 0.17 | 29996 |
| 7 + 8 | 330487 | 0.27 | 29997 |
| 7 + 8 | 330488 | 0.27 | 29998 |
| 7 + 8 | 330489 | 0.25 | 29999 |
| 7 + 8 | 330490 | 0.32 | 30005 |
| 7 + 8 | 330491 | 0.36 | 30006 |
| 7 + 8 | 330492 | 0.30 | 30007 |
| 7 + 8 | 330493 | 0.31 | 30008 |
| 7 + 8 | 330494 | 0.23 | 30009 |
| 7 + 8 | 330495 | 0.20 | 30010 |
| 7 + 8 | 330496 | 0.58 | 30011 |
| 7 + 8 | 330497 | 0.40 | 30012 |
| 7 + 8 | 330498 | 0.31 | 30013 |
| 7 + 8 | 330538 | 0.26 | 30048 |
| 7 + 8 | 333040 | 0.39 | 30049 |
| 7 + 8 | 333048 | 0.47 | 30050 |
| 7 + 8 | 333049 | 0.29 | 30051 |
| 7 + 8 | 333054 | 0.34 | 30052 |
| 7 + 8 | 333057 | 0.26 | 30053 |
| 7 + 8 | 334996 | 0.42 | 29908 |
| 7 + 8 | 334998 | 0.36 | 29910 |
| 7 + 8 | 335001 | 0.33 | 29913 |
| 7 + 8 | 335003 | 0.37 | 29915 |
| 7 + 8 | 335005 | 0.32 | 29917 |

Based on the O.D. as compared to that for cell control and virus control for replicate plates 3 and 4, ISIS 329475, ISIS 329478, ISIS 329480, ISIS 329506, and ISIS 329512 were identified as potential inhibitors of viral activity. For replicate plates 5 and 6, ISIS 329421, ISIS 329540, and ISIS 329541 were identified as potential inhibitors of viral activity. For replicate plates 7 and 8, ISIS 329530, ISIS 329545, ISIS 329547, and ISIS 329548 were identified as potential inhibitors of viral activity.

Example 26

Antisense Oligonucleotide Inhibition of SARS Activity in Vero 76 Cells: NR Assay Antisense oligonucleotides targeted to SARS were tested for inhibition of SARS activity in an additional assay. Vero cells were transfected with the oligonucleotides as described in Example 22 prior to exposure with the SARS coronavirus Urbani strain 200300592 at a multiplicity of infection of 0.001. A pair of non-infected wells served as controls. The plates were scored visually at 4 days post virus exposure for cytopathic effect (CPE). Medium was removed from each well of a plate that had been scored for CPE, and 0.034% NR was added to each well. After a 2 hour incubation at 37° C. in the dark, the NR solution was removed from the wells, rinsed, and the remaining dye was extracted using ethanol buffered with Sorenson's citrate buffer. Dye uptake was read at absorbances of 540 nm and 450 nm with a microplate reader (Bio-Tek EL 1309; Bio-Tek Instruments, Inc., Winooski, Vt.).

The absorbance value indicates the amount of NR taken up by the cells. As cells lose viability, they lose the ability to take up NR. Compounds that had absorbance values within 40% of the uninfected control cells were considered potential inhibitors of SARS-CoV.

Of the compounds tested, 17 oligonucleotides were identified as potential inhibitors of SARS-CoV: ISIS 329437, ISIS 329474, ISIS 329475, ISIS 329481, ISIS 329483, ISIS 329487, ISIS 329488, ISIS 329497, ISIS 329504, ISIS 329505, ISIS 329513, ISIS 329521, ISIS 329540, ISIS 329541, ISIS 329547, ISIS 329550, and ISIS 329551.

Example 27

Characterization of a Frameshift Site in the RNA of the SARS Coronavirus

In accordance with the present invention, a comparative sequence analysis (CSA) method was developed to locate the essential "signature" structures of the RNA that are conserved across species, for drug design and screening. The CSA approach is based on the paradigm that RNAs tend to conserve functionally relevant structures during evolution, and by comparing sequences across different organisms, one can identify the secondary structures that are preserved in spite of alterations in individual bases. RNAs have conserved secondary structures with base-pairing interactions which are more conserved than primary sequences. This is due to the introduction of compensatory mutations to maintain base-pair complementarity. These compensatory mutations can be identified in an iterative process of comparing sequences using a technique called covariance analysis performed on multiple sequence alignments. Most of the well-known RNA structures have been discovered using this method (R. R. Gutell, Curr. Opin. Struct. Biol. 3, 313-322 (1993); R. Durbin, S. Eddy, A. Krogh, G. Mitchison, Biological Sequence Analysis: Probabilistic Models of Proteins and Nucleic Acids (Cambridge University Press, Cambridge, 1998), and the results have been verified by physical methods like crystallography and NMR.

In order to identify phylogenetically conserved RNA targets in the SARS coronavirus and other coronaviruses, whole genome sequences of coronavirus sequences in GenBank were analyzed. These sequences represent examples of all major groups of this family and include: Transmissible gastroenteritis virus (GenBank accession number NC_002306, incorporated herein as SEQ ID NO:30055); Human coronavirus 229E (GenBank accession number NC_002645, incorporated herein as SEQ ID NO:30056); Porcine epidemic diarrhea virus (GenBank accession number NC_003436, incorporated herein as SEQ ID NO:30057); Avian infectious bronchitis virus (GenBank accession number NC_001451, incorporated herein as SEQ ID NO:30058); SARS coronavirus (GenBank accession number NC_004718, incorporated herein as SEQ ID NO:29752); Murine hepatitis virus (GenBank accession number NC_001846, incorporated herein as SEQ ID NO:30059) and Bovine coronavirus (GenBank accession number NC_003045, incorporated herein as SEQ ID NO:30060). These sequences are shown to contain thymine (T) but one of ordinary skill in the art will appreciate that thymine (T) is generally replaced by uracil (U) in RNA sequences.

By the iterative process described above, structure-based alignments spanning all of these viruses were generated. One of the well-characterized structures in the coronavirus genome is its pseudoknot-containing frameshift site which is essential for the life cycle of the virus. The results of sequence analysis indicated that the SARS virus has a significant degree of sequence homology with the other coronaviruses that have documented frameshift sites (Figure $). From the sequence comparison it was determined that the component regions of the slippery site and pseudoknot are generally conserved in the alignment. This analysis has verified that the SARS coronavirus contains a pseudoknot motif and frameshift site common to other coronaviruses, which appears to control the expression of the essential RNA-dependent RNA polymerase (RdRp) gene in a similar manner. These characteristics make the SARS coronavirus 1a/1b frameshift site a useful target for drug discovery.

One with ordinary skill in the art will recognize that characterization of a frameshift site of a virus further enables characterization of sub-segments of the frameshift site which include the slippery site and the pseudoknot. One with ordinary skill in the art will also recognize that characterization of a pseudoknot also enables one to characterize the loops and stems within the pseudoknot.

Example 28

Construction of the Plasmid pSARS and in vitro Transcription of SARS RNA Including the Frameshift Site In accordance with the present invention, a 79-bp SARS coronavirus DNA construct which includes the frameshift site was constructed by annealing long DNA oligonucleotides (overlapping by 15 base pairs) with subsequent extension by Pfu DNA polymerase to form double-stranded DNA. This fragment was then re-amplified in a PCR reaction with a forward primer that introduced an EcoRi restriction site and T7 RNA polymerase recognized sequences at its 5' end, and a reverse primer that introduced a HindIII restriction site at its 3' end. After restriction digestion, the PCR product was cloned into a pUC19 vector which had been previously digested with HindII and EcoRI. The resulting plasmid designated herein as "pSARS" was sequenced to confirm that the desired SARS RNA could be transcribed from the T7 promoter. The plasmid was linearized with HindIII and the T7 MEGAShort™ in vitro transcription assay kit was used to generate a large quantity of RNA according to the manufacturer's procedures. An 85-nt RNA with GG and AGCU flanking the SARS sequence due to the T7 transcription start and the 5' overhang of the HindII cut on the template strain, showed as a major band (>95% purity) on a 6% denaturing polyacrylamide gel. This RNA band was recovered from the gel and eluted overnight in 2 mM ammonium acetate with incubation at 4° C. The RNA was precipitated with 10 mM ammonium acetate.

Example 29

Construction of Reporting Plasmids pSARS1, pSARS2 and pSARS3

For determination of modulation of frameshifting efficiency (see Example 30) three different frameshift reporting plasmids are required, all of which contain the frameshifting site of the SARS coronavirus fused to the firefly luciferase reporter gene such that the reporter gene is translated only if the 1b reading frame is translated. Thus, if a frameshift from 1a to 1b does not occur, the reporter gene is not translated. The three frameshift reporting plasmids are herein designated pSARS1, pSARS2 and pSARS3. pSARS1 (SEQ ID NO:30061) functions as a positive control, pSARS2 (SEQ ID NO:30062) represents the natural SARS coronavirus frameshifting site and pSARS3 (SEQ ID NO:30063) is employed as a negative control.

Relative to the natural SARS coronavirus frameshifting site of pSARS2, pSARS1 has a replacement of the sequence TTTTT (beginning 2 nucleotides to the 5' end of the slippery site) with CTGCTG. This modification results in an RNA whose slippery site is abolished and which is completely translated in the 1b reading frame from the 5' end of the nucleotide replacements. Thus, a constant "simulated frameshift" occurs and 100% of translated protein contains the luciferase reporter gene.

Relative to the natural SARS coronavirus frameshifting site of pSARS2, the negative control pSARS3 has a replacement of the sequence TTTTTA (beginning 2 nucleotides to the 5' end of the slippery site) with CTG. This modification results in an RNA whose slippery site is abolished and which is completely translated in the 1b reading frame from the 5' end of the nucleotide replacement site. However, in contrast to pSARS1, the replacement of TTTTTA with CTG introduces a stop codon 15 nucleotides downstream from the replacement site. This stop codon prevents the luciferase reporter gene from being translated and thus, the plasmid pSARS3 functions as a negative control.

Using the 79-bp PCR product from the previous construction of pSARS as template, two consecutive PCR reactions were carried out to extend the expected DNA fragment 21-bp beyond the 5' of the slippery site and simultaneously introduce restriction cut sites at both ends of the product for cloning. The first round of PCR yielded an intermediate product that had a BamHI site added to the immediate downstream of the SARS 1a/1b pseudoknot but just upstream of a start codon ATG. The ATG on the reverse primer was designed to be in-frame with the SARS 1b gene. From the first amino acid resulting from the frameshift to the methionine encoded by the ATG, there is a 90-bp sequence encoding 30 amino acids that are part of the 1b translation product. The second round of PCR used the product of first round PCR as template. The forward primers bear different sequences for different constructs. In addition, a NheI restriction site was designed at the 5' end of these forward primers. SARS1_F_NheI was used to generate the DNA fragment for the positive control plasmid pSARS1. SARS2_F_NheI was for the plasmid pSARS2 containing natural slippage sequence and SARS3_F_NheI was for the negative control plasmid pSARS3. Separately, a firefly luciferase gene (F-luc, Promega, Madison, Wis.) was cloned into a commercial vector pcDNA5.1 (Invitrogen, Carlsbad, Calif.) under the control of a T7 promoter. This created plasmid, herein designated pFluc has a NheI site at about 20 nucleotides downstream of the T7 transcription start and a BamHI site immediately upstream of the ATG start codon of the F-luc. The PCR products were digested with NheI and BamHI and cloned into pFluc to generate pSARS1, pSARS2 and pSARS3.

Example 30

In vitro Assay of Frameshifting Efficiency of Model RNA of the SARS Coronavirus Reporting plasmids (pSARS1, pSARS2 and pSARS3) representing model RNA constructs were linearized with EcoRI and in vitro transcribed to produce a ~2.1 k-nt capped mRNA with a MESSENGER machine kit (Ambion, Austin, Tex). Between the constructs, expression of an active firefly luciferase encoded by the mRNA is solely dependent on the ribosomal slippage mechanism. The mRNAs were purified with a MEGAclear™ kit (Ambion, Austin, Tex) and the concentration was determined from a UV reading. 2 µl RNA and 2 µl H$_2$O (or compounds) were mixed in a well of a 96 well plate for scintillation counting, 16 µl rabbit reticulocyte lysate was added into the well and incubated for one and half hour at 30° C. 20 µl luciferase substrate (Promega, Madison, Wis.) was added into the reaction and mixed for 1 minute. The light emission (LE) was measured on a Topcounter (Canberra-Packard Company, Meriden, Conn., USA).

Determination of frameshift efficiency (FSE) is performed as follows:

FSE=(LE of pSARS2−LE of pSARS3)/(LE of pSARS1−LE of pSARS3)×100%

The frameshift efficiency of the frameshifting site of the natural SARS coronavirus was thus found to be 40±4%.

Example 31

Modulation of Frameshifting Efficiency of the Model RNA of the SARS Coronavirus by 2′-O-Methoxyethyl Oligonucleotides In accordance with the present invention, a series of antisense compounds were designed to target different regions of the frameshift site of the model RNA constructs of the SARS coronavirus (GenBank accession number NC_004718, incorporated herein as SEQ ID NO:16). The compounds are shown in Table 16. "Target site" indicates the first (5′-most) nucleotide number to which the compound binds (with reference to SEQ ID NO:16). The oligonucleotides tested include: ISIS 329721, ISIS 329722, ISIS 329724, ISIS 329727, ISIS 329729, ISIS 329731, ISIS 329550, and ISIS 339289. The negative control oligonucleotide was ISIS 329804. All compounds in Table 16 are uniform 2′-O-methoxyethyl oligonucleotides 20 nucleotides in length. The internucleoside (backbone) linkages are phosphodiester (P=O) throughout the oligonucleotide except for ISIS 329550 in which the internucleoside linkages are phosphorothioate (P=S). All cytidine residues are 5-methylcytidines. The compounds were analyzed for their effect on ribosomal frameshifting of the RNA of coronaviruses as described in Example 30. Standard error is ±4%. Percent inhibition provides an indication of the effectiveness of each oligonucleotide in decreasing the frameshift efficiency and is calculated as follows:

TABLE 16

Modulation of Frameshifting Efficiency of RNA of the SARS Coronavirus by 2′-O-Methoxyethyl Oligonucleotides

| Oligo (ISIS No) | Target Site | Target Region | Oligo-nucleotide Conc. (µM) | Frameshift Efficiency (%) | % Inhibition of Frameshift Efficiency |
|---|---|---|---|---|---|
| 329721 | 13385 | stem 1 up | 50 | 96 | 0 |
| 329721 | 13385 | stem 1 up | 25 | 105 | 0 |
| 329721 | 13385 | stem 1 up | 15 | 109 | 0 |
| 329721 | 13385 | stem 1 up | 10 | 89 | 0 |
| 329721 | 13385 | stem 1 up | 5 | 88 | 0 |
| 329721 | 13385 | stem 1 up | 0.5 | 69 | 0 |
| 329721 | 13385 | stem 1 up | 0.02 | 52 | 0 |
| 329721 | 13385 | stem 1 up | 0.002 | 55 | 0 |
| 329722 | 13392 | loop 1 | 160 | 4 | 91 |
| 329722 | 13392 | loop 1 | 20 | 13 | 66 |
| 329722 | 13392 | loop 1 | 15 | 13 | 67 |
| 329722 | 13392 | loop 1 | 10 | 13 | 68 |
| 329722 | 13392 | loop 1 | 5 | 18 | 55 |
| 329722 | 13392 | loop 1 | 0.2 | 45 | 0 |
| 329722 | 13392 | loop 1 | 0.02 | 47 | 0 |
| 329722 | 13392 | loop 1 | 0.002 | 52 | 0 |
| 329724 | 13396 | stem 2 down | 70 | 8 | 67 |
| 329724 | 13396 | stem 2 down | 20 | 9 | 66 |
| 329724 | 13396 | stem 2 down | 10 | 10 | 61 |
| 329724 | 13396 | stem 2 down | 5 | 15 | 44 |
| 329724 | 13396 | stem 2 down | 1 | 22 | 15 |
| 329724 | 13396 | stem 2 down | 0.2 | 25 | 4 |
| 329724 | 13396 | stem 2 down | 0.02 | 28 | 0 |
| 329724 | 13396 | stem 2 down | 0.002 | 26 | 1 |
| 329727 | 13426 | loop 2 | 58 | 8 | 69 |
| 329727 | 13426 | loop 2 | 20 | 7 | 71 |
| 329727 | 13426 | loop 2 | 15 | 10 | 60 |
| 329727 | 13426 | loop 2 | 10 | 13 | 52 |
| 329727 | 13426 | loop 2 | 5 | 13 | 51 |
| 329727 | 13426 | loop 2 | 0.2 | 27 | 0 |
| 329727 | 13426 | loop 2 | 0.02 | 29 | 0 |
| 329727 | 13426 | loop 2 | 0.002 | 27 | 0 |
| 339289 | 13441 | stem 2 up | 5 | 0 | 100 |
| 339289 | 13441 | stem 2 up | 2 | 0 | 98 |
| 339289 | 13441 | stem 2 up | 1 | 2 | 92 |
| 339289 | 13441 | stem 2 up | 0.8 | 3 | 86 |
| 339289 | 13441 | stem 2 up | 0.4 | 6 | 73 |
| 339289 | 13441 | stem 2 up | 0.3 | 6 | 73 |
| 339289 | 13441 | stem 2 up | 0.2 | 9 | 61 |
| 339289 | 13441 | stem 2 up | 0.1 | 14 | 35 |
| 339289 | 13441 | stem 2 up | 0.05 | 20 | 9 |
| 339289 | 13441 | stem 2 up | 0.01 | 20 | 8 |
| 329729 | 13445 | stem 2 up | 5 | 2 | 96 |
| 329729 | 13445 | stem 2 up | 1 | 8 | 81 |
| 329729 | 13445 | stem 2 up | 0.5 | 13 | 66 |
| 329729 | 13445 | stem 2 up | 0.2 | 20 | 50 |
| 329729 | 13445 | stem 2 up | 0.1 | 34 | 16 |
| 329729 | 13445 | stem 2 up | 0.01 | 40 | 1 |
| 329729 | 13445 | stem 2 up | 0.001 | 41 | 0 |
| 329731 | 13452 | stem 2 up | 33.8 | 0 | 100 |
| 329731 | 13452 | stem 2 up | 25 | 2 | 93 |
| 329731 | 13452 | stem 2 up | 15 | 6 | 76 |
| 329731 | 13452 | stem 2 up | 10 | 12 | 53 |
| 329731 | 13452 | stem 2 up | 5 | 12 | 54 |
| 329731 | 13452 | stem 2 up | 1 | 18 | 30 |
| 329731 | 13452 | stem 2 up | 0.02 | 22 | 15 |
| 329731 | 13452 | stem 2 up | 0.002 | 21 | 19 |
| 329550 | 13445 | stem 2 up | 28 | 1 | 96 |
| 329550 | 13445 | stem 2 up | 14 | 0 | 99 |
| 329550 | 13445 | stem 2 up | 2.8 | 3 | 91 |
| 329550 | 13445 | stem 2 up | 1.4 | 4 | 85 |
| 329550 | 13445 | stem 2 up | 0.7 | 6 | 79 |
| 329550 | 13445 | stem 2 up | 0.14 | 18 | 37 |
| 329550 | 13445 | stem 2 up | 0.014 | 30 | 0 |
| 329550 | 13445 | stem 2 up | 0.0014 | 28 | 0 |
| 329804 | — | control | 39.5 | 46 | 0 |
| 329804 | — | control | 25 | 58 | 0 |
| 329804 | — | control | 15 | 49 | 0 |
| 329804 | — | control | 10 | 34 | 15 |
| 329804 | — | control | 5 | 34 | 15 |

TABLE 16-continued

Modulation of Frameshifting Efficiency of RNA of the SARS
Coronavirus by 2'-O-Methoxyethyl Oligonucleotides

| Oligo (ISIS No) | Target Site | Target Region | Oligo-nucleotide Conc. (μM) | Frameshift Efficiency (%) | % Inhibition of Frameshift Efficiency |
|---|---|---|---|---|---|
| 329804 | — | control | 0.2 | 39 | 3 |
| 329804 | — | control | 0.02 | 41 | 0 |

As indicated in Table 16, the control oligonucleotide ISIS 329804 had a minimal effect on frameshift efficiency. Measurements of frameshift inhibition at 10 and 5 μM oligonucleotide were only slightly greater than experimental error while at other concentrations of oligonucleotide, frameshift inhibition was not observed at all.

Oligonucleotides 329722, 329724, 329727, 329550 and 329731 were effective at inhibiting frameshift efficiency at oligonucleotide concentrations ranging from 25-5 μM where IC50 values are estimated to be in the 10-5 μM within experimental error.

Oligonucleotides 329729 and 339289 were even more effective at inhibiting frameshift efficiency, having an IC50 value of 0.2 μM and 0.15 μM respectively.

Oligonucleotide 329721 had the effect of increasing the frameshift efficiency.

The foregoing example indicates that oligonucleotides are effective at both decreasing and increasing the frameshift efficiency of a ribosomal frameshift site of viral RNA.

Various modifications of the invention, in addition to those described herein, will be apparent to those skilled in the art from the foregoing description. Such modifications are also intended to fall within the scope of the appended claims. Each of the patents, applications, printed publications, and other published documents mentioned or referred to in this specification are herein incorporated by reference in their entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. An antisense oligonucleotide 12 to 50 nucleobases in length targeted to nucleobases 2 to 73 of a nucleic acid molecule encoding severe acute respiratory syndrome (SARS) virus (SEQ ID NO: 29752), wherein said oligonucleotide specifically hybridizes with the nucleic acid molecule encoding SARS virus.

2. The oligonucleotide of claim 1 which is 15 to 30 nucleobases in length.

3. The oligonucleotide of claim 1 which is a chimeric oligonucleotide.

4. The oligonucleotide of claim 1 comprising at least one modified internucleoside linkage, modified sugar moiety, or modified nucleobase.

5. The oligonucleotide of claim 4 comprising at least one 2'-O-methoxyethyl sugar moiety.

6. The oligonucleotide of claim 4 comprising at least one phosphorothioate internucleoside linkage.

7. The oligonucleotide of claim 4 comprising at least one 5-methylcytosine.

8. The oligonucleotide of claim 1 which is single-stranded.

9. The oligonucleotide of claim 1 targeted to nucleobases 2 to 71 of said nucleic acid molecule encoding SARS virus (SEQ ID NO: 29752).

10. The oligonucleotide of claim 9, comprising at least an 8-nucleobase portion of SEQ ID NO: 22, 23, 24 or 54.

11. The oligonucleotide of claim 10, wherein the nucleotide sequence consists of SEQ ID NO: 24.

12. The oligonucleotide of claim 5, comprising a 2'-O-methoxyethyl sugar moiety at each nucleotide.

13. The oligonucleotide of claim 4, comprising at least one locked nucleic acid.

14. The oligonucleotide of claim 13, comprising a locked nucleic acid at each nucleotide.

15. The oligonucleotide of claim 4, comprising at least one peptide nucleic acid.

16. The oligonucleotide of claim 15, comprising a peptide nucleic acid at each nucleotide.

17. The oligonucleotide of claim 4, comprising at least one morpholino modification.

18. The oligonucleotide of claim 17, comprising a morpholino modification at each position.

* * * * *